US011041859B2

(12) United States Patent
Chen et al.

(10) Patent No.: US 11,041,859 B2
(45) Date of Patent: Jun. 22, 2021

(54) METHODS OF IDENTIFYING SENP1 INHIBITORS

(71) Applicant: City of Hope, Duarte, CA (US)

(72) Inventors: Yuan Chen, Arcadia, CA (US);
Chih-Hong Chen, Duarte, CA (US);
Andrew Namanja, Duarte, CA (US)

(73) Assignee: CITY OF HOPE, Duarte, CA (US)

(*) Notice: Subject to any disclaimer, the term of this patent is extended or adjusted under 35 U.S.C. 154(b) by 114 days.

(21) Appl. No.: 15/783,423

(22) Filed: Oct. 13, 2017

(65) Prior Publication Data

US 2018/0143196 A1 May 24, 2018

Related U.S. Application Data

(62) Division of application No. 14/247,153, filed on Apr. 7, 2014, now Pat. No. 9,791,447.

(60) Provisional application No. 61/813,832, filed on Apr. 19, 2013, provisional application No. 61/809,208, filed on Apr. 5, 2013.

(51) Int. Cl.
*G01N 33/573* (2006.01)

(52) U.S. Cl.
CPC ....... *G01N 33/573* (2013.01); *G01N 2440/36* (2013.01); *G01N 2500/02* (2013.01)

(58) Field of Classification Search
CPC .................................................. G01N 33/573
See application file for complete search history.

(56) References Cited

U.S. PATENT DOCUMENTS

| 9,791,447 B2 | 10/2017 | Chen et al. |
| 2006/0057623 A1 | 3/2006 | Yeh |
| 2009/0162846 A1 | 6/2009 | Holcomb et al. |
| 2012/0302815 A1 | 11/2012 | Chen et al. |
| 2013/0245032 A1 | 9/2013 | Chen et al. |
| 2013/0317101 A1 | 11/2013 | Chen et al. |
| 2015/0158931 A1 | 6/2015 | Ovaa et al. |

FOREIGN PATENT DOCUMENTS

| WO | WO-2009/027973 A1 | 3/2009 |
| WO | WO-2009/029880 A2 | 3/2009 |
| WO | WO-2009/029880 A3 | 3/2009 |
| WO | WO-2009/029896 A1 | 3/2009 |
| WO | WO-2012/064887 A1 | 5/2012 |
| WO | WO-2012/064898 A1 | 5/2012 |
| WO | WO 2013/043970 * | 3/2013 |

OTHER PUBLICATIONS

Altschul, S.F. et al. (Sep. 1997). "Gapped BLAST and PSI-BLAST: a new generation of protein database search programs," *Nuc. Acids Res.* 25(17):3389-3402.
Bang, D. et al. (Apr. 5, 2005, e-published Mar. 22, 2005). "His6 tag-assisted chemical protein synthesis," *Proc. Natl. Acad. Sci. USA*, 102(14):5014-5019.
Batzer, M.A. et al. (Sep. 25, 1991). "Enhanced evolutionary PCR using oligonucleotides with inosine at the 3'-terminus," *Nucleic Acid Res.* 19(18):5081.
Eghbalnia, H.R. et al. (Sep. 14, 2005). High-resolution iterative frequency identification for NMR as a general strategy for multi-dimensional data collection, *J. Am. Chem. Soc.* 127(36): 12528-12536.
Friesner, R.A. et al. (Mar. 25, 2004). "Glide: a new approach for rapid, accurate docking and scoring. 1. Method and assessment of docking accuracy," *J Med Chem* 47(7):1739-1749.
Hay, R.T. (Apr. 2005). "SUMO: a history of modification," *Mol Cell* 18(1):1-12.
Henikoff, S. et al. (Nov. 15, 1989). "Amino acid substitution matrices from protein blocks," *Proc. Natl. Acad. Sci. USA* 89(22):10915-10919.
Hiller, S. et al. (Aug. 2, 2005, e-published Jul. 25, 2005). "Automated projection spectroscopy (APSY)," *Proc. Natl. Acad. Sci. U.S.A.* 102(31):10876-10881.
Kolli, N. et al. (Sep. 1, 2010). "Distribution and paralogue specificity of mammalian deSUMOylating enzymes," *Biochemical Journal* 430(2):335-344.
Kunkel, T.A. (Jan. 1985). "Rapid and efficient site-specific mutagenesis without phenotypic selection," *Proc. Natl. Acad. Sci. USA* 82(2):488-492.
Lewis, M.K. et al. (Jun. 25, 1990). "Efficient site directed in vitro mutagenesis using ampicillin selection," *Nucl. Acids Res.*, 18:3439-3443.
Markley, J.L. et al. (1998). "Recommendations for the Presentation of NMR Structures of Proteins and Nucleic Acids," *Pure & Appl. Chem.* 70(1):117-142.
Mikolajczyk, J. et al. (Sep. 7, 2007). "Small ubiquitin-related modifier (SUMO)-specific proteases: profiling the specificities and activities of human SENPs," *Journal of Biological Chemistry* 282(36):26217-26224.
Namanja, A.T. et al. (Jan. 27, 2012, e-published Dec. 6, 2011). "Insights into high affinity small ubiquitin-like modifier (SUMO) recognition by SUMO-interacting motifs (SIMs) revealed by a combination of NMR and peptide array analysis," *The Journal of Biological Chemistry* 287(5):3231-3240.
Nefkens, I. et al. (Feb. 1, 2003). "Heat shock and Cd2+ exposure regulate PML and Daxx release from ND10 by independent mechanisms that modify the induction of heat-shock proteins 70 and 25 differently," *J. Cell Sci.* 116(Pt. 3):513-524.
Ohtsuka, E. et al. (Mar. 10, 1985). "An alternative approach to deoxyoligonucleotides as hybridization probes by insertion of deoxyinosine at ambiguous codon positions," *J. Biol. Chem.* 260(5):2605-2608.
Pearson, W.R. et al. (Apr. 1988). "Improved tools for biological sequence comparison," *Proc. Nat'l. Acad. Sci. USA* 85(8):2444-2448.
Reverter, D. et al. (Dec. 2006, e-published Nov. 12, 2006). "Structural basis for SENP2 protease interactions with SUMO precursors and conjugated substrates," *Nat. Struct. Mol. Biol.* 13:1060-1068.

(Continued)

*Primary Examiner* — Suzanne M Noakes
(74) *Attorney, Agent, or Firm* — Mintz, Levin, Cohn, Ferris, Glovsky and Popeo, P.C.

(57) ABSTRACT

Provided herein are methods of detecting binding of an SENP1 polypeptide to a compound and methods for screening for inhibitors of SENP1. Further provided are aqueous compositions comprising SENP1 polypeptides and NMR apparatuses comprising the compositions for NMR analysis.

12 Claims, 7 Drawing Sheets

Specification includes a Sequence Listing.

(56) References Cited

OTHER PUBLICATIONS

Rossi, A.M. et al. (Mar. 2011, e-published Mar. 3, 2011). "Analysis of protein-ligand interactions by fluorescence polarization," *Nat. Protoc.* 6(3):365-387.

Shen, L.N. et al. (Jul. 15, 2006). "The structure of SENP1-SUMO-2 complex suggests a structural basis for discrimination between SUMO paralogues during processing," *Biochem. J.* 397(2):279-288.

Shen, L. et al. (Dec. 2006, e-published Nov. 12, 2006). "SUMO protease SENP1 induces isomerization of the scissile peptide bond," *Nat. Struct. Mol. Biol.* 13(12):1069-1077.

Shin, L. et al. (Apr. 13, 2012). "DeSUMOylating isopeptidase: a second class of SUMO protease," *EMBO Rep.* 13(4):339-346.

Song, J. et al. (Oct. 5, 2004, e-published Sep. 23, 2004). Identification of a SUMO-binding motif that recognizes SUMO-modified proteins, *PNAS USA* 101(40):14373-14378.

Szyperski, T. et al. (Jun. 11, 2002). "Reduced-dimensionality NMR spectroscopy for high-throughput protein resonance assignment," *Proc. Natl. Acad. Sci. U.S.A.* 99(12):8009-8014.

Tatham, M.H. et al. (2009). "Fret-based in vitro assays for the analysis of SUMO protease activities," *Methods Mol. Biol.* 497:253-268.

Xu, Z. et al. (Sep. 15, 2006). "Crystal structure of the SENP1 mutant C603S-SUMO complex reveals the hydrolytic mechanism of SUMO-specific protease," *Biochem. J* 398(3):345-352.

\* cited by examiner

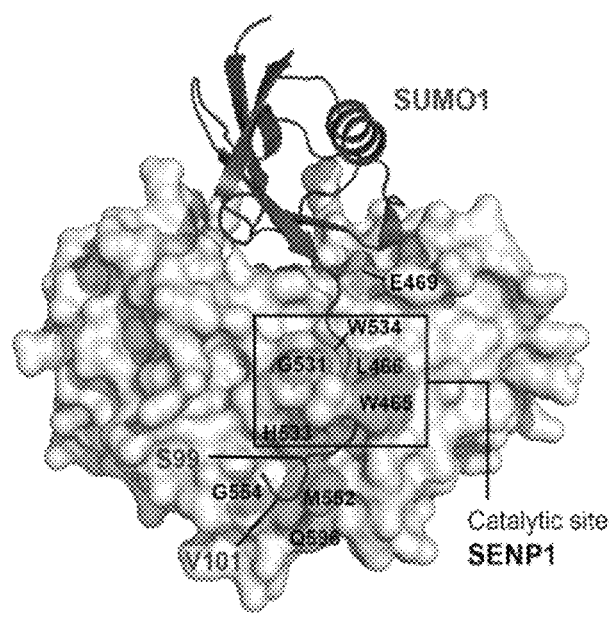
FIG. 8
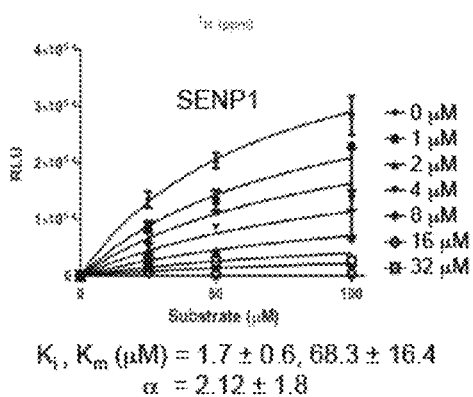
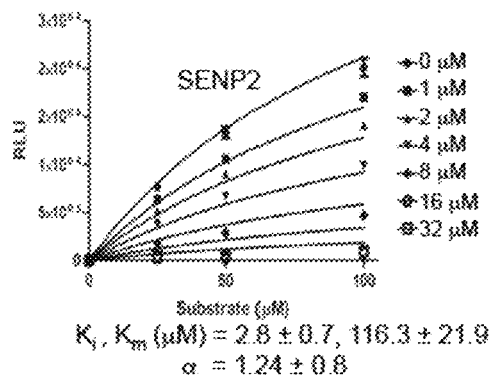
FIG. 9A
FIG. 9B

SEQUENCE LISTING

```
<160> NUMBER OF SEQ ID NOS: 9

<210> SEQ ID NO 1
<211> LENGTH: 644
<212> TYPE: PRT
<213> ORGANISM: Homo sapiens

<400> SEQUENCE: 1
```

Met Asp Asp Ile Ala Asp Arg Met Arg Met Asp Ala Gly Glu Val Thr
1               5                   10                  15

Leu Val Asn His Asn Ser Val Phe Lys Thr His Leu Leu Pro Gln Thr
            20                  25                  30

Gly Phe Pro Glu Asp Gln Leu Ser Leu Ser Asp Gln Gln Ile Leu Ser
        35                  40                  45

Ser Arg Gln Gly His Leu Asp Arg Ser Phe Thr Cys Ser Thr Arg Ser

```
            50                  55                  60
Ala Ala Tyr Asn Pro Ser Tyr Tyr Ser Asp Asn Pro Ser Ser Asp Ser
 65                  70                  75                  80

Phe Leu Gly Ser Gly Asp Leu Arg Thr Phe Gly Gln Ser Ala Asn Gly
                     85                  90                  95

Gln Trp Arg Asn Ser Thr Pro Ser Ser Ser Ser Leu Gln Lys Ser
                    100                 105                 110

Arg Asn Ser Arg Ser Leu Tyr Leu Glu Thr Arg Lys Thr Ser Ser Gly
                    115                 120                 125

Leu Ser Asn Ser Phe Ala Gly Lys Ser Asn His His Cys His Val Ser
                    130                 135                 140

Ala Tyr Glu Lys Ser Phe Pro Ile Lys Pro Val Pro Ser Pro Ser Trp
145                 150                 155                 160

Ser Gly Ser Cys Arg Arg Ser Leu Leu Ser Pro Lys Lys Thr Gln Arg
                    165                 170                 175

Arg His Val Ser Thr Ala Glu Glu Thr Val Gln Glu Glu Glu Arg Glu
                    180                 185                 190

Ile Tyr Arg Gln Leu Leu Gln Met Val Thr Gly Lys Gln Phe Thr Ile
                    195                 200                 205

Ala Lys Pro Thr Thr His Phe Pro Leu His Leu Ser Arg Cys Leu Ser
210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Ser Gly Ser Ala
                    245                 250                 255

Ser Ile Leu Thr Asn Gln Glu Gln Leu Ser His Ser Val Tyr Ser Leu
                    260                 265                 270

Ser Ser Tyr Thr Pro Asp Val Ala Phe Gly Ser Lys Asp Ser Gly Thr
                    275                 280                 285

Leu His His Pro His His His Ser Val Pro His Gln Pro Asp Asn
                    290                 295                 300

Leu Ala Ala Ser Asn Thr Gln Ser Glu Gly Ser Asp Ser Val Ile Leu
305                 310                 315                 320

Leu Lys Val Lys Asp Ser Gln Thr Pro Thr Pro Ser Ser Thr Phe Phe
                    325                 330                 335

Gln Ala Glu Leu Trp Ile Lys Glu Leu Thr Ser Val Tyr Asp Ser Arg
                    340                 345                 350

Ala Arg Glu Arg Leu Arg Gln Ile Glu Glu Gln Lys Ala Leu Ala Leu
                    355                 360                 365

Gln Leu Gln Asn Gln Arg Leu Gln Glu Arg Glu His Ser Val His Asp
                    370                 375                 380

Ser Val Glu Leu His Leu Arg Val Pro Leu Glu Lys Glu Ile Pro Val
385                 390                 395                 400

Thr Val Val Gln Glu Thr Gln Lys Lys Gly His Lys Leu Thr Asp Ser
                    405                 410                 415

Glu Asp Glu Phe Pro Glu Ile Thr Glu Glu Met Glu Lys Glu Ile Lys
                    420                 425                 430

Asn Val Phe Arg Asn Gly Asn Gln Asp Glu Val Leu Ser Glu Ala Phe
                    435                 440                 445

Arg Leu Thr Ile Thr Arg Lys Asp Ile Gln Thr Leu Asn His Leu Asn
                    450                 455                 460

Trp Leu Asn Asp Glu Ile Ile Asn Phe Tyr Met Asn Met Leu Met Glu
465                 470                 475                 480
```

```
Arg Ser Lys Glu Lys Gly Leu Pro Ser Val His Ala Phe Asn Thr Phe
                485                 490                 495

Phe Phe Thr Lys Leu Lys Thr Ala Gly Tyr Gln Ala Val Lys Arg Trp
                500                 505                 510

Thr Lys Lys Val Asp Val Phe Ser Val Asp Ile Leu Leu Val Pro Ile
                515                 520                 525

His Leu Gly Val His Trp Cys Leu Ala Val Val Asp Phe Arg Lys Lys
                530                 535                 540

Asn Ile Thr Tyr Tyr Asp Ser Met Gly Gly Ile Asn Asn Glu Ala Cys
545                 550                 555                 560

Arg Ile Leu Leu Gln Tyr Leu Lys Gln Glu Ser Ile Asp Lys Lys Arg
                565                 570                 575

Lys Glu Phe Asp Thr Asn Gly Trp Gln Leu Phe Ser Lys Lys Ser Gln
                580                 585                 590

Glu Ile Pro Gln Gln Met Asn Gly Ser Asp Cys Gly Met Phe Ala Cys
                595                 600                 605

Lys Tyr Ala Asp Cys Ile Thr Lys Asp Arg Pro Ile Asn Phe Thr Gln
                610                 615                 620

Gln His Met Pro Tyr Phe Arg Lys Arg Met Val Trp Glu Ile Leu His
625                 630                 635                 640

Arg Lys Leu Leu

<210> SEQ ID NO 2
<211> LENGTH: 643
<212> TYPE: PRT
<213> ORGANISM: Homo sapiens

<400> SEQUENCE: 2

Met Asp Asp Ile Ala Asp Arg Met Arg Met Asp Ala Gly Glu Val Thr
1               5                   10                  15

Leu Val Asn His Asn Ser Val Phe Lys Thr His Leu Leu Pro Gln Thr
                20                  25                  30

Gly Phe Pro Glu Asp Gln Leu Ser Leu Ser Asp Gln Gln Ile Leu Ser
                35                  40                  45

Ser Arg Gln Gly His Leu Asp Arg Ser Phe Thr Cys Ser Thr Arg Ser
    50                  55                  60

Ala Ala Tyr Asn Pro Ser Tyr Tyr Ser Asp Asn Pro Ser Ser Asp Ser
65                  70                  75                  80

Phe Leu Gly Ser Gly Asp Leu Arg Thr Phe Gly Gln Ser Ala Asn Gly
                85                  90                  95

Gln Trp Arg Asn Ser Thr Pro Ser Ser Ser Ser Leu Gln Lys Ser
                100                 105                 110

Arg Asn Ser Arg Ser Leu Tyr Leu Glu Thr Arg Lys Thr Ser Ser Gly
                115                 120                 125

Leu Ser Asn Ser Phe Ala Gly Lys Ser Asn His His Cys His Val Ser
                130                 135                 140

Ala Tyr Glu Lys Ser Phe Pro Ile Lys Pro Val Pro Ser Pro Ser Trp
145                 150                 155                 160

Ser Gly Ser Cys Arg Arg Ser Leu Leu Ser Pro Lys Thr Gln Arg
                165                 170                 175

Arg His Val Ser Thr Ala Glu Glu Thr Val Gln Glu Glu Arg Glu
                180                 185                 190

Ile Tyr Arg Gln Leu Leu Gln Met Val Thr Gly Lys Gln Phe Thr Ile
                195                 200                 205
```

```
Ala Lys Pro Thr Thr His Phe Pro Leu His Leu Ser Arg Cys Leu Ser
    210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Gly Ser Ala
                245                 250                 255

Ser Ile Leu Thr Asn Gln Glu Gln Leu Ser His Ser Val Tyr Ser Leu
                260                 265                 270

Ser Ser Tyr Thr Pro Asp Val Ala Phe Gly Ser Lys Asp Ser Gly Thr
        275                 280                 285

Leu His His Pro His His His Ser Val Pro His Gln Pro Asp Asn
        290                 295                 300

Leu Ala Ala Ser Asn Thr Gln Ser Glu Gly Ser Asp Ser Val Ile Leu
305                 310                 315                 320

Leu Lys Val Lys Asp Ser Gln Thr Pro Thr Pro Ser Ser Thr Phe Phe
                325                 330                 335

Gln Ala Glu Leu Trp Ile Lys Glu Leu Thr Ser Val Tyr Asp Ser Arg
                340                 345                 350

Ala Arg Glu Arg Leu Arg Gln Ile Glu Glu Gln Lys Ala Leu Ala Leu
        355                 360                 365

Gln Leu Gln Asn Gln Arg Leu Gln Glu Arg Glu His Ser Val His Asp
370                 375                 380

Ser Val Glu Leu His Leu Arg Val Pro Leu Glu Lys Glu Ile Pro Val
385                 390                 395                 400

Thr Val Val Gln Glu Thr Gln Lys Lys Gly His Lys Leu Thr Asp Ser
                405                 410                 415

Glu Asp Glu Phe Pro Glu Ile Thr Glu Glu Met Glu Lys Glu Ile Lys
                420                 425                 430

Asn Val Phe Arg Asn Gly Asn Gln Asp Glu Val Leu Ser Glu Ala Phe
                435                 440                 445

Arg Leu Thr Ile Thr Arg Lys Asp Ile Gln Thr Leu Asn His Leu Asn
450                 455                 460

Trp Leu Asn Asp Glu Ile Ile Asn Phe Tyr Met Asn Met Leu Met Glu
465                 470                 475                 480

Arg Ser Lys Glu Lys Gly Leu Pro Ser Val His Ala Phe Asn Thr Phe
                485                 490                 495

Phe Phe Thr Lys Leu Lys Thr Ala Gly Tyr Gln Ala Val Lys Arg Trp
                500                 505                 510

Thr Lys Lys Val Asp Val Phe Ser Val Asp Ile Leu Leu Val Pro Ile
        515                 520                 525

His Leu Gly Val His Trp Cys Leu Ala Val Val Asp Phe Arg Lys Lys
530                 535                 540

Asn Ile Thr Tyr Tyr Asp Ser Met Gly Gly Ile Asn Asn Glu Ala Cys
545                 550                 555                 560

Arg Ile Leu Leu Gln Tyr Leu Lys Gln Glu Ser Ile Asp Lys Lys Arg
                565                 570                 575

Lys Glu Phe Asp Thr Asn Gly Trp Gln Leu Phe Ser Lys Lys Ser Gln
                580                 585                 590

Ile Pro Gln Gln Met Asn Gly Ser Asp Cys Gly Met Phe Ala Cys Lys
        595                 600                 605

Tyr Ala Asp Cys Ile Thr Lys Asp Arg Pro Ile Asn Phe Thr Gln Gln
610                 615                 620
```

His Met Pro Tyr Phe Arg Lys Arg Met Val Trp Glu Ile Leu His Arg
625                 630                 635                 640

Lys Leu Leu

<210> SEQ ID NO 3
<211> LENGTH: 226
<212> TYPE: PRT
<213> ORGANISM: Homo sapiens

<400> SEQUENCE: 3

Glu Phe Pro Glu Ile Thr Glu Met Glu Lys Glu Ile Lys Asn Val
1               5                   10                  15

Phe Arg Asn Gly Asn Gln Asp Glu Val Leu Ser Glu Ala Phe Arg Leu
                20                  25                  30

Thr Ile Thr Arg Lys Asp Ile Gln Thr Leu Asn His Leu Asn Trp Leu
                35                  40                  45

Asn Asp Glu Ile Ile Asn Phe Tyr Met Asn Met Leu Met Glu Arg Ser
            50                  55                  60

Lys Glu Lys Gly Leu Pro Ser Val His Ala Phe Asn Thr Phe Phe Phe
65                  70                  75                  80

Thr Lys Leu Lys Thr Ala Gly Tyr Gln Ala Val Lys Arg Trp Thr Lys
                85                  90                  95

Lys Val Asp Val Phe Ser Val Asp Ile Leu Leu Val Pro Ile His Leu
                100                 105                 110

Gly Val His Trp Cys Leu Ala Val Val Asp Phe Arg Lys Lys Asn Ile
            115                 120                 125

Thr Tyr Tyr Asp Ser Met Gly Gly Ile Asn Asn Glu Ala Cys Arg Ile
130                 135                 140

Leu Leu Gln Tyr Leu Lys Gln Glu Ser Ile Asp Lys Lys Arg Lys Glu
145                 150                 155                 160

Phe Asp Thr Asn Gly Trp Gln Leu Phe Ser Lys Lys Ser Gln Glu Ile
                165                 170                 175

Pro Gln Gln Met Asn Gly Ser Asp Cys Gly Met Phe Ala Cys Lys Tyr
                180                 185                 190

Ala Asp Cys Ile Thr Lys Asp Arg Pro Ile Asn Phe Thr Gln Gln His
            195                 200                 205

Met Pro Tyr Phe Arg Lys Arg Met Val Trp Glu Ile Leu His Arg Lys
            210                 215                 220

Leu Leu
225

<210> SEQ ID NO 4
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 4

Glu Phe Pro Glu Ile Thr Glu Met Glu Lys Glu Ile Lys Asn Val
1               5                   10                  15

Phe Arg Asn Gly Asn Gln Asp Glu Val Leu Ser Glu Ala Phe Arg Leu
                20                  25                  30

Thr Ile Thr Arg Lys Asp Ile Gln Thr Leu Asn His Leu Asn Trp Leu
                35                  40                  45

Asn Asp Glu Ile Ile Asn Phe Tyr Met Asn Met Leu Met Glu Arg Ser
            50                  55                  60

```
Lys Glu Lys Gly Leu Pro Ser Val His Ala Phe Asn Thr Phe Phe Phe
 65                  70                  75                  80

Thr Lys Leu Lys Thr Ala Gly Tyr Gln Ala Val Lys Arg Trp Thr Lys
                 85                  90                  95

Lys Val Asp Val Phe Ser Val Asp Ile Leu Val Pro Ile His Leu
            100                 105                 110

Gly Val His Trp Cys Leu Ala Val Val Asp Phe Arg Lys Lys Asn Ile
            115                 120                 125

Thr Tyr Tyr Asp Ser Met Gly Gly Ile Asn Asn Glu Ala Cys Arg Ile
            130                 135                 140

Leu Leu Gln Tyr Leu Lys Gln Glu Ser Ile Asp Lys Lys Arg Lys Glu
145                 150                 155                 160

Phe Asp Thr Asn Gly Trp Gln Leu Phe Ser Lys Lys Ser Gln Glu Ile
                165                 170                 175

Pro Gln Gln Met Asn Gly Ser Asp Ser Gly Met Phe Ala Cys Lys Tyr
            180                 185                 190

Ala Asp Cys Ile Thr Lys Asp Arg Pro Ile Asn Phe Thr Gln Gln His
            195                 200                 205

Met Pro Tyr Phe Arg Lys Arg Met Val Trp Glu Ile Leu His Arg Lys
    210                 215                 220

Leu Leu
225

<210> SEQ ID NO 5
<211> LENGTH: 225
<212> TYPE: PRT
<213> ORGANISM: Homo sapiens

<400> SEQUENCE: 5

Glu Phe Pro Glu Ile Thr Glu Met Glu Lys Glu Ile Lys Asn Val
  1               5                  10                  15

Phe Arg Asn Gly Asn Gln Asp Glu Val Leu Ser Glu Ala Phe Arg Leu
             20                  25                  30

Thr Ile Thr Arg Lys Asp Ile Gln Thr Leu Asn His Leu Asn Trp Leu
             35                  40                  45

Asn Asp Glu Ile Ile Asn Phe Tyr Met Asn Met Leu Met Glu Arg Ser
 50                  55                  60

Lys Glu Lys Gly Leu Pro Ser Val His Ala Phe Asn Thr Phe Phe Phe
 65                  70                  75                  80

Thr Lys Leu Lys Thr Ala Gly Tyr Gln Ala Val Lys Arg Trp Thr Lys
                 85                  90                  95

Lys Val Asp Val Phe Ser Val Asp Ile Leu Val Pro Ile His Leu
            100                 105                 110

Gly Val His Trp Cys Leu Ala Val Val Asp Phe Arg Lys Lys Asn Ile
            115                 120                 125

Thr Tyr Tyr Asp Ser Met Gly Gly Ile Asn Asn Glu Ala Cys Arg Ile
            130                 135                 140

Leu Leu Gln Tyr Leu Lys Gln Glu Ser Ile Asp Lys Lys Arg Lys Glu
145                 150                 155                 160

Phe Asp Thr Asn Gly Trp Gln Leu Phe Ser Lys Lys Ser Gln Ile Pro
                165                 170                 175

Gln Gln Met Asn Gly Ser Asp Cys Gly Met Phe Ala Cys Lys Tyr Ala
            180                 185                 190

Asp Cys Ile Thr Lys Asp Arg Pro Ile Asn Phe Thr Gln Gln His Met
```

```
                195                 200                 205
Pro Tyr Phe Arg Lys Arg Met Val Trp Glu Ile Leu His Arg Lys Leu
    210                 215                 220

Leu
225

<210> SEQ ID NO 6
<211> LENGTH: 164
<212> TYPE: PRT
<213> ORGANISM: Homo sapiens

<400> SEQUENCE: 6

Leu Thr Ile Thr Arg Lys Asp Ile Gln Thr Leu Asn His Leu Asn Trp
1               5                   10                  15

Leu Asn Asp Glu Ile Ile Asn Phe Tyr Met Asn Met Leu Met Glu Arg
            20                  25                  30

Ser Lys Glu Lys Gly Leu Pro Ser Val His Ala Phe Asn Thr Phe Phe
        35                  40                  45

Phe Thr Lys Leu Lys Thr Ala Gly Tyr Gln Ala Val Lys Arg Trp Thr
    50                  55                  60

Lys Lys Val Asp Val Phe Ser Val Asp Ile Leu Leu Val Pro Ile His
65                  70                  75                  80

Leu Gly Val His Trp Cys Leu Ala Val Val Asp Phe Arg Lys Lys Asn
                85                  90                  95

Ile Thr Tyr Tyr Asp Ser Met Gly Gly Ile Asn Asn Glu Ala Cys Arg
            100                 105                 110

Ile Leu Leu Gln Tyr Leu Lys Gln Glu Ser Ile Asp Lys Lys Arg Lys
        115                 120                 125

Glu Phe Asp Thr Asn Gly Trp Gln Leu Phe Ser Lys Lys Ser Gln Glu
    130                 135                 140

Ile Pro Gln Gln Met Asn Gly Ser Asp Cys Gly Met Phe Ala Cys Lys
145                 150                 155                 160

Tyr Ala Asp Cys

<210> SEQ ID NO 7
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 7

Leu Thr Ile Thr Arg Lys Asp Ile Gln Thr Leu Asn His Leu Asn Trp
1               5                   10                  15

Leu Asn Asp Glu Ile Ile Asn Phe Tyr Met Asn Met Leu Met Glu Arg
            20                  25                  30

Ser Lys Glu Lys Gly Leu Pro Ser Val His Ala Phe Asn Thr Phe Phe
        35                  40                  45

Phe Thr Lys Leu Lys Thr Ala Gly Tyr Gln Ala Val Lys Arg Trp Thr
    50                  55                  60

Lys Lys Val Asp Val Phe Ser Val Asp Ile Leu Leu Val Pro Ile His
65                  70                  75                  80

Leu Gly Val His Trp Cys Leu Ala Val Val Asp Phe Arg Lys Lys Asn
                85                  90                  95

Ile Thr Tyr Tyr Asp Ser Met Gly Gly Ile Asn Asn Glu Ala Cys Arg
            100                 105                 110
```

```
Ile Leu Leu Gln Tyr Leu Lys Gln Glu Ser Ile Asp Lys Lys Arg Lys
            115                 120                 125

Glu Phe Asp Thr Asn Gly Trp Gln Leu Phe Ser Lys Lys Ser Gln Glu
            130                 135                 140

Ile Pro Gln Gln Met Asn Gly Ser Asp Ser Gly Met Phe Ala Cys Lys
145                 150                 155                 160

Tyr Ala Asp Cys

<210> SEQ ID NO 8
<211> LENGTH: 101
<212> TYPE: PRT
<213> ORGANISM: Homo sapiens

<400> SEQUENCE: 8

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100

<210> SEQ ID NO 9
<211> LENGTH: 92
<212> TYPE: PRT
<213> ORGANISM: Homo sapiens

<400> SEQUENCE: 9

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln
                85                  90
```

METHODS OF IDENTIFYING SENP1 INHIBITORS

CROSS-REFERENCE TO RELATED APPLICATIONS

This application is a divisional of U.S. patent application Ser. No. 14/247,153, filed Apr. 7, 2014, now U.S. Pat. No. 9,791,447, issued Oct. 17, 2017, which claims the benefit of U.S. Provisional Patent Applications 61/809,208, filed Apr. 5, 2013, and 61/813,832, filed Apr. 19, 2013, each of which is incorporated herein by reference in its entirety and for all purposes.

STATEMENT REGARDING FEDERALLY FUNDED RESEARCH

This invention was made with government support under NM Grant Nos. R01GM074748, R01GM086171 and R01GM102538. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48440-521C01US_ST25.TXT, created on Oct. 13, 2017, 22,281 bytes, machine format IBM-PC, MS-Windows operating system, is hereby incorporated by reference.

BACKGROUND

Post-translational modifications with the small ubiquitin-like modifiers (SUMO) are initiated and removed by the activities of SUMO-specific proteases (SENPs). Unlike ubiquitylation, which has one modifier (i.e., ubiquitin) and one dominant role, namely protein degradation, SUMOylation involves three modifiers (SUMO-1, -2, and -3) and affects diverse cellular functions. There are six SENPs, organized into three families based on sequence similarity: SENP1 and 2 that catalyze maturation of SUMO precursors and removal of SUMO-1 and SUMO-2/3 conjugates; SENP3 and 5 that preferentially remove SUMO-2/3 conjugates; and SENP6 and 7 that appear to be mainly involved in editing poly-SUMO-2/3 chains. Recently, another de-SUMOylase has been discovered that does not share sequence similarity with the SENPs.

SENP inhibitors with cellular activity would be advantageous for elucidating the role of SUMOylation in cellular regulation and for validating SENPs as therapeutic targets. SENP1 and SENP3 are also potential targets for developing new therapeutic agents for cancer. They regulate the stability of hypoxia-inducible factor 1α (HIF1α), which is a key player in the formation of new blood vessels to support tumor growth. SENP1 is also highly expressed in human prostate cancer specimens and regulates androgen receptor (AR) activities. Androgen induces rapid and dynamic conjugation of SUMO-1 to AR, while SENP1 promotes AR-dependent transcription by cleaving SUMO-1-modified AR. SENP1 overexpression induces transformation of normal prostate gland tissue and facilitates the onset of high-grade prostatic intraepithelial neoplasia. Therefore, at least some members of the SENPs are potential targets for developing new cancer therapies.

SUMMARY

Provided herein are methods of detecting binding of an SENP1 polypeptide to a compound and methods for screening for inhibitors of SENP1. Further provided are aqueous compositions comprising SENP1 polypeptides and NMR apparatuses comprising the compositions for NMR analysis.

The details of one or more embodiments are set forth in the accompanying drawings and the description below. Other features, objects, and advantages will be apparent from the description and drawings, and from the claims.

DESCRIPTION OF DRAWINGS

FIG. 8 is a picture showing all SPI-01 perturbed residues on SENP1 (PDB ID: 2IY1) labeled and colored in dark grey on the surface representation of SENP1 in complex with SUMO-1 precursor. Perturbed residues that are located in the vicinity of the catalytic center of SENP1 or the C-terminus of precursor SUMO-1 are labeled in black and grey, respectively.

FIGS. 9A and 9B are graphs showing enzyme kinetic measurements for SPI-01 indicating a non-competitive mode of inhibition. The data were fit to obtain the indicated kinetic parameters ($\alpha$, $K_i$ and $K_m$) using Graphpad Prism. Lineweaver-Burk plot analysis of the data also confirmed non-competitive inhibition.

DETAILED DESCRIPTION

Figure 1:
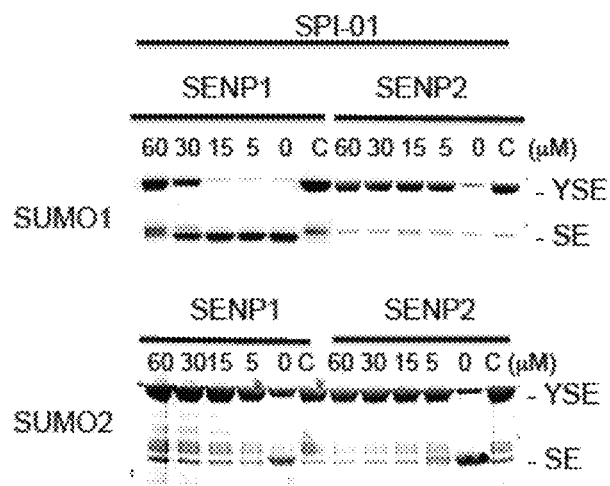
FIG. 1 is a picture of a representative Coomassie-stained gel showing cleavage of SUMO-1 and SUMO-2 by SENP1 and SENP2 in the presence of increasing concentrations of SPI-01. YSE, fusion SUMO (S) precursors flanked by YFP (Y) and ECFP (E) at the N- and C-termini, respectively.

SENP1 is a target for developing new therapeutic agents for cancer. It regulates the stability of hypoxia-inducible factor 1α (HIF1α), which is a key player in the formation of new blood vesicles to support tumor growth. SENP1 is also highly expressed in human prostate cancer specimens and regulates androgen receptor (AR) activities. SENP1 is also a target for developing anti-viral therapeutic agents for infection of viruses including, but not limited to influenza, cytomegalovirus, herpes virus, white spot syndrome virus, Epstein-Barr virus, adenovirus and HIV-1, because of the role of SUMOylation in their replication. As described in the examples below, small molecule inhibitors of SENP1 were searched for using in-silico screening in conjunction with biochemical assays. However, the data provided evidence for substrate-assisted inhibitor binding. Thus, using artificial substrates for compound screening may be misleading, as the inhibitory effects could be significantly different from using the physiological substrates. Therefore, embodiments are provided including methods and inhibitors of SENP1 that confer the non-competitive inhibitory mechanism, as shown by nuclear magnetic resonance (NMR).

For specific SENP proteins described herein (e.g., SENP1), the named protein includes any of the protein's naturally occurring forms, or variants that maintain the protein activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the SENP1 protein is the protein as identified by its NCBI sequence reference. In other embodiments, the SENP1 protein is the protein as identified by its NCBI sequence reference or functional fragment thereof.

The term "SENP1" as provided herein includes any of the Sentrin-specific protease 1 (SENP1) naturally occurring forms, homologs, isoforms or variants that maintain the protease activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the SENP1 protein is the protein as identified by the NCBI sequence reference GI:390131988 or functional fragment thereof. In embodiments, the SENP1 protein is the protein as identified by the UniProt sequence reference Q9P0U3 or functional fragment thereof. In embodiments, the SENP1 protein includes the sequence of SEQ ID NO:1, 2, 3, 4, 5, 6, or 7. In embodiments, the SENP1 protein is encoded by a nucleic acid sequences corresponding to Gene ID: 29843.

As described herein, nuclear magnetic resonance (NMR) approaches have advantages over other methods previously employed on SENP1 in identifying molecules or compounds for further development. Specifically, the methods herein provide for discovery or identification of compounds or inhibitors that selectively bind SENP1 and not other SENPs. The methods also provide for identification of compounds or inhibitors that selectively bind SENP1-physiological substrate complexes and not SENP-artificial substrate complexes. Further advantages include sensitivity to binding affinities of a wide range and, thus, allowing for identification of compounds with physicochemical properties that are amenable for a greater scope for development of leads with superior ADME (absorption, distribution, metabolism, and excretion) attributes. Optionally, the test compounds are Rule-of-three (Ro3) (MW≤300, H-bond donors/acceptors≤3, c Log P≤3, rotatable bonds≤3) compliant (Congreve et al., *Drug Discov. Today* 8(19):876-7 (2003); and Erlanson, *Top Curr. Chem.* 317:1-32 (2011)).

Nuclear magnetic resonance (NMR) studies magnetic nuclei and provide atomic resolution information on the structures of large or small molecules and their complexes. The elementary particles, neutrons and protons, composing an atomic nucleus, have the intrinsic quantum mechanical property of spin. The overall spin of the nucleus is determined by the spin quantum number I. If the number of both the protons and neutrons in a given isotope are even, then I=0. In other cases, however, the overall spin is non-zero. A non-zero spin is associated with a non-zero magnetic moment. It is this magnetic moment that is exploited in NMR. For example, nuclei that have a spin of one-half, like Hydrogen nuclei ($^1H$), a single proton, have two possible spin states (also referred to as up and down, respectively). The energies of these states are the same. Hence the populations of the two states (i.e. number of atoms in the two states) will be approximately equal at thermal equilibrium. If a nucleus is placed in a magnetic field, however, the interaction between the nuclear magnetic moment and the external magnetic field means the two states no longer have the same energy. The NMR frequency (f) is shifted by the shielding effect of the surrounding electrons. In general, this electronic shielding reduces the magnetic field at the nucleus (which is what determines the NMR frequency). As a result, the energy gap is reduced, and the frequency required to achieve resonance is also reduced. This shift of the NMR frequency due to the chemical environment is called the chemical shift, and it explains why NMR is a direct probe of chemical structure. The chemical shift in absolute terms is defined by the frequency of the resonance expressed with reference to a standard which is defined to be at 0. The scale is made manageable by expressing it in parts per million (ppm) of the standard frequency. Thus, in general, NMR spectral data are reported as chemical shift and are reported in ppm relative to either an internal standard or other baseline. A more detailed discussion of nuclear magnetic resonance may be found in, for example, C. P. Slichter, Principles of Magnetic Resonance, 3rd ed., Springer-Verlag, Berlin, pp. 1-63 (1990); J. D. Roberts, Nuclear Magnetic Resonance, Mc-Graw-Hill, N.Y., pp. 1-19 (1959); Cohen-Tannoudji et al., Quantum Mechanics, Vol. 1, New York, N.Y.: Wiley (1977); WO 2009/027973; WO 2009/029880; WO 2009/029896; Hajduk et al., "High-throughput nuclear magnetic resonance-based screening," J. Med. Chem. 42:2315-2317 (1999); and Cavanagh et al., Protein NMR Spectroscopy: Principles and Practice Academic Press: San Diego (1996), which are incorporated by reference herein in their entireties.

A variety of NMR approaches have been developed to accelerate NMR data acquisition (Atreya et al., Methods Enzymol., 394:78-108 (2005)). For example, in the field of biological NMR spectroscopy (Cavanagh et al., Protein NMR Spectroscopy, Academic Press: San Diego (2007)) stable isotope ($^{13}C/^{15}N$) labeled biological macromolecules are now studied. The isotope labeling enables one to efficiently record three-dimensional (3D) or four-dimensional (4D) $^{13}C/^{15}N$-resolved spectra. The most commonly used biological NMR methods are multi-dimensional and heteronuclear-edited NMR methods. See, for example, Tjandra and Bax, "Direct measurement of distances and angles in biomolecules by NMR in a dilute liquid crystalline medium," Science 1997 278(5340):1111-4 (1997). Erratum in: Science 278(5344):1697 (1997); Clore and Gronenborn, "NMR structure determination of proteins and protein complexes larger than 20 kDa," Curr Opin Chem Biol. October; 2(5):564-70 (1998); Mittermaier and Kay, "Observing biological dynamics at atomic resolution using NMR," Trends Biochem Sci. 34(12):601-11 (2009); and Wüthrich, Kurt, NMR of Proteins and Nucleic Acids, John Wiley, New York, N.Y. (1986). NMR techniques further include, but are not limited to, (i) Reduced-dimensionality (RD) NMR (Szyperski et al., Proc. Natl. Acad. Sci. U.S.A., 99:8009-8014 (2002)); (ii) G-matrix FT (GFT) projection NMR (Atreya et al., J. Am. Chem. Soc., 127:4554-4555 (2005); Eletsky et al., J. Am. Chem. Soc., 127:14578-14579 (2005); Yang et al., J. Am. Chem. Soc., 127:9085-9099 (2005); Szyperski et al., Magn. Reson. Chem., 44:51-60 (2006); Atreya et al., J. Am. Chem. Soc., 129:680-692 (2007); Kupce et al., J. Am. Chem. Soc., 126:6429-40 (2004); Hiller et al., Proc. Natl. Acad. Sci. U.S.A., 102:10876-10881 (2005); and Eghbalnia et al., J. Am. Chem. Soc., 127: 12528-12536 (2005)); and (iii) Covariance NMR spectroscopy (Bruschweiler, J. Chem. Phys., 121:409-414 (2004); Zhang et al., J. Am. Chem. Soc., 126:13180-13181 (2004); and Chen et al., J. Am. Chem. Soc., 128:15564-15565 (2006)). These publications are incorporated by reference herein in their entireties.

Thus, as used herein, the term nuclear magnetic resonance (NMR) encompasses a variety of methods including but not limited to, one-dimensional NMR (1D-NMR), two-dimensional NMR (2D-NMR), correlation spectroscopy NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), transverse relaxation optimized spectroscopy (TROSY-NMR) and combinations thereof. For more description on TROSY-NMR see Pervushin, et al., "Attenuated $T_2$ relaxation by mutual cancellation of dipole-dipole coupling and chemical shift anisotropy indicates an avenue to NMR structures of very large biological macromolecules in solution" PNAS 94:12366-71 (1997), which is incorporated by reference herein in its entirety.

As used herein, the term "chemical shift," in nuclear magnetic resonance (NMR) spectroscopy, refers to the resonant frequency of a nucleus relative to a standard or baseline. Some atomic nuclei possess a magnetic moment (nuclear spin), which gives rise to different energy levels and resonance frequencies in a magnetic field. The electron distribution of the same type of nucleus (e.g. $^1H$, $^{13}C$, $^{15}N$) usually varies according to the local geometry and with it the local magnetic field at each nucleus. This is reflected in the spin energy levels (and resonance frequencies). The variation of nuclear magnetic resonance frequencies of the same kind of nucleus, due to variations in the electron distribution, is called the chemical shift. The size of the chemical shift is typically given with respect to a reference frequency or reference sample usually a molecule with a barely distorted electron distribution. Typically, a $^1H$-$^{15}N$ HSQC spectrum is used to obtain chemical shift values. However, as provided in the methods herein, any NMR analysis method can be used.

As used herein, the term "chemical shift of an amino acid" includes the chemical shift of an element within the amino acid, e.g., H, C or N. As used herein, the term "element" refers to an atom distinguished by its atomic number, which is the number of protons in its nucleus. Exemplary elements include, but are not limited to, H (hydrogen), N (nitrogen) and C (carbon).

Exemplary chemical shift values for certain amino acids in the SENP1 polypeptide are shown in Table 3 and exemplary chemical shift values for certain amino acids in the SENP1 polypeptide when bound to SUMO are shown in Table 4. The sample conditions that correlate to the chemical shifts listed in Table 3 are 20 mM sodium phosphate, at pH 6.8 at 25° C. The sample conditions that correlate to the chemical shifts listed in Table 4 are 20 mM sodium phosphate and containing 150 mM NaCl, at pH 7, at 35° C. The values of the chemical shifts listed in Table 3 and Table 4 may vary by as much as 1 ppm for 41, and as much as 5 ppm for $^{15}N$ and $^{13}C$ due to differences in experimental conditions such as sample pH, temperature, addition of other components (e.g., salt), or amino acid substitutions in SENP1 and/or SUMO that may affect the function of SENP1 and/or SUMO. Thus, the chemical shifts listed in Tables 3 and 4 may vary from 1 ppm for $^1H$ and from 5 ppm for $^{15}N$ and $^{13}C$.

Thus, the peaks or chemical shifts in Tables 3 and 4 can be used by those of skill in the art to determine whether a test compound binds SENP1 by correlating experimental peaks or chemical shifts to those provided in Tables 3 and 4. For example, the peaks or chemical shifts obtained by NMR in the presence of a test compound can be compared to the corresponding peaks or chemical shifts in Tables 3 or 4 to determine whether the test compound binds SENP1. Thus, the chemical shift for an amino acid of SENP1 in Table 3 or 4 can be compared to the corresponding chemical shift obtained for the same amino acid in SENP1 in the presence of a test compound. When performing such comparisons, one of skill in the art will account for variances known to affect chemical shift values due to changes in experimental conditions, e.g., pH, temperature, addition of other components (e.g., salt), or amino acid substitutions. In some embodiments, detection of a change of greater than 5 ppm in the chemical shift for $^{15}N$ or $^{13}C$ of an amino acid of SENP1 or greater than 1 ppm in the chemical shift for $^1H$ of an amino acid of SENP1 indicates non-correlation of peaks. Optionally, the change is as compared to the corresponding chemical shift value for $^{15}N$, $^{13}C$, or $^1H$ of an amino acid of SENP1 in Table 3 or Table 4.

As used herein, the binding of a compound to SENP1 may be selective. The terms "selectively binds," "selectively binding," or "specifically binding" refers to the compound binding SENP1 to the partial or complete exclusion of other agents or compounds. By binding is meant a detectable binding, for example, binding above the background of the assay method. Optionally, detectable binding is evidenced by comparing baseline to experimental values, e.g., by comparing baseline NMR data (e.g., chemical shift values or digital resolution spectra) to experimental NMR data (e.g., chemical shift values or digital resolution spectra). Thus, binding can be determined by detecting changes or perturbations in an NMR measurement or spectrum for one sample, e.g., a control sample, compared to another or second sample, e.g., a sample containing a test compound. Detectable changes or perturbations in NMR signals include changes in location (chemical shift). General NMR techniques for proteins, including multidimensional NMR experiments and determination of protein-ligand interactions can be found in David G. Reid (ed.), Protein NMR Techniques, Humana Press, Totowa N.J. (1997). By way of example, detection of a perturbation or change includes detection of a difference in the chemical shift of SENP1 or SENP1-SUMO complex in the presence of a compound as compared to the chemical shift in the absence of the compound. The perturbation or change (whether increased or decreased) can include significant differences in an NMR measurement or spectrum (e.g., chemical shift) and can be greater than the experimental error or greater than the error bar range. For example, a change of at least about 1.1 times of the digital resolution of a spectrum or chemical shift for one or more amino acid residues of SENP1 in the presence of a compound can indicate the compound binds SENP1. Thus, a change of at least about 1.1, 1.2, 1.3, 1.4, 1.5, 2, 2.5, 3, 3.5, 4, 4.5, 5, 10, 20 times or more of the digital resolution of an NMR measurement or spectrum, e.g., chemical shift, observed in the presence of a compound as compared to a control can indicate the compound binds SENP1.

The terms greater, higher, increases, elevates, or elevation refer to increases above a control. The terms low, lower, reduces, or reduction refer to any decrease below control levels. For example, control levels are levels prior to, or in the absence of, addition of a compound.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 10 to about 100, about 20 to about 75, about 30 to about 50 amino acids or nucleotides in length. Optionally, the identity exists over a region that is at least about 50 amino acids in length, or more preferably over a region that is 100 to 500 or 1000 or more amino acids in length. The present invention includes polypeptides that are substantially identical to any of SEQ ID NOs:1, 2, 3, 4, 5, 6, or 7.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid residue in a polypeptide "corresponds" to or "is corresponding to" a given residue when it occupies the same essential structural position within the polypeptide as the given residue. For example, a selected residue in a comparison polypeptide corresponds to position 603 in a polypeptide provided herein (e.g., a SENP1 polypeptide), when the selected residue occupies the same essential spatial or structural relationship to position 603 as assessed using applicable methods in the art. For example, a comparison polypeptide may be aligned for maximum sequence homology with the polypeptide provided herein and the position in the aligned comparison polypeptide that aligns with position 603 may be determined to correspond to it. Alternatively, instead of (or in addition to) a primary sequence alignment as described above, a three dimensional structural alignment can also be used, e.g., where the structure of the comparison polypeptide is aligned for maximum correspondence with a polypeptide provided herein and the overall structures compared. In this case, an amino acid that occupies the same essential position as position 603 in the structural model may be said to correspond.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V);

6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The "active-site" of a protein or polypeptide refers to a protein domain that is structurally, functionally, or both structurally and functionally, active. For example, the active-site of a protein can be a site that catalyzes an enzymatic reaction, i.e., a catalytically active site. An active site refers to a domain that includes amino acid residues involved in binding of a substrate for the purpose of facilitating the enzymatic reaction. Optionally, the term active site refers to a protein domain that binds to another agent, molecule or polypeptide. For example, the active sites of SENP1 include sites on SENP1 that bind to or interact with SUMO. A protein may have one or more active-sites.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present application contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Other pharmaceutically acceptable carriers known to those of skill in the art are suitable for compositions of the present application.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a fluorescent label into a peptide specifically reactive with a target peptide (e.g., SENP1 polypeptide, SUMO protein or test compound). In embodiments, the label is a fluorescent label. Any method known in the art for conjugating a polypeptide to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide.

Methods

Provided herein are methods of detecting binding of an SENP1 polypeptide to a compound. The method includes the steps of contacting an SENP1 polypeptide with a compound, allowing the compound to bind to the SENP1 polypeptide, thereby forming a SENP1-compound complex, and detecting the SENP1-compound complex using nuclear magnetic resonance, thereby detecting binding of the SENP1 polypeptide to the compound.

A "compound" as provided herein refers to a polypeptide, protein, amino acid, small molecule or chemical compound that is capable of binding a SENP1 polypeptide or fragment thereof. In embodiments, the compound binds a SENP1 protein of SEQ ID NO:1, 2, 3, 4, 5, 6, or 7. In embodiments, the compound is a modulator of SENP1 activity. In embodiments, the compound is an inhibitor of SENP1 activity. In embodiments, the compound is an activator of SENP1 activity. In embodiments, the compound is a small molecule. A small molecule as provided herein include, but are not limited to the compounds in Tables 1 and 2 and those described in WO 2012/064887, which is incorporated by reference herein in its entirety. As used herein, the term "small molecule" refers to an organic compound containing carbon. A small molecule is generally, but not necessarily, of low molecular weight, e.g., less than 1000 Daltons.

A "test compound" as provided herein refers to a compound useful for the screening methods provided herein. A test compound may be capable of binding a SENP1 polypeptide or fragment thereof as provided herein. In embodiments, the test compound binds a SENP1 polypeptide or fragment thereof. In embodiments, the binding of the test compound to the SENP1 polypeptide or fragment thereof is detected by nuclear magnetic resonance. In embodiments, the test compound does not bind a SENP1 polypeptide or fragment thereof.

As defined herein, the term "inhibition", "inhibit", "inhibiting" and the like in reference to a compound or protein-inhibitor interaction means negatively affecting (e.g., decreasing) the activity or function of the protein (e.g. decreasing gene transcription or translation) relative to the activity or function of the protein in the absence of the inhibitor. In embodiments, inhibition refers to reduction of a disease or symptoms of disease (e.g., cancer). In embodiments, inhibition refers to a reduction in the activity of an enzymatic activity (e.g., SENP activity). In embodiments, inhibition refers to a reduction in the activity of a signal transduction pathway or signaling pathway (e.g. cell cycle). Thus, inhibition includes, at least in part, partially or totally blocking stimulation, decreasing, preventing, or delaying activation, or inactivating, desensitizing, or down-regulating transcription, translation, signal transduction or enzymatic activity or the amount of a protein (e.g. a cellular protein or a viral protein). In embodiments, inhibition refers to inhibition of SENP1.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA), compound or small molecule that inhibits cellular function (e.g., replication) e.g., by binding, partially or totally blocking stimulation, decrease, prevent, or delay activation, or inactivate, desensitize, or down-regulate signal transduction, gene expression or enzymatic activity necessary for protein activity. Inhibition as provided herein may also include decreasing or blocking a protein activity (e.g., activity of SENP1).

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

Optionally, the compound is a small molecule. Optionally, the step of detecting includes detecting a perturbation in the presence of the compound relative to the absence of the compound. For example, binding of a compound to SENP1 is detected if a perturbation is detected in an NMR measurement or spectrum in the presence of the compound as compared to or relative to the absence of the compound. Optionally, the step of detecting includes determining a chemical shift for an amino acid in an active site of the SENP1 polypeptide. Binding is detected by a change in the chemical shift in the presence of the compound relative to the corresponding chemical shift in the absence of the compound. Optionally, the active site is a catalytically active site. Optionally, the active site is a site involved in SUMO binding, e.g., the active site is a site on SENP1 that binds to the SUMO protein. Thus, the step of detecting includes determining a chemical shift for an amino acid involved in binding of SENP1 polypeptide to SUMO. Optionally, the chemical shift is determined for one or more amino acids of SEQ ID NOs:3, 4, 5, 6 or 7.

Optionally, the chemical shift is determined for one or more amino acid residues selected from the group consisting of D550, H533, C603, W465, W534, L466, G531, C535, M552, G554, E469 and Q596 of SEQ ID NO:1.

In embodiments, the change is a change in the chemical shift of amino acid residue D550, H533, C603, W465, W534, L466, G531, C535, M552, G554, E469 or Q596 of SEQ ID NO:1. In embodiments, the change is a change in the chemical shift of amino acid residue D550, H533, C603, W465, W534, L466, G531, C535, M552, G554, E469 and Q596 of SEQ ID NO:1. In embodiments, the change is a change in the chemical shift of amino acid residue D550 of SEQ ID NO:1. In embodiments, the change is a change in the chemical shift of amino acid residue H533 of SEQ ID NO:1. In embodiments, the change is a change in the chemical shift of amino acid residue C603 of SEQ ID NO:1. In embodiments, the change is a change in the chemical shift of amino acid residue W465 of SEQ ID NO:1. In embodiments, the change is a change in the chemical shift of amino acid residue W534 of SEQ ID NO:1. In embodiments, the change is a change in the chemical shift of amino acid residue L466 of SEQ ID NO:1. In embodiments, the change is a change in the chemical shift of amino acid residue G531 of SEQ ID NO:1. In embodiments, the change is a change in the chemical shift of amino acid residue C535 of SEQ ID NO:1. In embodiments, the change is a change in the chemical shift of amino acid residue M552 of SEQ ID NO:1. In embodiments, the change is a change in the chemical shift of amino acid residue G554 of SEQ ID NO:1. In embodiments, the change is a change in the chemical shift of amino acid residue E469 of SEQ ID NO:1. In embodiments, the change is a change in the chemical shift of amino acid residue Q596 of SEQ ID NO:1.

In embodiments, the change is a change in the chemical shift of an amino acid residue corresponding to D550, H533, C603, W465, W534, L466, G531, C535, M552, G554, E469 or Q596 of SEQ ID NO:1. In embodiments, the change is a change in the chemical shift of an amino acid residue corresponding to D550, H533, C603, W465, W534, L466, G531, C535, M552, G554, E469 and Q596 of SEQ ID NO:1. In embodiments, the change is a change in the chemical shift of an amino acid residue corresponding to D550 of SEQ ID NO:1. In embodiments, the change is a change in the chemical shift of an amino acid residue corresponding to H533 of SEQ ID NO:1. In embodiments, the change is a change in the chemical shift of an amino acid residue corresponding to C603 of SEQ ID NO:1. In embodiments, the change is a change in the chemical shift of an amino acid residue corresponding to W465 of SEQ ID NO:1. In embodiments, the change is a change in the chemical shift of an amino acid residue corresponding to W534 of SEQ ID NO:1. In embodiments, the change is a change in the chemical shift of an amino acid residue corresponding to L466 of SEQ ID NO:1. In embodiments, the change is a change in the chemical shift of an amino acid residue corresponding to G531 of SEQ ID NO:1. In embodiments, the change is a change in the chemical shift of an amino acid residue corresponding to C535 of SEQ ID NO:1. In embodiments, the change is a change in the chemical shift of an amino acid residue corresponding to M552 of SEQ ID NO:1. In embodiments, the change is a change in the chemical shift of an amino acid residue corresponding to G554 of SEQ ID NO:1. In embodiments, the change is a change in the chemical shift of an amino acid residue corresponding to E469 of SEQ ID NO:1. In embodiments, the change is a change in the chemical shift of an amino acid residue corresponding to Q596 of SEQ ID NO:1.

In embodiments, the SENP1 polypeptide includes amino acid residue 603 of SEQ ID NO:1. In embodiments, the SENP1 polypeptide includes an amino acid residue corresponding to amino acid residue 603 of SEQ ID NO:1. In embodiments, the SENP1 polypeptide includes amino acid residue 550 of SEQ ID NO:1. In embodiments, the SENP1 polypeptide includes an amino acid residue corresponding to amino acid residue 550 of SEQ ID NO:1. In embodiments, the SENP1 polypeptide includes amino acid residue 533 of SEQ ID NO:1. In embodiments, the SENP1 polypeptide includes an amino acid residue corresponding to amino acid residue 533 of SEQ ID NO:1. In embodiments, the SENP1 polypeptide includes amino acid residue 465 of SEQ ID NO:1. In embodiments, the SENP1 polypeptide includes an amino acid residue corresponding to amino acid residue 465 of SEQ ID NO:1. In embodiments, the SENP1 polypeptide includes amino acid residue 534 of SEQ ID NO:1. In embodiments, the SENP1 polypeptide includes an amino acid residue corresponding to amino acid residue 534 of SEQ ID NO:1. In embodiments, the SENP1 polypeptide includes amino acid residue 466 of SEQ ID NO:1. In embodiments, the SENP1 polypeptide includes an amino acid residue corresponding to amino acid residue 466 of SEQ ID NO:1. In embodiments, the SENP1 polypeptide includes amino acid residue 531 of SEQ ID NO:1. In embodiments, the SENP1 polypeptide includes an amino acid residue corresponding to amino acid residue 531 of SEQ ID NO:1. In embodiments, the SENP1 polypeptide includes amino acid residue 535 of SEQ ID NO:1. In embodiments, the SENP1 polypeptide includes an amino acid residue corresponding to amino acid residue 535 of SEQ ID NO:1. In embodiments, the SENP1 polypeptide includes amino acid residue 552 of SEQ ID NO:1. In embodiments, the SENP1 polypeptide includes an amino acid residue corresponding to amino acid residue 552 of SEQ ID NO:1. In embodiments, the SENP1 polypeptide includes amino acid residue 554 of SEQ ID NO:1. In embodiments, the SENP1 polypeptide includes an amino acid residue corresponding to amino acid residue 554 of SEQ ID NO:1. In embodiments, the SENP1 polypeptide includes amino acid residue 469 of SEQ ID NO:1. In embodiments, the SENP1 polypeptide includes an amino acid residue corresponding to amino acid residue 469 of SEQ ID NO:1. In embodiments, the SENP1 polypeptide includes amino acid residue 596 of SEQ ID NO:1. In embodiments, the SENP1 polypeptide includes an amino acid residue corresponding to amino acid residue 596 of SEQ ID NO:1.

Optionally, the chemical shift is determined for a mutation at amino acid residue 603 of SEQ ID NO:1. Optionally, the mutation is C603S. Optionally, the chemical shift is determined for one or more amino acid residues 440-455, 463-473, 493-515, 529-535, 550-554, or 596-603 of SEQ ID NO:1. Optionally, the SENP1 polypeptide or SENP1-compound complex is bound to a SUMO protein thereby forming a SENP1-SUMO complex or SENP1-SUMO-compound complex. Optionally, the SUMO protein is a truncated SUMO protein. Optionally, the compound does not interact with C603 of SEQ ID NO:1 of SENP1, e.g., the compound does not covalently modify C603 of SENP1. Thus, the provided methods optionally include detecting binding by producing an NMR spectra of the SENP-1 compound complex and identifying a change in the NMR spectra relative to the absence of the compound. Optionally, the change is a change in the chemical shift of an amino acid of SEQ ID NOs:3, 4, 5, 6 or 7. Optionally, the change is a change in the chemical shift of an amino acid selected from the group consisting of D550, H533, C603, W465, W534, L466, G531, C535, M552, G554, E469 and Q596. Optionally, the change is a change in the chemical shift of the amino acid S603. Optionally, the change is a change in the chemical shift of an amino acid residue 440-455, 463-473, 493-515, 529-535, 550-554, or 596-603 of SEQ ID NO:1.

Also provided is a method of screening for compounds that bind SENP1 including the steps of providing a first sample comprising SENP1 or an SENP1-SUMO complex, determining an NMR spectra of the first sample, providing a second sample comprising an SENP1-compound complex or an SENP1-SUMO-compound complex, and determining an NMR spectra of the second sample. Detection of a change in the NMR spectra in the second sample as compared to the first sample indicates the compound binds SENP1.

Provided are methods of screening for an inhibitor of SENP1. The methods include contacting a composition comprising an SENP1 polypeptide with a test compound and detecting whether the test compound binds the SENP1 polypeptide or fragment thereof by nuclear magnetic resonance.

Optionally, the step of detecting includes detecting a perturbation in the presence of the compound relative to the absence of the compound. For example, the test compound binds or inhibits SENP1 if a perturbation is detected in an NMR measurement or spectrum in the presence of the compound as compared to or relative to the absence of the compound. Optionally, the step of detecting comprises determining a chemical shift for one or more amino acids in the active site of the SENP1 polypeptide. The chemical shift in the presence of the compound will be changed relative to the corresponding chemical shift in the absence of the test compound if the test compound binds to SENP1. Optionally, the active site is a catalytically active site. Optionally, the active site is a site involved in SUMO binding, e.g., the active site is a site on SENP1 that binds to the SUMO protein. Thus, the step of detecting includes determining a chemical shift for an amino acid involved in binding of SENP1 polypeptide to SUMO. Optionally, the chemical shift is determined for one or more amino acids of SEQ ID NOs:3, 4, 5, 6 OR 7. Optionally, the chemical shift is determined for one or more amino acid residues selected from the group consisting of D550, H533, C603, W465, W534, L466, G531, C535, M552, G554, E469 and Q596 of SEQ ID NO:1. Optionally, the chemical shift is determined for a mutation at amino acid residue 603 of SEQ ID NO:1. Optionally, the mutation is C603S. Optionally, the chemical shift is determined for one or more amino acid residues 440-455, 463-473, 493-515, 529-535, 550-554, or 596-603 of SEQ ID NO:1. Optionally, the SENP1 polypeptide is bound to a SUMO protein thereby forming a SENP1-SUMO complex. Optionally, the SUMO protein is a truncated SUMO protein. Optionally, the composition comprising the SENP1 polypeptide or SENP1-SUMO complex is an aqueous solution. Optionally, the composition is at a pH from about 6.0 to about 7.5. Optionally, the pH is about 6.8. Optionally, the composition comprises a buffering agent, a reducing agent, a base or combinations thereof. Optionally, the composition comprises sodium phosphate, $D_2O$, sodium azide, dithiothreitol or combinations thereof. The sodium phosphate can be present at about 20 mM. Optionally, the compound to be tested is a small molecule. Optionally, the compound does not interact with C603 numbered relative to SEQ ID NO:1 of SENP1, e.g., the compound does not covalently modify C603 of SENP1. Optionally, in the provided methods, the SENP1 binds the compound forming an SENP1-compound complex and the detecting comprises producing an NMR spectra of the SENP1-compound complex and identifying a change in the NMR spectra relative to the absence of the compound. Optionally, the change is a change in the chemical shift of an amino acid of SEQ ID NOs:3, 4, 5, 6 or 7. Optionally, the change is a change in the chemical shift of an amino acid selected from the group consisting of D550, H533, C603, W465, W534, L466, G531, C535, M552, G554, E469 and Q596. Optionally, the change is a change in the chemical shift of the amino acid S603. Optionally, the change is a change in the chemical shift of an amino acid residue 440-455, 463-473, 493-515, 529-535, 550-554, or 596-603 of SEQ ID NO:1. Optionally, the change is a change in the chemical shift of an amino acid in the active site of SENP1. Optionally, the active site is a catalytically active site or a site that binds to the SUMO protein.

Also provided are methods of identifying an SENP1 inhibitor that include combining an SENP1 polypeptide, a SUMO protein, and a test compound in a reaction vessel, allowing the SENP1 polypeptide, SUMO protein and test compound to form a SENP1-SUMO-compound complex, and detecting the SENP1-SUMO-compound complex thereby identifying the compound as a SENP1 inhibitor. A "reaction vessel" as provided herein refers to a vial, tube, flask, bottle, syringe or other container means, into which the SENP1 polypeptide, SUMO protein and test compound are combined to allow the formation of a SENP1-SUMO-compound complex.

Optionally, one or more of the SENP1 polypeptide, SUMO protein or test compound is labeled. Optionally, the label is a fluorescent label. Optionally, the test compound comprises a fluorescent label. Optionally, the SUMO is a truncated SUMO protein. Optionally, the SUMO comprises amino acid residues 1-92 of the SUMO protein. Optionally, the SUMO protein comprises SEQ ID NO:8 or SEQ ID NO:9. Optionally, the SENP1 polypeptide comprises SEQ ID NOs:1, 2, 3, 4, 5, 6, or 7. Optionally, the SENP1 polypeptide comprises amino acid residue 603 of SEQ ID NO:1. Optionally, the SENP1 polypeptide comprises a mutation at amino acid residue 603 of SEQ ID NO:1. Optionally, the mutation is C603S. Optionally, the SENP1 polypeptide comprises amino acid residues 440-455, 463-473, 493-515, 529-535, 550-554, or 596-603 of SEQ ID NO:1. Optionally, the test compound is a small molecule. In the provided methods, the detecting can be performed by a variety of methods known to those skilled in the art and described in the example below. See, e.g., Protein-Ligand Interactions, Vol. 1008, Methods in Molecular Biology, Humana Press, Inc., Clifton, N.J., Williams and Daviter, Eds. (2013). For example, a wide variety of assays for detecting binding can be used including labeled in vitro protein-ligand binding assays, cell based assays, immunoassays, and the like. Optionally, detecting can be performed using solution-phase binding assays, e.g., fluorescent polarization. Thus, binding can be detected by fluorescent polarization (Rossi et al., *Nat. Protoc.* 6(3):365-87 (2011)). Optionally, binding is detected by detecting a change in the thermal properties of SENP1, e.g., the thermal property can be the melting temperature of SENP1. In some embodiments, the detecting is performed using nuclear magnetic resonance. Optionally, the detecting comprises producing an NMR spectra of the SENP1-SUMO-compound complex and identifying a change in the NMR spectra relative to the absence of the test compound. Optionally, the change is a change in the chemical shift of an amino acid in an active site of the SENP1 polypeptide. The active site can be, for example, a catalytically active site or a site that binds to the SUMO protein. Optionally, the amino acid is an amino acid of SEQ ID NOs:3, 4, 5, 6 OR 7. Optionally, the amino acid is selected from the group consisting of D550, H533, C603, W465, W534, L466, G531, C535, M552, G554, E469 and Q596. Optionally, the amino acid is S603. Optionally, the amino acid is amino acid residue 440-455, 463-473, 493-515, 529-535, 550-554, or 596-603 of SEQ ID NO:1.

As used throughout, the term "SENP1 polypeptide" refers to full length SENP1 and fragments thereof. The sequence and structure of the SENP1 polypeptide is known. (See above and Protein Data Bank (PDB) accession codes 2IYC and 2IY1; Shen et al., Nat. Struct. Mol. Biol. 13(12):1069-1077 (2006); and Xu et al., *Biochem. J.* 398(3):345-52 (2006)). Optionally, the SENP1 polypeptide comprises SEQ ID NOs:1, 2, 3, 4, 5, 6, or 7. Optionally, the SENP1 polypeptide comprises amino acid residue 603 of SEQ ID NO:1. Optionally, the SENP1 polypeptide comprises a mutation at amino acid residue 603 of SEQ ID NO:1. Optionally, the mutation is C603S. Optionally, the SENP1 polypeptide comprises amino acid residues 440-455, 463-473, 493-515, 529-535, 550-554, or 596-603 of SEQ ID NO:1.

Optionally, in the provided methods, SENP1 is bound to SUMO or a fragment thereof, e.g., a truncated SUMO protein. Thus, optionally, the SENP1 is bound to a SUMO protein thereby forming a SENP1-SUMO complex. Optionally, the SUMO protein is a truncated SUMO protein. Optionally, the SUMO protein is SEQ ID NO:8 or 9. As used herein, the term "truncated SUMO protein" refers to a SUMO protein or polypeptide that has been manipulated to remove at least one amino acid residue relative to wild-type SUMO, e.g., a SUMO protein or polypeptide that occurs in nature. Exemplary wild-type SUMO proteins include, but are not limited to, SEQ ID NO:9 and those found at GenBank Accession Nos. AAC50996.1, NP_008868.3, NP_001005849.1, P55854.2, and NP_008867.2. Truncated SUMO proteins include, but are not limited to, SEQ ID NO:8. As used herein, the term "SUMO" refers to SUMO1, SUMO2, or SUMO3 or fragments thereof or complexes thereof, e.g., SUMO2/3. The nucleic acid and amino acid sequences for SUMO are known. See, for example, Hay, Mol. Cell 18(1):1-12 (2005); and Yeh, et al., J. Biol. Chem., 284(13):8223-7 (2009). For example, nucleic acid and amino acid sequences for SUMO-1 can be found at GenBank Accession Nos. U67122.1 and AAC50996.1. Nucleic acid and amino acid sequences for SUMO-2 can be found at GenBank Accession Nos. NM_006937.3, NM_001005849.1, NP_008868.3 and NP_001005849.1. Nucleic acid and amino acid sequences for SUMO-3 can be found at GenBank Accession Nos. NM_006936.2, P55854.2, and NP_008867.2. Optionally, the SENP1 is bound to SUMO1 to form an SENP1-SUMO1 complex.

The provided SENP1 polypeptides and/or SUMO polypeptides and fragments thereof may contain one or more modifications, e.g., a conservative modification. As used herein, the term "modification" refers to a modification in a nucleic acid sequence of a gene or an amino acid sequence. Modifications include, but are not limited to, insertions, substitutions and deletions. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Amino acid substitutions are typically of single residues, but can occur at a number of different locations at once. Substitutions, deletions, insertions or any combination thereof may be combined to arrive at a final construct. Substitutional modifications are those in which at least one residue has been removed and a different residue inserted in its place.

Modifications are generated using any number of methods known in the art. For example, site directed mutagenesis can be used to modify a nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated in the newly synthesized strand. See, for example, Kunkel, 1985, Proc. Natl. Acad. Sci. USA, 82:488; Kunkel et al., 1987, Meth. Enzymol., 154:367; Lewis & Thompson, 1990, Nucl. Acids Res., 18:3439; Bohnsack, 1996, Meth. Mol. Biol., 57:1; Deng & Nickoloff, 1992, Anal. Biochem., 200:81; and Shimada, 1996, Meth. Mol. Biol., 57:157. Other methods are routinely used in the art to introduce a modification into a sequence. For example, modified nucleic acids are generated using PCR or chemical synthesis, or polypeptides having the desired change in amino acid sequence can be chemically synthesized. See, for example, Bang & Kent, 2005, Proc. Natl. Acad. Sci. USA, 102:5014-9 and references therein.

Also provided herein are nucleic acids encoding the polypeptides described throughout. It is understood that the nucleic acids that can encode those peptide, polypeptide, or protein sequences, variants and fragments thereof are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequence.

Provided herein are compounds to be tested for their ability to bind and/or inhibit SENP1. As used herein, an inhibitor refers to an agent or compound that inhibits SENP1 directly or indirectly. For example, an inhibitor of SENP1 can inhibit the expression or activity of SENP1. Compounds to be tested in the provided methods include, but are not limited to, small molecules, peptides, nucleic acids and antibodies. Optionally, the compound to be tested is a small molecule. Optionally, the small molecule is an inhibitor of SENP1. Small molecule inhibitors of SENP1 include, but are not limited to the compounds in Tables 1 and 2 and those described in WO 2012/064887, which is incorporated by reference herein in its entirety. As used herein, the term "small molecule" refers to an organic compound containing carbon. A small molecule is generally, but not necessarily, of low molecular weight, e.g., less than 1000 Daltons.

Once a compound has been identified as binding to SENP1 and/or inhibiting SENP1, the compound can be further tested for its binding and/or inhibitory abilities using a variety of known methods including the methods described in the example below. Various assays for determining levels and activities of protein are available, such as amplification/expression methods, immunohistochemistry methods, FISH and shed antigen assays, southern blotting, or PCR techniques. Moreover, the protein expression or amplification may be evaluated using in vivo diagnostic assays.

Compositions and Apparatuses for NMR Analysis

Provided herein are compositions comprising a SENP1 polypeptide and NMR apparatuses comprising the compositions for NMR analysis. Optionally, the composition is an aqueous solution. Optionally, the aqueous solution comprises an SENP1 polypeptide at a pH from about 6.0 to about 7.5. For example, the pH can be about 6.8. The provided compositions or aqueous solutions can further include, for example, buffering agents, reducing agents, solvents, bases and combinations thereof. Buffering agents include, but are not limited to, phosphate or citrate buffers. Reducing agents include but are not limited to, dithiothreitol, and sodium borohydride. Bases include, but are not limited to, metal oxides and salts of carbanions, amides and hydrides. Solvents include, but are not limited to, dimethyl sulfoxide (DMSO) Optionally, the compositions can include sodium phosphate, DMSO, $D_2O$, sodium azide, dithiothreitol or combinations thereof. By way of example, the sodium phosphate can be present at about 20 mM. Optionally, the SENP1 polypeptide is bound to a SUMO protein thereby forming a SENP1-SUMO complex. Optionally, the SENP1 polypeptide is bound to a compound thereby forming a SENP1-compound complex. Optionally, the SENP1 polypeptide is bound to a SUMO protein thereby forming a SENP1-SUMO-compound complex. Optionally, the SUMO protein is a truncated SUMO protein. Optionally, the SENP1 polypeptide comprises SEQ ID NO:1, 2, 3, 4, 5, 6, or 7. Optionally, the SENP1 polypeptide comprises amino acid residues 440-455, 463-473, 493-515, 529-535, 550-554, or 596-603 numbered relative to SEQ ID NO:1.

An NMR apparatus comprising an NMR sample container for NMR analysis, said NMR sample container comprising the aqueous composition or solution is also provided. NMR apparatuses are known and can be obtained from commercially available sources. Makers of NMR equipment include, but are not limited to, Bruker (Germany), Oxford Instruments (United Kingdom), General Electric (Fairfield, Conn.), Philips (Amsterdam, Netherlands), Siemens AG (Munich, Germany) and Agilent Technologies, Inc. (Santa Clara, Calif.).

Compositions

Provided herein are compositions including the inhibitors identified by the screening and binding methods provided herein. The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy*, 21$^{st}$ Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The inhibitors are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Thus, the compositions are administered in a number of ways depending on whether local or systemic treatment is desired, and on the area to be treated.

The compositions for administration will commonly comprise an agent as described herein (e.g. inhibitor of SENP1) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the modified viruses can be prepared by mixing the modified adenovirus (or one or more nucleic acids encoding the modified adenovirus) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e. g. Zn-protein complexes); and/or non-ionic surfactants. The modified adenovirus (or one or more nucleic acids encoding the modified adenovirus) can be formulated at any appropriate concentration of infectious units.

Formulations suitable for oral administration can consist of (a) liquid solutions, such as an effective amount of the modified adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The inhibitors of SENP1 can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation is preferably in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

Methods of Treatment

The provided inhibitors of SENP1 can be administered for therapeutic or prophylactic treatments or used in the laboratory. Thus, provided is a method of treating a proliferative disorder in a subject. The method includes administering the provided inhibitors of SENP1 or compositions to the subject. As described throughout, the pharmaceutical composition is administered in any number of ways including, but not limited to, intravenously, intravascularly, intrathecally, intramuscularly, subcutaneously, intraperitoneally, or orally. Optionally, the method further comprising administering to the subject one or more additional therapeutic agents. Optionally, the therapeutic agent is a chemotherapeutic agent.

As described throughout, the proliferative disorder can be cancer. Optionally, the proliferative disorder is selected from the group consisting of lung cancer, prostate cancer, colorectal cancer, breast cancer, thyroid cancer, renal cancer, liver cancer and leukemia. Optionally, the proliferative disorder is metastatic.

In therapeutic applications, compositions are administered to a subject suffering from a proliferative disease or disorder (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus the methods are applicable to both human therapy and veterinary applications.

Optionally, the provided methods include administering to the subject one or more additional therapeutic agents. Thus, the provided methods can be combined with other cancer therapies, radiation therapy, hormone therapy, or chemotherapy. The combined administrations contemplates coadministration, using separate formulations or a single pharmaceutical formulation, and consecutive administration in either order, wherein preferably there is a time period while both (or all) active agents simultaneously exert their biological activities. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

According to the methods provided herein, the subject is administered an effective amount of one or more of the agents provided herein. The terms effective amount and effective dosage are used interchangeably. The term effective amount is defined as any amount necessary to produce a desired physiologic response (e.g., killing of a cancer cell). The dosages, however, may be varied depending upon the requirements of the subject, the severity of the condition being treated, and the compound being employed. For example, dosages can be empirically determined considering the type and stage of cancer diagnosed in a particular subject. The dose administered to a subject, in the context of the provided methods should be sufficient to affect a beneficial therapeutic response in the patient over time. Determination of the proper dosage for a particular situation is within the skill of the practitioner. Thus, effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Kits

Provided herein are kits for screening for compounds that bind or inhibit SENP1. The kits include a composition comprising an SENP1 polypeptide. Optionally, the composition is an aqueous solution. Optionally, the SENP1 polypeptide comprises SEQ ID NO:1, 2, 3, 4, 5, 6, or 7. Optionally, the SENP1 polypeptide comprises amino acid residues 440-455, 463-473, 493-515, 529-535, 550-554, or 596-603 numbered relative to SEQ ID NO:1. Optionally, the aqueous composition comprising an SENP1 polypeptide is at a pH from about 6.0 to about 7.5. Optionally, the pH is about 6.8. Optionally, the compositions can further include, for example, buffering agents, reducing agents, bases and combinations thereof. Optionally, the compositions can include sodium phosphate, $D_2O$, sodium azide, dithiothreitol or combinations thereof. By way of example, the sodium phosphate can be present at about 20 mM. Optionally, the SENP1 polypeptide is bound to a SUMO protein thereby forming a SENP1-SUMO complex. Optionally, the SENP1 polypeptide or SENP1-SUMO complex is bound to a compound thereby forming a SENP1-compound complex or SENP1-SUMO-compound complex. Optionally, the SUMO protein is a truncated SUMO protein. In some embodiments, the kit comprises a container including a SENP1 polypeptide or SENP1-SUMO complex and, optionally, a second container including a SENP1-compound complex or SENP-SUMO-compound complex.

Further provided are kits including an inhibitor of SENP1. Optionally, the kit comprises one or more doses of an effective amount of a composition comprising a SENP1 inhibitor. Optionally, the composition is present in a container (e.g., vial or packet). Optionally, the kit further includes one or more additional therapeutic agents. Optionally, the therapeutic agent is a chemotherapeutic agent. Optionally, the kit comprises a means of administering the composition, such as, for example, a syringe, needle, tubing, catheter, patch, and the like. The kit may also comprise formulations and/or materials requiring sterilization and/or dilution prior to use.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLE

Example 1. Identification and Characterization of a SENP Inhibitors

Enzymes called SENPs catalyze both the maturation of small ubiquitin-like modifier (SUMO) precursors and removal of SUMO modifications, which regulate essential cellular functions such as cell cycle progression, DNA damage response and intracellular trafficking. Some members, such as SENP1, are potential targets for developing cancer therapeutics. A search for small molecule inhibitors of SENPs was carried out using in-silico screening in conjunction with biochemical assays, and a new chemotype of small molecule inhibitors that non-covalently inhibit SENPs was identified. The inhibitors confer the non-competitive inhibitory mechanism, as shown by nuclear magnetic resonance (NMR) and quantitative enzyme kinetic analysis. The NMR data also provided evidence for substrate-assisted inhibitor binding, which indicates the need for caution in using artificial substrates for compound screening, as the inhibitory effects could be significantly different from using the physiological substrates.

In this study, it was purported to identify small molecule inhibitors of SENPs through in-silico screening in conjunction with enzyme kinetic, nuclear magnetic resonance (NMR) and cellular analyses. In silico screening was performed using Protein Data Bank (PDB) accession codes 2IYC and 2IY1 and by considering hydrogen bonding and hydrophobic interactions between the C-terminus of full-length SUMO-1 and SENP1. The GLIDE program (Friesner et al., *Journal of Medicinal Chemistry* 47:1739-1749 (2004)) was used to search the 250,000 compound library provided by the Developmental Therapeutics Program (DTP) of the National Cancer Institute, using the E-model scoring function of Cvdw, which is the sum of the van der Waals (Evdw) and electrostatic interaction energy terms (Eelec). Among the top hits, the dominant scaffolds were peptidomimetics and compounds that contained 2-fold symmetry. Forty compounds (100 µM) representing the dominant scaffolds were tested for their inhibitory effects on SENP1 and SENP2 for maturation of SUMO-1 and SUMO-2 precursors. The most potent compounds contained sulfonyl-benzene groups. Additional analogues of this group were obtained from DTP, and NSC5068, hereafter referred to as SPI-01 (SUMO protease inhibitor), was found to have the highest potency (Table 1). Available analogs of SPI-01 were obtained from DTP. Five compounds in this group (Table 1, SPI-06 to SPI-10) are "half" of the other compounds (Table 1, SPI-01 to SPI-05) and allowed the exploration of the activity requirements of the two-fold symmetric structure of SPI-01 to SPI-05. The inhibitory activity of these compounds on SENP1 and SENP2 was characterized using substrates that contained precursor SUMO-1 or SUMO-2 (S) flanked by yellow fluorescent protein (Y) at the N-terminus and enhanced cyan fluorescent protein (E) at the C-terminus (YSE) (Tatham and Hay, *Methods Mol. Biol.* 497:253-268 (2009)). Although the cleavage of the substrates can be detected by fluorescence resonance energy transfer (FRET), FRET could not be used because many of these compounds interfere with the FRET signal. Therefore, a gel-based assay was used to determine the inhibitory effects of all compounds on SENP1 and 2 (representative data shown in FIGS. 1 and 2), and the gel bands were quantified to determine the half maximum inhibitory concentrations ($IC_{50}$) (Table 1). The inhibitory effects of the compounds on the endopeptidase activities were not only enzyme-dependent, but also substrate-dependent. For SENP1-mediated cleavage of SUMO-1 precursor, only four of the compounds (SPI-01 to SPI-04) had half maximal inhibitory concentrations ($IC_{50}$) below 60 µM. The inhibitors were more potent for inhibiting SENP2 than SENP1 for cleavage of the SUMO-1 precursor. However, for cleavage of the SUMO-2 precursor, some compounds (i.e. SPI-01 and SPI-04) had similar potency for inhibiting SENP1 and SENP2, while others (i.e. SPI-07 and SPI-10) were more potent for inhibiting SENP1 than SENP2 or vice versa (i.e. SPI-06 and SPI-09) (Table 1). In addition to the differential effects on SENP1 and SENP2, SPI-01 had more than 10 fold less potency for inhibiting a de-ubiquitin enzyme isopeptidase T than inhibiting SENP2.

TABLE 1

Effect of inhibitors on inhibition of the maturation of SUMO precursors by SENP1 and SENP2.

| Compounds | | | IC$_{50}$ (µM)-SUMO1 | | IC$_{50}$ (µM)-SUMO2 | |
| --- | --- | --- | --- | --- | --- | --- |
| Structure | Code[†] | NCI ID[‡] | SENP1 | SENP2 | SENP1 | SENP2 |
| | SPI-01 | NSC5068 | 32.8 ± 1.82 | 1.42 ± 3.0 | 1.88 ± 2.2 | 1.1 ± 5.8 |
| | SPI-02 | NSC16224 | 26.5 ± 1.86 | 3.42 ± 1.6 | 2.08 ± 2.0 | 2.70 ± 2.1 |
| | SPI-03 | NSC8676 | 20.27 ± 2.47 | 5.17 ± 1.32 | 1.86 ± 2.3 | 3.0 ± 2.0 |
| | SPI-04 | NSC34933 | 11.2 ± 1.7 | 1.6 ± 2.5 | 2.32 ± 2.6 | 2.15 ± 2.28 |
| | SPI-05 | NSC5067 | >60 | 19.7 ± 1.47 | 7.5 ± 1.6 | 4.6 ± 1.65 |
| | SPI-06 | NSC70551 | >60 | 3.62 ± 1.98 | 4.32 ± 2.2 | 10.7 ± 1.6 |

TABLE 1-continued

Effect of inhibitors on inhibition of the maturation of SUMO precursors by SENP1 and SENP2.

| Compounds | | | IC$_{50}$ (µM)-SUMO1 | | IC$_{50}$ (µM)-SUMO2 | |
|---|---|---|---|---|---|---|
| Structure | Code† | NCI ID‡ | SENP1 | SENP2 | SENP1 | SENP2 |
| [structure] | SPI-07 | NSC58046 | >60 | >60 | 17.54 ± 4.9 | 28.06 ± 9.2 |
| [structure] | SPI-08 | NSC22940 | >60 | 4.1 ± 3.0 | >60 | 41.06 ± 5.2 |
| [structure] | SPI-09 | NSC42164 | >60 | 23.6 ± 1.6 | >60 | 26.6 ± 2.5 |
| [structure] | SPI-10 | NSC45551 | >60 | 34.21 ± 1.9 | 11.1 ± 3.7 | 36.44 ± 5.7 |

Figure 3A:
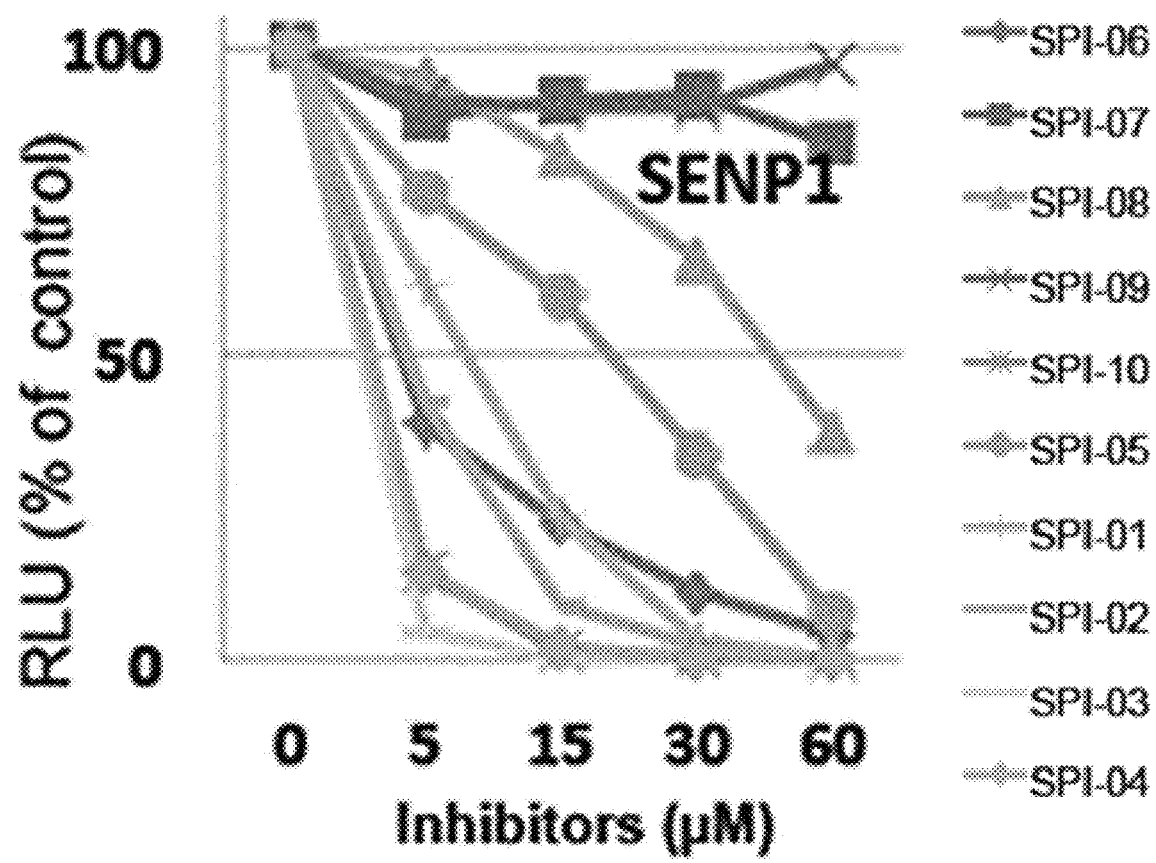
FIGS. 3A-3C are graphs showing the effects of the panel of inhibitors shown in Table 1 at inhibiting SENP1, 2 and 7. In 96-well plates, SENPs (50-200 nM) were pre-treated with increasing concentrations of each compound, after which DUB-Glo (40 µM final concentration; Promega, Madison, Wis.) was added as substrate. Experiments were performed in triplicate. The amount of cleaved product is proportional to the relative light unit (RLU), which is bioluminescence produced by luciferase catalyzed reaction of luciferin that was produced by SENP cleavage of DUB-Glo.
Figure 3B:
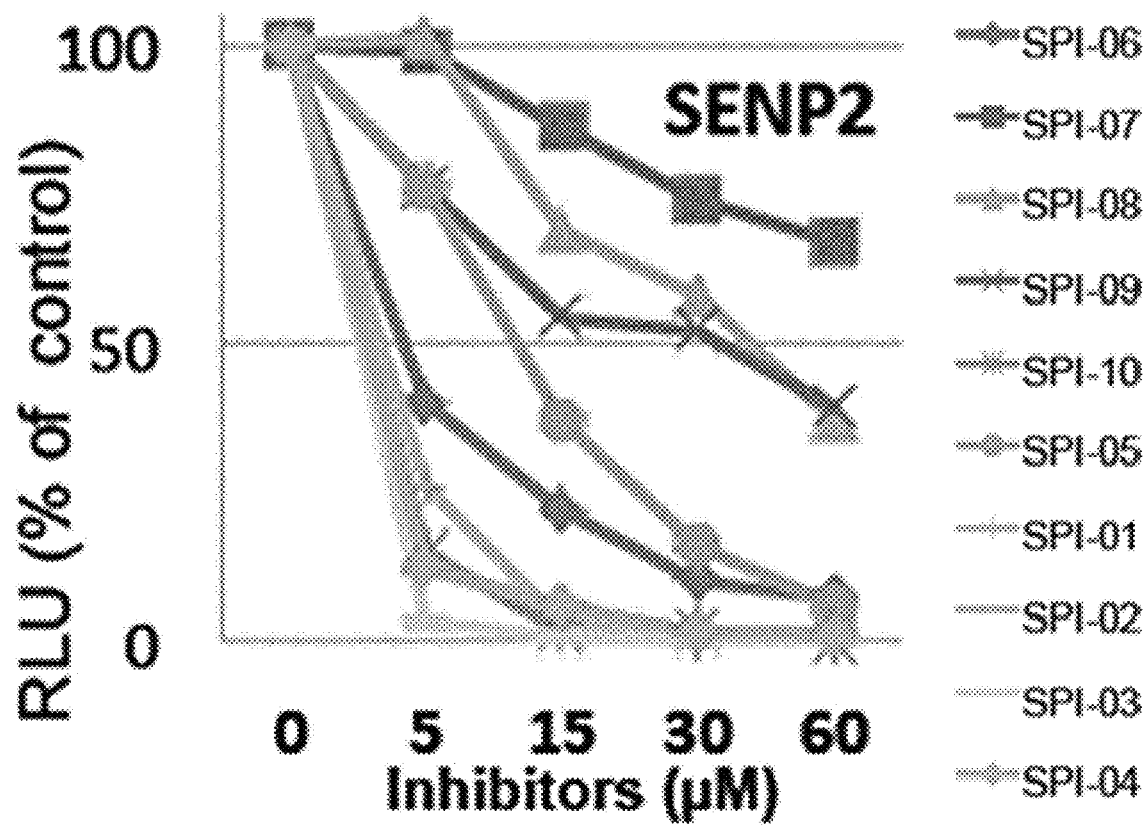
Figure 3C:
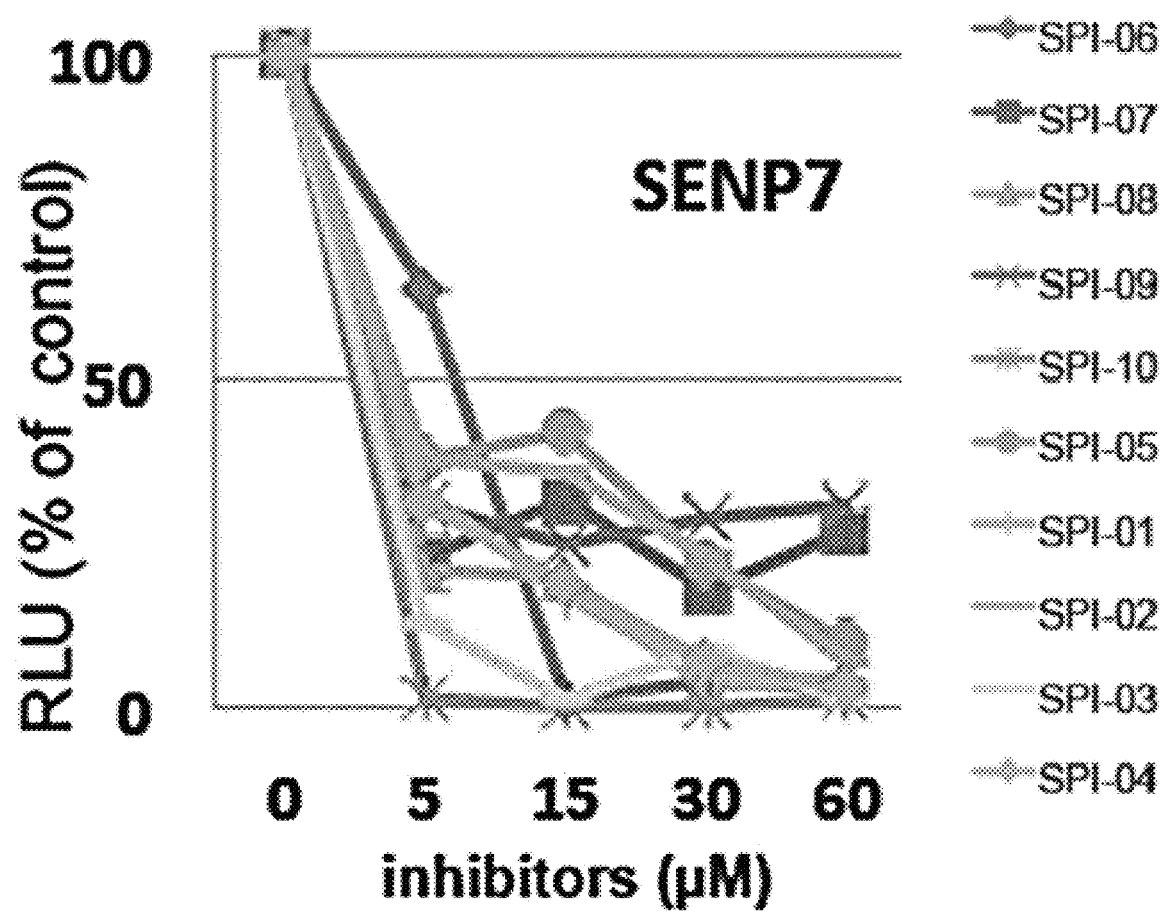

†Designation for our library of SUMO-protease inhibitors (SPI)
‡Designated by the National Cancer Institute To determine whether other SENPs can be inhibited by this family of inhibitors, a distant SENP member, SENP7, was tested in parallel with SENP1 and SENP2 using a pentapeptide substrate that contained the Gly-Gly motif and luciferin, known as DUB-Glo (Promega, Madison, Wis.). Cleavage of luciferin by a SENP can be detected by a coupled bioluminescent assay using luciferase. The bioluminescent reporter was chosen instead of a fluorescent reporter to avoid interference by the compounds during detection. In addition, because SENP7 has different physiological substrates than SENP1 and SENP2 (Kolli et al., *Biochemical Journal* 430:335-344 (2010); and Shen et al., *EMBO Rep.* 13(4):339-46 (2012)), an advantage of DUB-Glo is that it can act as a common substrate for all SENPs, which enabled us to rule out substrate-specific effects. The dose-dependent inhibition of each SENP by the inhibitors was determined (FIGS. 3A-3C), as was the IC$_{50}$ for inhibition of SENP1, 2 and 7 of all the compounds (Table 2). Most compounds had more similar inhibitory effects on SENP1 and SENP2 than on SENP7, consistent with their amino acid sequence similarities. In addition, the compounds were more potent for inhibiting SENP1 when DUB-Glo was used as a substrate than when SUMO-1 precursor was used (Tables 1 and 2). To rule out the possibility that these compounds used a promiscuous mechanism, the compounds were also tested in SUMOylation and ubiquitination reactions, which also depend on enzymes containing catalytic Cys residues. The compounds were noninhibitory in these assays. Furthermore, comparison of the DUB-Glo and the SUMO maturation assays revealed that the effect of SENP inhibitors could be highly substrate-specific.

TABLE 2

Inhibitory effect on SENP enzymatic activity using a bioluminescent peptide substrate

| Structure | Code† | NCI ID‡ | SENP1 IC$_{50}$ (μM) | SENP2 IC$_{50}$ (μM) | SENP7 IC$_{50}$ (μM) |
|---|---|---|---|---|---|
| 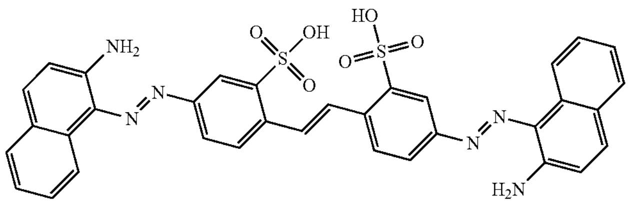 [SMILES: Nc1ccc2ccccc2c1/N=N/c1ccc(/C=C/c2ccc(/N=N/c3c(N)ccc4ccccc34)cc2S(=O)(=O)O)c(S(=O)(=O)O)c1] | SPI-01 | NSC5068 | 5.9 ± 1.4 | 2.9 ± 1.6 | 3.5 ± 1.5 |
| 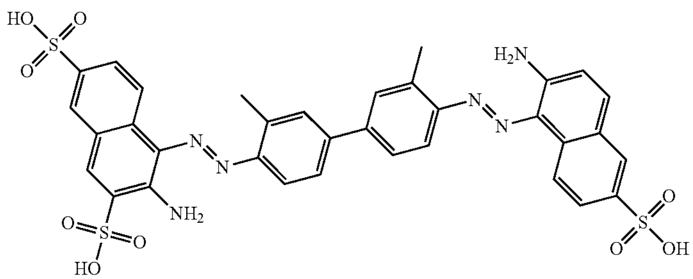 [SMILES: Cc1cc(-c2ccc(/N=N/c3c(N)c(S(=O)(=O)O)cc4cc(S(=O)(=O)O)ccc34)c(C)c2)ccc1/N=N/c1c(N)ccc2cc(S(=O)(=O)O)ccc12] | SPI-02 | NSC 16224 | 2.1 ± 1.9 | 2.0 ± 2.0 | 2.7 ± 1.8 |
| 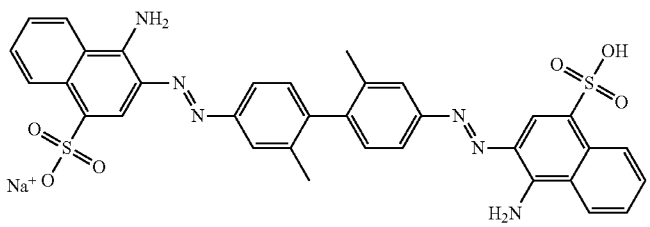 [SMILES: Cc1cc(/N=N/c2cc(S(=O)(=O)O)c3ccccc3c2N)ccc1-c1ccc(/N=N/c2cc(S(=O)(=O)O)c3ccccc3c2N)cc1C ; [Na+]] | SPI-03 | NSC 8676 | 3.8 ± 1.5 | 2.4 ± 1.8 | 4.8 ± 1.4 |
| 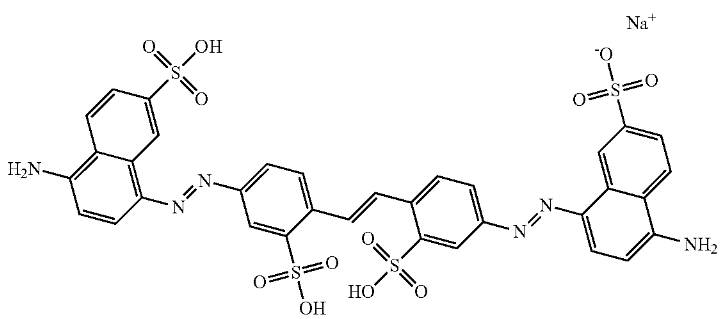 | SPI-04 | NSC 34933 | 2.4 ± 1.8 | 2.3 ± 1.8 | 3.4 ± 1.5 |
| 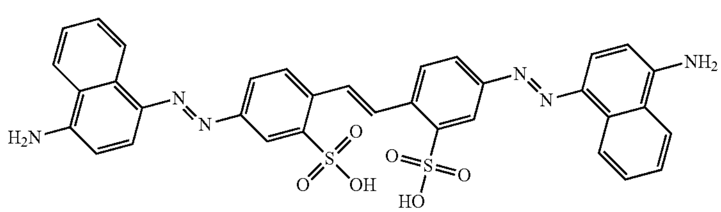 [SMILES: Nc1ccc(/N=N/c2ccc(/C=C/c3ccc(/N=N/c4ccc(N)c5ccccc45)cc3S(=O)(=O)O)c(S(=O)(=O)O)c2)c2ccccc12] | SPI-05 | NSC 5067 | 13.3 ± 1.3 | 8.5 ± 1.3 | 4.6 ± 1.5 |
| 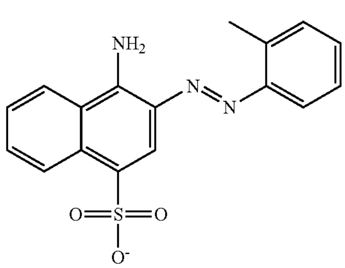 [SMILES: Cc1ccccc1/N=N/c1cc(S(=O)(=O)[O-])c2ccccc2c1N] | SPI-06 | NSC 70551 | 3.9 ± 1.4 | 3.7 ± 1.4 | 4.7 ± 1.7 |

TABLE 2-continued

Inhibitory effect on SENP enzymatic activity using a bioluminescent peptide substrate

| Structure | Code[†] | NCI ID[‡] | SENP1 IC$_{50}$ (μM) | SENP2 IC$_{50}$ (μM) | SENP7 IC$_{50}$ (μM) |
|---|---|---|---|---|---|
| *(structure)* | SPI-07 | NSC 58046 | >>60 | >>60 | 1.9 ± 2.2 |
| *(structure)* | SPI-08 | NSC 22940 | 22.2 ± 1.5 | 17.2 ± 1.5 | 2.8 ± 1.6 |
| *(structure)* | SPI-09 | NSC 42164 | >60 | 6.8 ± 1.3 | 1.9 ± 2.1 |
| *(structure)* | SPI-10 | NSC 45551 | 2.4 ± 1.8 | 2.5 ± 1.7 | 2.0 ± 2.0 |

Figure 4:
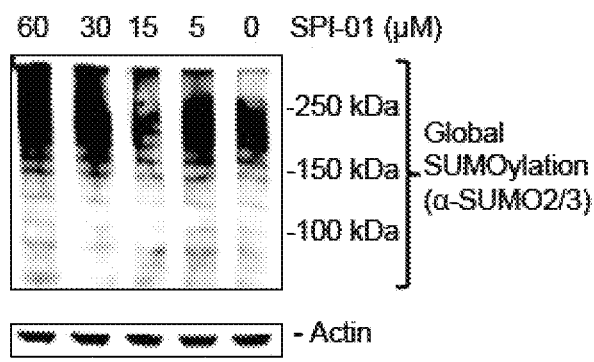
FIG. 4 is a picture of a gel showing accumulation of SUMO-2/3-modified proteins in HeLa cells upon treatment with increasing doses of SPI-01.
Figure 5:
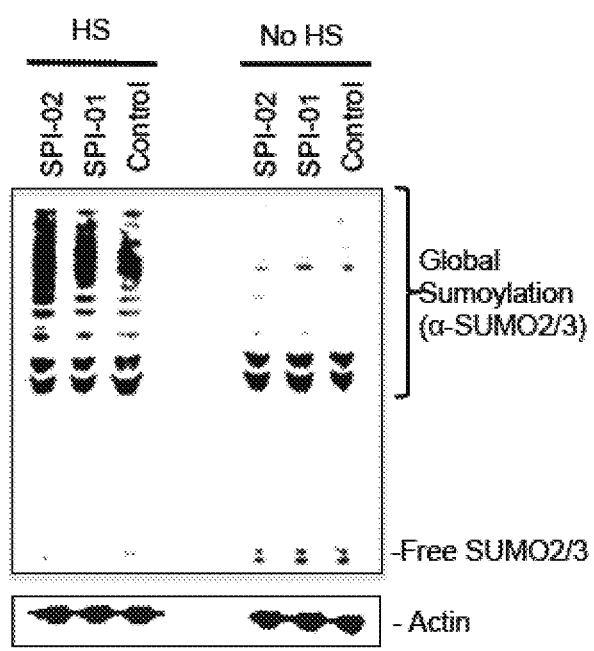
FIG. 5 is a picture of a gel showing retention of SUMOylated proteins during recovery of HeLa cells from heat shock in the presence of 60 µM SPI-01 and SPI-02.
Figure 6:
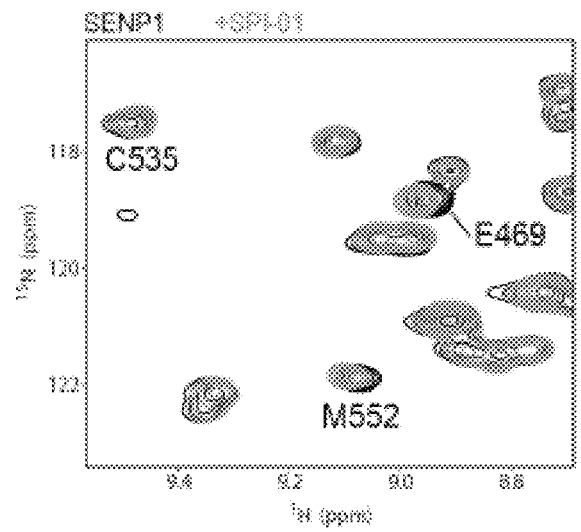
FIG. 6 is a graph showing superimposition of a section of the 2D $^1$H-$^{15}$N-heteronuclear single quantum coherence (HSQC) spectra of the catalytically inactive C603S mutant of human SENP1 in the absence (black cross-peaks) and presence of SPI-01 (grey cross-peaks) at 25° C. Perturbed representative cross-peaks at or near the catalytic site of SENP1 are labeled.

[†]Designation for our library of SUMO-protease inhibitors (SPI)
[‡]Designated by the National Cancer Institute The abilities of representative inhibitors were then tested to inhibit SENP in cells. HeLa cells were treated with increasing concentrations of SPI-01 for 48 hours, after which SUMOylated proteins were detected in the cells by Western blots. SUMO-2/3 conjugates accumulated in cells and this accumulation correlated with inhibitor concentration, particularly at high molecular weights (FIG. 4). This result suggests that SPI-01 inhibits the isopeptidase activities of SENPs, particularly SENP6 and SENP7, which are required for SUMO chain editing. It was observed that less significant effects on the accumulation of SUMO-1 conjugates, possibly because most SENPs cleave SUMO-2/3-conjugates. It is known that heat shock triggers a dramatic increase in global SUMO-2/3 conjugations and that during recovery, the SUMOylated proteins are removed, at least in part, due to the deSUMOylation activity of SENP1 (Nefkens et al., *J. Cell Sci.* 116:513-524 (2003)). To further confirm that the inhibitors inhibited deSUMOylase activities, HeLa cells were treated with SPI-01 and SPI-02 for 2 hours at 37° C. Then, SPI-treated or untreated control HeLa cells was transferred to 42° C. for 30 minutes, followed by recovery for 4 hours at 37° C. before processing for detection of global SUMO-2/3 levels. The inhibitor-treated cells had considerably higher levels of SUMOylated proteins than did the corresponding controls that did not receive heat shock or the mock-treated cells after the recovery period (FIG. 5). Thus, the results of the heat-shock experiments further confirmed that the SPI compounds had inhibitory effects on SENPs in cells.

Figure 2:
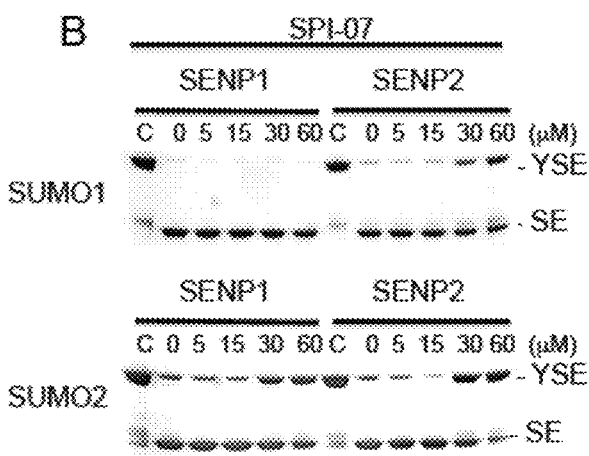
FIG. 2 is a picture of representative Coomassie-stained gel showing cleavage of SUMO-1 and SUMO-2 by SENP1 and SENP2 in the presence of increasing concentrations of SPI-07. YSE, fusion SUMO (S) precursors flanked by YFP (Y) and ECFP (E) at the N- and C-termini, respectively.

NMR chemical shift perturbation (CSP) analysis was used to investigate whether this family of inhibitors binds the enzyme or the enzyme-substrate complex. CSP experiments were conducted using a $^{15}$N-labeled C603 S mutant of the human SENP1 catalytic domain (SENP1-C603S, for which NMR chemical shift assignments have been obtained and deposited in the Biological Magnetic Resonance Bank (BMRB) with accession number 19083). Although the SENP1-C603S mutant is catalytically inactive (Xu et al., Biochem. J. 398:345-52 (2006)), it retains binding activity for the precursor or mature SUMO paralogs or SUMOylated substrates (Shen et al., Nat. Struct. Mol. Biol. 13:1069-1077 (2006)). It was observed that SPI-01 caused modest backbone amide CSP for a subset of SENP1-C603S residues. Of note, specific CSPs were observed at the canonical cysteine-protease catalytic triad residues (D550, H533, and C603), the proposed dynamic channel of conserved W465 and W534, and at several other residues located at or adjacent to the SENP catalytic center (W465, L466, G531, H533, W534, C535, M552, G554 and Q596) with only one residue located distal to this surface (E469) (FIG. 2). Interestingly, M552, G554, and Q596 are clustered at the SENP1 surface that contacts the C-terminal tail of SUMO-1. Supporting the importance of this surface in SENP catalytic activity, non-conservative point mutations of Q596 in SENP1 or the equivalent residue to SENP1 M552 in SENP2 (M497) perturb SUMO processing and deconjugation (Reverter and Lima, Nat. Struct. Mol. Biol. 13; 1060-8 (2006); and Shen et al., Biochem. J. 397:279-288 (2006)). Residue E469 is positioned toward the binding surface for the structured region of SUMO-1, and its CSP may be due to an alternative interaction with the compound or long-range effects. These results indicate that SPI-01 binds the surface adjacent to the catalytic center that contacts the C-terminal portion of the SUMO precursors. The residues that showed CSP are highly conserved between SENP1 and SENP2, suggesting that SPI-01 can interact with the equivalent surface on SENP2.

Figure 7:
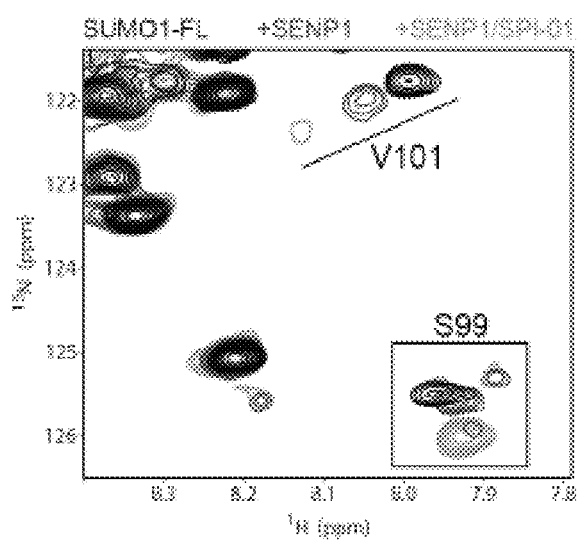
FIG. 7 is a graph showing the superimposition of a section of the 2D $^1$H-$^{15}$N-HSQC spectra of SUMO-1 precursor showing labeled peaks of the C-terminal residues when free (black) and bound to SENP1-C603S (dark grey) or both SENP1-C603S and SPI-01 (light grey) at 35° C.

The binding of SPI-01 to the enzyme-substrate complex was investigated. CSP analysis was carried out on the 40 kDa complex of $^{15}$N-labeled full length precursor SUMO-1-GGHSTV (SUMO-1-FL) with unlabeled SENP1-C603S. An equimolar amount of SPI-01 was added to the 1:1 enzyme-substrate complex. The only observed CSP on the $^{15}$N-labeled precursor SUMO-1-FL was on the C-terminal residues S99 and V101 (FIGS. 7 and 8) (Song et al., PNAS 101:14373-8 (2004)). This result indicates that SPI-01 binds the enzyme-substrate complex at the interface between SENP and the C-terminal tails of precursor SUMO-FL. X-ray crystal structures showed that the C-terminal tail of precursor SUMO sits in and projects out of the catalytic tunnel of SENPs (Shen et al., Nat. Struct. Mol. Biol. 13:1069-77 (2006)). In the case of SENP1, the region that interacts with the projected C-terminus is predominantly acidic and favors the C-terminus of SUMO-1, which is polar and positively charged, over that of SUMO-2, whose C-terminus is mainly hydrophobic (Shen et al., Nat. Struct. Mol. Biol. 13:1069-77 (2006); and Shen et al., The Biochemical Journal 397:279-88 (2006)). In addition, the more hydrophobic C-terminus of SUMO-2 may favor binding of aromatic inhibitors. These properties may account for the more potent inhibition of processing of the SUMO-2 precursor (Table 1).

To further investigate the inhibitory mechanism, enzyme kinetic experiments were conducted using the pentapeptide substrate DUB-Glo (FIG. 9). The data was fit to a mixed inhibition mechanism, as described by the kinetic equation:

$$v = \frac{V_{max}[S]}{\left(1 + \frac{[I]}{\alpha K_i}\right)\left[\frac{K_m\left(1 + \frac{[I]}{K_i}\right)}{1 + \frac{[I]}{\alpha K_i}} + [S]\right]}$$

in which the value of "α" indicates the mechanism of inhibition (Segel, Enzyme Kinetics John Wiley & Sons (1993)). For both SENP1 and SENP2, the "α" values indicated that the inhibitory mechanism is mainly noncompetitive and suggests that the inhibitor binds to the enzyme and the enzyme-substrate complex to inhibit chemical conversion. This finding is consistent with the NMR binding analysis indicating that the inhibitor binds both the enzyme and the enzyme-substrate complex as discussed above.

In conclusion, this study has identified SENP inhibitors that do not covalently modify the catalytic Cys residue. This study has also provided the first mechanistic insights into how a small molecule inhibitor of SENPs that does not covalently modify the catalytic Cys can inhibit the enzymes. The substrate-assisted inhibitor binding indicates the need for caution in designing high throughput screening assays that use fluorogenic or chemiluminescent artificial substrates, as the results could be significantly different from using the physiological substrates. The substrate-dependent inhibitory effect suggests the possibility of designing SENP inhibitors that are tuned for substrate-specificity.

Materials and Methods

Protein Purification. The catalytic domains of SENP1, 2, and 7 were expressed as His-tagged protein in E. coli (DE3) and purified using nickel affinity chromatography (Namanja et al., The Journal of Biological Chemistry 287:3231-3240 (2012)). The pET11 expression plasmids for SENP1 and 2 contained a cDNA insert coding for the catalytic domain of human SENP1-WT (419-644) and SENP2-WT (364-589). The expression plasmid for the SENP1 active site point mutant C603 S was generated using the QuikChange mutagenesis kit (Agilent Technologies, San Diego, Calif.). The expression plasmid for the catalytic domain of SENP7 has been described (Mikolajczyk et al., Journal of Biological Chemistry 282:26217-26224 (2007)).

SUMO Cleavage Assays. SUMO cleavage assays were performed by incubating SENPs with various concentrations of the inhibitor (0-60 μM) at room temperature for 10 min in assay buffer (50 mM Tris, pH 7.4, 100 mM NaCl, 10 mM DTT). SENP concentrations were 32-50 nM when 50 μg/ml of the final substrate YFP-SUMO-ECFP (YSE) fusion protein was added. The mixture was incubated (37° C., 15 min), followed by SDS-PAGE and Coomassie staining for visualization. For cellular SENP inhibition experiments, HeLa cells cultured in DMEM plus 10% FBS, 100 units/ml penicillin, 100 mg/ml streptomycin, and 0.2 M glutamine were treated for 48 hours with SPI compounds. For heat shock experiment, HeLa cells were treated with SPI compounds or mock treated (2 h, 37° C.), after which cells were transferred to 42° C. for 30 min. After heat shock, the cells were allowed to recover (4-5 hours) before being harvested and lysed. Proteins were separated by SDS-PAGE and immunoblotted to determine global SUMO-2/3 levels.

DUB-Glo Assay. The luciferase substrate assay (DUB-Glo, Promega, Madison, Wis.) was performed according to the manufacturer's instructions. Briefly, SENPs (final concentration 50-100 nM) in Tris buffer (50 mM Tris, pH 8.0, 100 mM NaCl, 10 mM DTT) were pre-incubated (10 min, room temperature) with increasing concentrations of inhibitor (0-60 μM final concentration) followed by addition of the luciferase substrate. Luciferase output was recorded 30 min after addition of the luciferase substrate. Values are the averages of experiments performed in triplicate.

NMR Experiments. Samples used for NMR titration or chemical shift perturbation analyses were $^{15}$N or $^{15}$N/$^{13}$C-labeled; the titrant protein or SPI-01 was not labeled. The $^{15}$N/$^{13}$C SUMO-1-FL sample was used to extend the backbone assignments of mature SUMO-1 to the HSTV tail by using 2D-$^{15}$N-$^1$H-HSQC, 3D-HNCA, 3D-HNCOCA, and 3D-HNCACB. Additionally, comparison of $^{15}$N-$^1$H-HSQC between precursor and mature SUMO quickly identified the resonances of the HSTV tail. For SENP1 assignments, a full suite of triple-resonance NMR experiments were acquired on $^{15}$N/$^{13}$C/$^2$H or $^{15}$N/13C samples: HNCA, HNCOCA, HNCACB, HNCOCACB, HNCO, HNCACO, and NOESY-HSQC. All samples were dissolved in the NMR buffer: 20 mM sodium phosphate (pH 6.8), 10% D2O, 0.03% sodium azide and 10 mM d10-dithiothreitol. Purified perdeuterated SENP1 samples were unfolded and refolded into NMR buffer.

For titration of SENP1-C603S with SPI-01, 270 μM $^{15}$N-labeled sample was titrated with the inhibitor that was prepared by diluting a 10 mM stock in 100% DMSO-d$_6$ to a concentration of 1.7 mM in the NMR buffer. The 2D $^1$H-$^{15}$N-HSQC spectra of SENP1 were recorded at each incremental addition of 5 μl of SPI-01 into 250 μl of SENP1. The chemical shift perturbation (CSP) analysis compared the spectra of SENP1 in the absence or the presence of equimolar SPI-01. A separate DMSO control titration was performed to account for DMSO-induced CSP. NMR resonance assignments for SUMO samples at 35° C. were transferred from those obtained at 25° C. by spectral acquisition at 2.5° C. incremental increases. All data were acquired on a 600 MHz Bruker Avance NMR spectrometer equipped with a TXI Cryoprobe.

TABLE 3

Free SENP1 NMR Chemical Shifts Values.
Chemical Shift Ambiguity Index Value Definitions
The values other than 1 are used for those atoms with different chemical shifts that cannot be assigned to stereospecific atoms or to specific residues or chains.

| Index Value | Definition |
|---|---|
| 1 | Unique (including isolated methyl protons germinal atoms, and geminal methyl groups with identical chemical shifts (e.g. ILE HD11, HD12, HD13 protons) |
| 2 | Ambiguity of geminal atoms or geminal methyl proton groups (e.g. ASP HB2 and HB3 protons, LEU CD1 and CD2 carbons, or LEU HD11, HD12, HD13 and HD21, HD22, HD23 methyl protons) |
| 3 | Aromatic atoms on opposite sides of symmetrical rings (e.g. TYR HE1 and HE2 protons) |
| 4 | Intraresidue ambiguities (e.g. LYS HG and HD protons or TRP HZ2 and HZ3 protons) |
| 5 | Interresidue ambiguities (LYS 12 vs. LYS 27) |
| 6 | Intermolecular ambiguities (e.g. ASP 31 CA in monomer 1 and ASP 31 CA in monomer 2 of an asymmetrical homodimer, duplex DNA assignments, or other assignments that may apply to atoms in one or more molecule in the molecular assembly) |
| 9 | Ambiguous, specific ambiguity not defined |

| Atom number | Residue number | Amino acid | Atom context | Atom type | Iso-type | Chemical shift (ppm)* | Unique-ness |
|---|---|---|---|---|---|---|---|
| 1 | 419 | E | CA | C | 13 | 56.635 | 1 |
| 2 | 419 | E | CB | C | 13 | 29.326 | 1 |
| 3 | 419 | E | CO | C | 13 | 175.803 | 1 |
| 4 | 419 | E | H | H | 1 | 8.056 | 1 |
| 5 | 419 | E | N | N | 15 | 120.257 | 1 |
| 6 | 420 | F | CA | C | 13 | 54.951 | 1 |
| 7 | 420 | F | CB | C | 13 | 37.882 | 1 |
| 8 | 420 | F | CO | C | 13 | 173.207 | 1 |
| 9 | 420 | F | H | H | 1 | 8.035 | 1 |
| 10 | 420 | F | N | N | 15 | 118.648 | 1 |
| 11 | 422 | E | CA | C | 13 | 56.498 | 1 |
| 12 | 422 | E | CB | C | 13 | 29.476 | 1 |
| 13 | 422 | E | CO | C | 13 | 176.111 | 1 |
| 14 | 422 | E | H | H | 1 | 8.637 | 1 |
| 15 | 422 | E | N | N | 15 | 124.065 | 1 |
| 16 | 423 | I | CA | C | 13 | 60.725 | 1 |
| 17 | 423 | I | CB | C | 13 | 35.427 | 1 |
| 18 | 423 | I | CO | C | 13 | 176.659 | 1 |
| 19 | 423 | I | H | H | 1 | 8.522 | 1 |
| 20 | 423 | I | N | N | 15 | 122.041 | 1 |
| 21 | 424 | T | CB | C | 13 | 70.292 | 1 |
| 22 | 424 | T | CO | C | 13 | 174.725 | 1 |
| 23 | 424 | T | H | H | 1 | 7.633 | 1 |
| 24 | 424 | T | N | N | 15 | 121.188 | 1 |
| 25 | 425 | E | CA | C | 13 | 59.696 | 1 |
| 26 | 425 | E | CB | C | 13 | 28.462 | 1 |
| 27 | 425 | E | H | H | 1 | 8.913 | 1 |
| 28 | 425 | E | N | N | 15 | 120.9 | 1 |
| 29 | 426 | E | CA | C | 13 | 59.444 | 1 |
| 30 | 426 | E | CO | C | 13 | 179.787 | 1 |
| 31 | 426 | E | H | H | 1 | 8.419 | 1 |
| 32 | 426 | E | N | N | 15 | 118.024 | 1 |
| 33 | 427 | M | CB | C | 13 | 33.371 | 1 |
| 34 | 427 | M | CO | C | 13 | 177.912 | 1 |
| 35 | 427 | M | H | H | 1 | 7.366 | 1 |
| 36 | 427 | M | N | N | 15 | 119.301 | 1 |
| 37 | 428 | E | CB | C | 13 | 28.41 | 1 |
| 38 | 428 | E | CO | C | 13 | 178.828 | 1 |
| 39 | 428 | E | H | H | 1 | 8.605 | 1 |
| 40 | 428 | E | N | N | 15 | 118.58 | 1 |
| 41 | 429 | K | CA | C | 13 | 59.488 | 1 |
| 42 | 429 | K | CB | C | 13 | 31.407 | 1 |
| 43 | 429 | K | CO | C | 13 | 178.978 | 1 |
| 44 | 429 | K | H | H | 1 | 7.858 | 1 |
| 45 | 429 | K | N | N | 15 | 118.101 | 1 |
| 46 | 430 | E | CB | C | 13 | 29.584 | 1 |
| 47 | 430 | E | CO | C | 13 | 179.111 | 1 |
| 48 | 430 | E | H | H | 1 | 7.356 | 1 |
| 49 | 430 | E | N | N | 15 | 119.087 | 1 |
| 50 | 431 | I | CA | C | 13 | 64.567 | 1 |
| 51 | 431 | I | CB | C | 13 | 38.123 | 1 |
| 52 | 431 | I | CO | C | 13 | 176.796 | 1 |
| 53 | 431 | I | H | H | 1 | 8.075 | 1 |
| 54 | 431 | I | N | N | 15 | 119.774 | 1 |
| 55 | 432 | K | CA | C | 13 | 59.195 | 1 |
| 56 | 432 | K | CB | C | 13 | 31.197 | 1 |
| 57 | 432 | K | CO | C | 13 | 180.185 | 1 |
| 58 | 432 | K | H | H | 1 | 8.32 | 1 |
| 59 | 432 | K | N | N | 15 | 116.686 | 1 |
| 60 | 433 | N | CA | C | 13 | 55.822 | 1 |
| 61 | 433 | N | CB | C | 13 | 37.95 | 1 |
| 62 | 433 | N | CO | C | 13 | 178.466 | 1 |
| 63 | 433 | N | H | H | 1 | 7.635 | 1 |
| 64 | 433 | N | N | N | 15 | 114.913 | 1 |
| 65 | 434 | V | CA | C | 13 | 64.189 | 1 |
| 66 | 434 | V | CB | C | 13 | 30.396 | 1 |
| 67 | 434 | V | CG1 | C | 13 | 22.475 | 1 |
| 68 | 434 | V | CG2 | C | 13 | 21.674 | 1 |
| 69 | 434 | V | CO | C | 13 | 176.412 | 1 |
| 70 | 434 | V | H | H | 1 | 7.548 | 1 |
| 71 | 434 | V | HG1 | H | 1 | 0.724 | 1 |
| 72 | 434 | V | HG2 | H | 1 | 0.725 | 1 |
| 73 | 434 | V | N | N | 15 | 114.74 | 1 |
| 74 | 435 | F | CA | C | 13 | 55.321 | 1 |
| 75 | 435 | F | CB | C | 13 | 37.701 | 1 |
| 76 | 435 | F | CO | C | 13 | 177.18 | 1 |
| 77 | 435 | F | H | H | 1 | 7.344 | 1 |
| 78 | 435 | F | N | N | 15 | 117.562 | 1 |
| 79 | 436 | R | CA | C | 13 | 56.384 | 1 |
| 80 | 436 | R | CB | C | 13 | 30.009 | 1 |
| 81 | 436 | R | CO | C | 13 | 176.099 | 1 |
| 82 | 436 | R | H | H | 1 | 7.225 | 1 |
| 83 | 436 | R | N | N | 15 | 118.73 | 1 |
| 84 | 437 | N | CA | C | 13 | 53.605 | 1 |
| 85 | 437 | N | CB | C | 13 | 38.193 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 86 | 437 | N | H | H | 1 | 8.252 | 1 |
| 87 | 437 | N | N | N | 15 | 119.685 | 1 |
| 88 | 438 | G | CA | C | 13 | 44.807 | 1 |
| 89 | 438 | G | CO | C | 13 | 172.725 | 1 |
| 90 | 438 | G | H | H | 1 | 8.08 | 1 |
| 91 | 438 | G | N | N | 15 | 109.481 | 1 |
| 92 | 439 | N | CA | C | 13 | 52.847 | 1 |
| 93 | 439 | N | CB | C | 13 | 37.175 | 1 |
| 94 | 439 | N | H | H | 1 | 8.737 | 1 |
| 95 | 439 | N | N | N | 15 | 120.443 | 1 |
| 96 | 440 | Q | CA | C | 13 | 58.04 | 1 |
| 97 | 440 | Q | CB | C | 13 | 28.495 | 1 |
| 98 | 440 | Q | CO | C | 13 | 175.605 | 1 |
| 99 | 440 | Q | H | H | 1 | 9.022 | 1 |
| 100 | 440 | Q | N | N | 15 | 125.59 | 1 |
| 101 | 441 | D | CA | C | 13 | 53.428 | 1 |
| 102 | 441 | D | CB | C | 13 | 40.409 | 1 |
| 103 | 441 | D | CO | C | 13 | 175.45 | 1 |
| 104 | 441 | D | H | H | 1 | 7.969 | 1 |
| 105 | 441 | D | N | N | 15 | 114.845 | 1 |
| 106 | 442 | E | CA | C | 13 | 56.501 | 1 |
| 107 | 442 | E | CB | C | 13 | 30.044 | 1 |
| 108 | 442 | E | CO | C | 13 | 175.905 | 1 |
| 109 | 442 | E | H | H | 1 | 7.143 | 1 |
| 110 | 442 | E | N | N | 15 | 121.501 | 1 |
| 111 | 443 | V | CA | C | 13 | 64.02 | 1 |
| 112 | 443 | V | CB | C | 13 | 31.155 | 1 |
| 113 | 443 | V | CG1 | C | 13 | 21.487 | 1 |
| 114 | 443 | V | CG2 | C | 13 | 21.844 | 1 |
| 115 | 443 | V | H | H | 1 | 8.65 | 1 |
| 116 | 443 | V | HG1 | H | 1 | 0.721 | 1 |
| 117 | 443 | V | HG2 | H | 1 | 0.882 | 1 |
| 118 | 443 | V | N | N | 15 | 127.026 | 1 |
| 119 | 444 | L | CA | C | 13 | 54.051 | 1 |
| 120 | 444 | L | CB | C | 13 | 43.293 | 1 |
| 121 | 444 | L | CD1 | C | 13 | 27.029 | 1 |
| 122 | 444 | L | CD2 | C | 13 | 21.807 | 1 |
| 123 | 444 | L | CO | C | 13 | 176.79 | 1 |
| 124 | 444 | L | H | H | 1 | 9.012 | 1 |
| 125 | 444 | L | HD1 | H | 1 | 0.59 | 1 |
| 126 | 444 | L | HD2 | H | 1 | 0.597 | 1 |
| 127 | 444 | L | N | N | 15 | 127.296 | 1 |
| 128 | 445 | S | CA | C | 13 | 57.432 | 1 |
| 129 | 445 | S | CB | C | 13 | 64.093 | 1 |
| 130 | 445 | S | CO | C | 13 | 172 | 1 |
| 131 | 445 | S | H | H | 1 | 7.412 | 1 |
| 132 | 445 | S | N | N | 15 | 111.726 | 1 |
| 133 | 446 | E | CA | C | 13 | 55.317 | 1 |
| 134 | 446 | E | CB | C | 13 | 31.965 | 1 |
| 135 | 446 | E | CO | C | 13 | 174.257 | 1 |
| 136 | 446 | E | H | H | 1 | 7.933 | 1 |
| 137 | 446 | E | N | N | 15 | 125.063 | 1 |
| 138 | 447 | A | CA | C | 13 | 51.875 | 1 |
| 139 | 447 | A | CB | C | 13 | 18.979 | 1 |
| 140 | 447 | A | CO | C | 13 | 176.087 | 1 |
| 141 | 447 | A | H | H | 1 | 8.286 | 1 |
| 142 | 447 | A | N | N | 15 | 124.213 | 1 |
| 143 | 448 | F | CA | C | 13 | 56.316 | 1 |
| 144 | 448 | F | CB | C | 13 | 36.029 | 1 |
| 145 | 448 | F | CO | C | 13 | 175.788 | 1 |
| 146 | 448 | F | H | H | 1 | 8.61 | 1 |
| 147 | 448 | F | N | N | 15 | 115.367 | 1 |
| 148 | 449 | R | CA | C | 13 | 57.675 | 1 |
| 149 | 449 | R | CB | C | 13 | 26.229 | 1 |
| 150 | 449 | R | CO | C | 13 | 175.491 | 1 |
| 151 | 449 | R | H | H | 1 | 8.484 | 1 |
| 152 | 449 | R | N | N | 15 | 110.844 | 1 |
| 153 | 450 | L | CA | C | 13 | 53.763 | 1 |
| 154 | 450 | L | CB | C | 13 | 44.035 | 1 |
| 155 | 450 | L | CD1 | C | 13 | 25.813 | 1 |
| 156 | 450 | L | CD2 | C | 13 | 22.437 | 1 |
| 157 | 450 | L | CO | C | 13 | 176.645 | 1 |
| 158 | 450 | L | H | H | 1 | 8.389 | 1 |
| 159 | 450 | L | HD1 | H | 1 | 0.89 | 1 |
| 160 | 450 | L | HD2 | H | 1 | 0.948 | 1 |
| 161 | 450 | L | N | N | 15 | 121.623 | 1 |
| 162 | 451 | T | CA | C | 13 | 60.834 | 1 |
| 163 | 451 | T | CB | C | 13 | 71.178 | 1 |
| 164 | 451 | T | CO | C | 13 | 173.407 | 1 |
| 165 | 451 | T | H | H | 1 | 8.315 | 1 |
| 166 | 451 | T | N | N | 15 | 113.296 | 1 |
| 167 | 452 | I | CA | C | 13 | 56.522 | 1 |
| 168 | 452 | I | CB | C | 13 | 36.082 | 1 |
| 169 | 452 | I | CO | C | 13 | 176.082 | 1 |
| 170 | 452 | I | H | H | 1 | 8.521 | 1 |
| 171 | 452 | I | N | N | 15 | 124.173 | 1 |
| 172 | 453 | T | CA | C | 13 | 59.709 | 1 |
| 173 | 453 | T | CB | C | 13 | 72.939 | 1 |
| 174 | 453 | T | H | H | 1 | 9.811 | 1 |
| 175 | 453 | T | N | N | 15 | 119.807 | 1 |
| 176 | 454 | R | CA | C | 13 | 60.137 | 1 |
| 177 | 454 | R | CB | C | 13 | 28.989 | 1 |
| 178 | 454 | R | CO | C | 13 | 177.392 | 1 |
| 179 | 454 | R | H | H | 1 | 8.211 | 1 |
| 180 | 454 | R | N | N | 15 | 122.061 | 1 |
| 181 | 455 | K | CA | C | 13 | 59.289 | 1 |
| 182 | 455 | K | CB | C | 13 | 31.114 | 1 |
| 183 | 455 | K | CO | C | 13 | 178.628 | 1 |
| 184 | 455 | K | H | H | 1 | 8.504 | 1 |
| 185 | 455 | K | N | N | 15 | 119.122 | 1 |
| 186 | 456 | D | CA | C | 13 | 57.369 | 1 |
| 187 | 456 | D | CB | C | 13 | 40.809 | 1 |
| 188 | 456 | D | H | H | 1 | 7.271 | 1 |
| 189 | 456 | D | N | N | 15 | 117.779 | 1 |
| 190 | 457 | I | CA | C | 13 | 62.392 | 1 |
| 191 | 457 | I | CB | C | 13 | 37.06 | 1 |
| 192 | 457 | I | H | H | 1 | 8.159 | 1 |
| 193 | 457 | I | N | N | 15 | 121.588 | 1 |
| 194 | 458 | Q | CA | C | 13 | 57.804 | 1 |
| 195 | 458 | Q | CB | C | 13 | 26.567 | 1 |
| 196 | 458 | Q | CO | C | 13 | 178.732 | 1 |
| 197 | 458 | Q | H | H | 1 | 7.923 | 1 |
| 198 | 458 | Q | N | N | 15 | 117.897 | 1 |
| 199 | 459 | T | CA | C | 13 | 65.051 | 1 |
| 200 | 459 | T | CB | C | 13 | 67.395 | 1 |
| 201 | 459 | T | H | H | 1 | 7.897 | 1 |
| 202 | 459 | T | N | N | 15 | 113.263 | 1 |
| 203 | 460 | L | CA | C | 13 | 54.923 | 1 |
| 204 | 460 | L | CB | C | 13 | 41.723 | 1 |
| 205 | 460 | L | CD1 | C | 13 | 25.968 | 1 |
| 206 | 460 | L | CD2 | C | 13 | 25.889 | 1 |
| 207 | 460 | L | CO | C | 13 | 179.644 | 1 |
| 208 | 460 | L | H | H | 1 | 7.253 | 1 |
| 209 | 460 | L | HD1 | H | 1 | 0.82 | 1 |
| 210 | 460 | L | HD2 | H | 1 | 0.925 | 1 |
| 211 | 460 | L | N | N | 15 | 115.083 | 1 |
| 212 | 461 | N | CA | C | 13 | 51.888 | 1 |
| 213 | 461 | N | CB | C | 13 | 37.194 | 1 |
| 214 | 461 | N | H | H | 1 | 7.421 | 1 |
| 215 | 461 | N | N | N | 15 | 119.845 | 1 |
| 216 | 462 | H | CA | C | 13 | 57.014 | 1 |
| 217 | 462 | H | CB | C | 13 | 28.992 | 1 |
| 218 | 462 | H | H | H | 1 | 7.773 | 1 |
| 219 | 462 | H | N | N | 15 | 119.821 | 1 |
| 220 | 465 | W | CA | C | 13 | 56.901 | 1 |
| 221 | 465 | W | CB | C | 13 | 27.801 | 1 |
| 222 | 465 | W | H | H | 1 | 8.319 | 1 |
| 223 | 465 | W | HE1 | H | 1 | 10.206 | 1 |
| 224 | 465 | W | N | N | 15 | 120.321 | 1 |
| 225 | 465 | W | NE1 | N | 15 | 130.435 | 1 |
| 226 | 466 | L | CA | C | 13 | 57.74 | 1 |
| 227 | 466 | L | CB | C | 13 | 41.916 | 1 |
| 228 | 466 | L | CD1 | C | 13 | 25.446 | 1 |
| 229 | 466 | L | CD2 | C | 13 | 23.298 | 1 |
| 230 | 466 | L | H | H | 1 | 7.644 | 1 |
| 231 | 466 | L | HD1 | H | 1 | 0.634 | 1 |
| 232 | 466 | L | HD2 | H | 1 | 0.563 | 1 |
| 233 | 466 | L | N | N | 15 | 125.508 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 234 | 467 | N | CA | C | 13 | 50.295 | 1 |
| 235 | 467 | N | CB | C | 13 | 39.556 | 1 |
| 236 | 467 | N | CO | C | 13 | 174.619 | 1 |
| 237 | 467 | N | H | H | 1 | 7.164 | 1 |
| 238 | 467 | N | N | N | 15 | 116.901 | 1 |
| 239 | 468 | D | CA | C | 13 | 57.481 | 1 |
| 240 | 468 | D | CB | C | 13 | 40.531 | 1 |
| 241 | 468 | D | H | H | 1 | 8.246 | 1 |
| 242 | 468 | D | N | N | 15 | 115.434 | 1 |
| 243 | 469 | E | CA | C | 13 | 60.578 | 1 |
| 244 | 469 | E | CB | C | 13 | 27.414 | 1 |
| 245 | 469 | E | CO | C | 13 | 179.948 | 1 |
| 246 | 469 | E | H | H | 1 | 8.991 | 1 |
| 247 | 469 | E | N | N | 15 | 119.089 | 1 |
| 248 | 470 | I | CA | C | 13 | 61.231 | 1 |
| 249 | 470 | I | CB | C | 13 | 34.744 | 1 |
| 250 | 470 | I | CO | C | 13 | 177.04 | 1 |
| 251 | 470 | I | H | H | 1 | 7.753 | 1 |
| 252 | 470 | I | N | N | 15 | 117.845 | 1 |
| 253 | 471 | I | CA | C | 13 | 64.903 | 1 |
| 254 | 471 | I | H | H | 1 | 6.974 | 1 |
| 255 | 471 | I | N | N | 15 | 117.941 | 1 |
| 256 | 472 | N | CA | C | 13 | 56.07 | 1 |
| 257 | 472 | N | CB | C | 13 | 37.624 | 1 |
| 258 | 472 | N | CO | C | 13 | 178.288 | 1 |
| 259 | 472 | N | H | H | 1 | 9.03 | 1 |
| 260 | 472 | N | N | N | 15 | 115.254 | 1 |
| 261 | 473 | F | CA | C | 13 | 62.584 | 1 |
| 262 | 473 | F | CB | C | 13 | 39.667 | 1 |
| 263 | 473 | F | CO | C | 13 | 177.436 | 1 |
| 264 | 473 | F | H | H | 1 | 8.304 | 1 |
| 265 | 473 | F | N | N | 15 | 123.63 | 1 |
| 266 | 474 | Y | CA | C | 13 | 62.784 | 1 |
| 267 | 474 | Y | CB | C | 13 | 38.335 | 1 |
| 268 | 474 | Y | CO | C | 13 | 178.151 | 1 |
| 269 | 474 | Y | H | H | 1 | 8.774 | 1 |
| 270 | 474 | Y | N | N | 15 | 120.467 | 1 |
| 271 | 475 | M | CA | C | 13 | 57.325 | 1 |
| 272 | 475 | M | CB | C | 13 | 31.041 | 1 |
| 273 | 475 | M | CO | C | 13 | 179.367 | 1 |
| 274 | 475 | M | H | H | 1 | 8.709 | 1 |
| 275 | 475 | M | N | N | 15 | 115.346 | 1 |
| 276 | 476 | N | CA | C | 13 | 56.292 | 1 |
| 277 | 476 | N | CB | C | 13 | 37.912 | 1 |
| 278 | 476 | N | CO | C | 13 | 177.604 | 1 |
| 279 | 476 | N | H | H | 1 | 7.371 | 1 |
| 280 | 476 | N | N | N | 15 | 117.074 | 1 |
| 281 | 477 | M | CA | C | 13 | 59.952 | 1 |
| 282 | 477 | M | CB | C | 13 | 31.504 | 1 |
| 283 | 477 | M | CO | C | 13 | 179.545 | 1 |
| 284 | 477 | M | H | H | 1 | 7.664 | 1 |
| 285 | 477 | M | N | N | 15 | 121.465 | 1 |
| 286 | 478 | L | CA | C | 13 | 57.471 | 1 |
| 287 | 478 | L | CB | C | 13 | 39.79 | 1 |
| 288 | 478 | L | CD1 | C | 13 | 27.34 | 1 |
| 289 | 478 | L | CD2 | C | 13 | 22.112 | 1 |
| 290 | 478 | L | CO | C | 13 | 180.857 | 1 |
| 291 | 478 | L | H | H | 1 | 7.767 | 1 |
| 292 | 478 | L | HD1 | H | 1 | 0.658 | 1 |
| 293 | 478 | L | HD2 | H | 1 | 0.411 | 1 |
| 294 | 478 | L | N | N | 15 | 119.925 | 1 |
| 295 | 479 | M | CA | C | 13 | 59.413 | 1 |
| 296 | 479 | M | CB | C | 13 | 32.433 | 1 |
| 297 | 479 | M | CO | C | 13 | 179.134 | 1 |
| 298 | 479 | M | H | H | 1 | 7.603 | 1 |
| 299 | 479 | M | N | N | 15 | 118.957 | 1 |
| 300 | 480 | E | CA | C | 13 | 59.225 | 1 |
| 301 | 480 | E | CB | C | 13 | 28.37 | 1 |
| 302 | 480 | E | H | H | 1 | 8.059 | 1 |
| 303 | 480 | E | N | N | 15 | 122.932 | 1 |
| 304 | 481 | R | CA | C | 13 | 58.251 | 1 |
| 305 | 481 | R | CB | C | 13 | 28.749 | 1 |
| 306 | 481 | R | CO | C | 13 | 176.421 | 1 |
| 307 | 481 | R | H | H | 1 | 7.917 | 1 |
| 308 | 481 | R | N | N | 15 | 120.662 | 1 |
| 309 | 482 | S | CA | C | 13 | 60.255 | 1 |
| 310 | 482 | S | CB | C | 13 | 63.102 | 1 |
| 311 | 482 | S | CO | C | 13 | 172.394 | 1 |
| 312 | 482 | S | H | H | 1 | 7.201 | 1 |
| 313 | 482 | S | N | N | 15 | 113.273 | 1 |
| 314 | 483 | K | CA | C | 13 | 56.793 | 1 |
| 315 | 483 | K | CB | C | 13 | 31.687 | 1 |
| 316 | 483 | K | CO | C | 13 | 178.176 | 1 |
| 317 | 483 | K | H | H | 1 | 6.968 | 1 |
| 318 | 483 | K | N | N | 15 | 118.755 | 1 |
| 319 | 484 | E | CB | C | 13 | 29.049 | 1 |
| 320 | 484 | E | CO | C | 13 | 176.653 | 1 |
| 321 | 484 | E | H | H | 1 | 8.114 | 1 |
| 322 | 484 | E | N | N | 15 | 121.011 | 1 |
| 323 | 485 | K | CA | C | 13 | 57.55 | 1 |
| 324 | 485 | K | CB | C | 13 | 31.154 | 1 |
| 325 | 485 | K | CO | C | 13 | 177.924 | 1 |
| 326 | 485 | K | H | H | 1 | 8.263 | 1 |
| 327 | 485 | K | N | N | 15 | 121.725 | 1 |
| 328 | 486 | G | CA | C | 13 | 44.731 | 1 |
| 329 | 486 | G | CO | C | 13 | 173.993 | 1 |
| 330 | 486 | G | H | H | 1 | 8.738 | 1 |
| 331 | 486 | G | N | N | 15 | 111.446 | 1 |
| 332 | 487 | L | CA | C | 13 | 52.224 | 1 |
| 333 | 487 | L | CB | C | 13 | 40.075 | 1 |
| 334 | 487 | L | CD1 | C | 13 | 25.797 | 1 |
| 335 | 487 | L | CD2 | C | 13 | 23.228 | 1 |
| 336 | 487 | L | CO | C | 13 | 174.966 | 1 |
| 337 | 487 | L | H | H | 1 | 7.357 | 1 |
| 338 | 487 | L | HD1 | H | 1 | 0.778 | 1 |
| 339 | 487 | L | HD2 | H | 1 | 0.829 | 1 |
| 340 | 487 | L | N | N | 15 | 121.648 | 1 |
| 341 | 489 | S | CA | C | 13 | 57.732 | 1 |
| 342 | 489 | S | CB | C | 13 | 63.976 | 1 |
| 343 | 489 | S | CO | C | 13 | 175.307 | 1 |
| 344 | 489 | S | H | H | 1 | 9.146 | 1 |
| 345 | 489 | S | N | N | 15 | 117.954 | 1 |
| 346 | 490 | V | CA | C | 13 | 59.96 | 1 |
| 347 | 490 | V | CB | C | 13 | 36.725 | 1 |
| 348 | 490 | V | CG1 | C | 13 | 21.034 | 1 |
| 349 | 490 | V | CG2 | C | 13 | 23.035 | 1 |
| 350 | 490 | V | CO | C | 13 | 175.445 | 1 |
| 351 | 490 | V | H | H | 1 | 7.378 | 1 |
| 352 | 490 | V | HG1 | H | 1 | 0.555 | 1 |
| 353 | 490 | V | HG2 | H | 1 | 0.885 | 1 |
| 354 | 490 | V | N | N | 15 | 118.616 | 1 |
| 355 | 491 | H | CA | C | 13 | 56.457 | 1 |
| 356 | 491 | H | CB | C | 13 | 33.175 | 1 |
| 357 | 491 | H | CO | C | 13 | 172.689 | 1 |
| 358 | 491 | H | H | H | 1 | 8.824 | 1 |
| 359 | 491 | H | N | N | 15 | 124.16 | 1 |
| 360 | 492 | A | CA | C | 13 | 48.933 | 1 |
| 361 | 492 | A | CB | C | 13 | 20.637 | 1 |
| 362 | 492 | A | CO | C | 13 | 175.149 | 1 |
| 363 | 492 | A | H | H | 1 | 7.475 | 1 |
| 364 | 492 | A | N | N | 15 | 129.587 | 1 |
| 365 | 493 | F | CA | C | 13 | 57.443 | 1 |
| 366 | 493 | F | CB | C | 13 | 40.032 | 1 |
| 367 | 493 | F | H | H | 1 | 8.075 | 1 |
| 368 | 493 | F | N | N | 15 | 120.292 | 1 |
| 369 | 494 | N | CA | C | 13 | 52.612 | 1 |
| 370 | 494 | N | CB | C | 13 | 39.014 | 1 |
| 371 | 494 | N | CO | C | 13 | 177.042 | 1 |
| 372 | 494 | N | H | H | 1 | 8.614 | 1 |
| 373 | 494 | N | N | N | 15 | 116.324 | 1 |
| 374 | 495 | T | CA | C | 13 | 65.108 | 1 |
| 375 | 495 | T | CB | C | 13 | 67.954 | 1 |
| 376 | 495 | T | H | H | 1 | 8.712 | 1 |
| 377 | 495 | T | N | N | 15 | 111.881 | 1 |
| 378 | 496 | F | CA | C | 13 | 57.589 | 1 |
| 379 | 496 | F | CB | C | 13 | 38.722 | 1 |
| 380 | 496 | F | CO | C | 13 | 176.791 | 1 |
| 381 | 496 | F | H | H | 1 | 8.441 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| 382 | 496 | F | N | N | 15 | 120.392 | 1 |
| 383 | 497 | F | CA | C | 13 | 61.468 | 1 |
| 384 | 497 | F | CB | C | 13 | 38.442 | 1 |
| 385 | 497 | F | CO | C | 13 | 175.62 | 1 |
| 386 | 497 | F | H | H | 1 | 7.951 | 1 |
| 387 | 497 | F | N | N | 15 | 121.386 | 1 |
| 388 | 498 | F | CA | C | 13 | 62.45 | 1 |
| 389 | 498 | F | CB | C | 13 | 37.649 | 1 |
| 390 | 498 | F | CO | C | 13 | 176.151 | 1 |
| 391 | 498 | F | H | H | 1 | 10.059 | 1 |
| 392 | 498 | F | N | N | 15 | 120.473 | 1 |
| 393 | 499 | T | CA | C | 13 | 65.751 | 1 |
| 394 | 499 | T | CB | C | 13 | 68.656 | 1 |
| 395 | 499 | T | H | H | 1 | 7.099 | 1 |
| 396 | 499 | T | N | N | 15 | 111.797 | 1 |
| 397 | 500 | K | CA | C | 13 | 58.082 | 1 |
| 398 | 500 | K | CB | C | 13 | 30.293 | 1 |
| 399 | 500 | K | CO | C | 13 | 177.17 | 1 |
| 400 | 500 | K | H | H | 1 | 7.805 | 1 |
| 401 | 500 | K | N | N | 15 | 122.907 | 1 |
| 402 | 501 | L | CA | C | 13 | 56.922 | 1 |
| 403 | 501 | L | CB | C | 13 | 40.32 | 1 |
| 404 | 501 | L | CD1 | C | 13 | 21.344 | 1 |
| 405 | 501 | L | CD2 | C | 13 | 26.13 | 1 |
| 406 | 501 | L | H | H | 1 | 8.04 | 1 |
| 407 | 501 | L | HD1 | H | 1 | 0.619 | 1 |
| 408 | 501 | L | HD2 | H | 1 | 0.269 | 1 |
| 409 | 501 | L | N | N | 15 | 120.722 | 1 |
| 410 | 502 | K | CA | C | 13 | 58.359 | 1 |
| 411 | 502 | K | CB | C | 13 | 31.117 | 1 |
| 412 | 502 | K | CO | C | 13 | 177.542 | 1 |
| 413 | 502 | K | H | H | 1 | 8.113 | 1 |
| 414 | 502 | K | N | N | 15 | 117.113 | 1 |
| 415 | 503 | T | CA | C | 13 | 63.65 | 1 |
| 416 | 503 | T | CB | C | 13 | 69.641 | 1 |
| 417 | 503 | T | CO | C | 13 | 175.362 | 1 |
| 418 | 503 | T | H | H | 1 | 7.521 | 1 |
| 419 | 503 | T | N | N | 15 | 108.626 | 1 |
| 420 | 504 | A | CA | C | 13 | 51.681 | 1 |
| 421 | 504 | A | CB | C | 13 | 19.982 | 1 |
| 422 | 504 | A | CO | C | 13 | 177.923 | 1 |
| 423 | 504 | A | H | H | 1 | 8.417 | 1 |
| 424 | 504 | A | N | N | 15 | 124.229 | 1 |
| 425 | 505 | G | CA | C | 13 | 44.062 | 1 |
| 426 | 505 | G | CO | C | 13 | 173.703 | 1 |
| 427 | 505 | G | H | H | 1 | 7.404 | 1 |
| 428 | 505 | G | N | N | 15 | 108.216 | 1 |
| 429 | 506 | Y | CA | C | 13 | 61.372 | 1 |
| 430 | 506 | Y | CB | C | 13 | 38.185 | 1 |
| 431 | 506 | Y | CO | C | 13 | 177.707 | 1 |
| 432 | 506 | Y | H | H | 1 | 8.506 | 1 |
| 433 | 506 | Y | N | N | 15 | 118.015 | 1 |
| 434 | 507 | Q | CA | C | 13 | 58.073 | 1 |
| 435 | 507 | Q | CB | C | 13 | 26.321 | 1 |
| 436 | 507 | Q | CO | C | 13 | 177.318 | 1 |
| 437 | 507 | Q | H | H | 1 | 8.677 | 1 |
| 438 | 507 | Q | N | N | 15 | 113.949 | 1 |
| 439 | 508 | A | CA | C | 13 | 53.059 | 1 |
| 440 | 508 | A | CB | C | 13 | 19.41 | 1 |
| 441 | 508 | A | CO | C | 13 | 178.474 | 1 |
| 442 | 508 | A | H | H | 1 | 7.193 | 1 |
| 443 | 508 | A | N | N | 15 | 117.81 | 1 |
| 444 | 509 | V | CA | C | 13 | 59.584 | 1 |
| 445 | 509 | V | CB | C | 13 | 32.636 | 1 |
| 446 | 509 | V | CG1 | C | 13 | 19.036 | 1 |
| 447 | 509 | V | CG2 | C | 13 | 20.077 | 1 |
| 448 | 509 | V | CO | C | 13 | 178.833 | 1 |
| 449 | 509 | V | H | H | 1 | 6.99 | 1 |
| 450 | 509 | V | HG1 | H | 1 | 0.152 | 1 |
| 451 | 509 | V | HG2 | H | 1 | 0.505 | 1 |
| 452 | 509 | V | N | N | 15 | 104.928 | 1 |
| 453 | 510 | K | CA | C | 13 | 59.235 | 1 |
| 454 | 510 | K | CB | C | 13 | 30.396 | 1 |
| 455 | 510 | K | CO | C | 13 | 178.002 | 1 |
| 456 | 510 | K | H | H | 1 | 7.252 | 1 |
| 457 | 510 | K | N | N | 15 | 126.565 | 1 |
| 458 | 511 | R | CA | C | 13 | 56.969 | 1 |
| 459 | 511 | R | CB | C | 13 | 28.393 | 1 |
| 460 | 511 | R | H | H | 1 | 8.593 | 1 |
| 461 | 511 | R | N | N | 15 | 116.236 | 1 |
| 462 | 512 | W | CA | C | 13 | 59.154 | 1 |
| 463 | 512 | W | CB | C | 13 | 27.825 | 1 |
| 464 | 512 | W | CO | C | 13 | 178.179 | 1 |
| 465 | 512 | W | H | H | 1 | 8.477 | 1 |
| 466 | 512 | W | HE1 | H | 1 | 10.293 | 1 |
| 467 | 512 | W | N | N | 15 | 120.092 | 1 |
| 468 | 512 | W | NE1 | N | 15 | 129.338 | 1 |
| 469 | 513 | T | CA | C | 13 | 60 | 1 |
| 470 | 513 | T | CB | C | 13 | 65.562 | 1 |
| 471 | 513 | T | CO | C | 13 | 174.181 | 1 |
| 472 | 513 | T | H | H | 1 | 7.356 | 1 |
| 473 | 513 | T | N | N | 15 | 105.836 | 1 |
| 474 | 514 | K | CA | C | 13 | 59.285 | 1 |
| 475 | 514 | K | CB | C | 13 | 31.488 | 1 |
| 476 | 514 | K | CO | C | 13 | 177.271 | 1 |
| 477 | 514 | K | H | H | 1 | 7.187 | 1 |
| 478 | 514 | K | N | N | 15 | 120.77 | 1 |
| 479 | 515 | K | CA | C | 13 | 55.075 | 1 |
| 480 | 515 | K | CB | C | 13 | 31.34 | 1 |
| 481 | 515 | K | CO | C | 13 | 175.55 | 1 |
| 482 | 515 | K | H | H | 1 | 8.52 | 1 |
| 483 | 515 | K | N | N | 15 | 115.267 | 1 |
| 484 | 516 | V | CA | C | 13 | 60.315 | 1 |
| 485 | 516 | V | CB | C | 13 | 34.794 | 1 |
| 486 | 516 | V | CG1 | C | 13 | 22.213 | 1 |
| 487 | 516 | V | CG2 | C | 13 | 19.431 | 1 |
| 488 | 516 | V | CO | C | 13 | 173.373 | 1 |
| 489 | 516 | V | H | H | 1 | 7.346 | 1 |
| 490 | 516 | V | HG1 | H | 1 | 1.035 | 1 |
| 491 | 516 | V | HG2 | H | 1 | 0.828 | 1 |
| 492 | 516 | V | N | N | 15 | 118.521 | 1 |
| 493 | 517 | D | CA | C | 13 | 50.719 | 1 |
| 494 | 517 | D | CB | C | 13 | 39.298 | 1 |
| 495 | 517 | D | CO | C | 13 | 178.171 | 1 |
| 496 | 517 | D | H | H | 1 | 8.502 | 1 |
| 497 | 517 | D | N | N | 15 | 124.325 | 1 |
| 498 | 518 | V | CA | C | 13 | 64.12 | 1 |
| 499 | 518 | V | CB | C | 13 | 30.53 | 1 |
| 500 | 518 | V | CG1 | C | 13 | 21.974 | 1 |
| 501 | 518 | V | CG2 | C | 13 | 17.74 | 1 |
| 502 | 518 | V | CO | C | 13 | 173.205 | 1 |
| 503 | 518 | V | H | H | 1 | 8.909 | 1 |
| 504 | 518 | V | HG1 | H | 1 | 0.709 | 1 |
| 505 | 518 | V | HG2 | H | 1 | 0.246 | 1 |
| 506 | 518 | V | N | N | 15 | 121.419 | 1 |
| 507 | 519 | F | CA | C | 13 | 57.9 | 1 |
| 508 | 519 | F | CB | C | 13 | 36.872 | 1 |
| 509 | 519 | F | CO | C | 13 | 176.5 | 1 |
| 510 | 519 | F | H | H | 1 | 7.223 | 1 |
| 511 | 519 | F | N | N | 15 | 110.893 | 1 |
| 512 | 520 | S | CB | C | 13 | 64.082 | 1 |
| 513 | 520 | S | CO | C | 13 | 173.635 | 1 |
| 514 | 520 | S | H | H | 1 | 7.457 | 1 |
| 515 | 520 | S | N | N | 15 | 113.527 | 1 |
| 516 | 521 | V | CA | C | 13 | 58.421 | 1 |
| 517 | 521 | V | CB | C | 13 | 33.049 | 1 |
| 518 | 521 | V | CG1 | C | 13 | 21.474 | 1 |
| 519 | 521 | V | CG2 | C | 13 | 19.203 | 1 |
| 520 | 521 | V | CO | C | 13 | 174.363 | 1 |
| 521 | 521 | V | H | H | 1 | 6.675 | 1 |
| 522 | 521 | V | HG1 | H | 1 | 0.677 | 1 |
| 523 | 521 | V | HG2 | H | 1 | 0.736 | 1 |
| 524 | 521 | V | N | N | 15 | 114.244 | 1 |
| 525 | 522 | D | CA | C | 13 | 57.671 | 1 |
| 526 | 522 | D | CB | C | 13 | 42.241 | 1 |
| 527 | 522 | D | H | H | 1 | 8.177 | 1 |
| 528 | 522 | D | N | N | 15 | 120.102 | 1 |
| 529 | 523 | I | CA | C | 13 | 59.234 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 530 | 523 | I | H | H | 1 | 8.209 | 1 |
| 531 | 523 | I | N | N | 15 | 117.31 | 1 |
| 532 | 524 | L | CA | C | 13 | 51.912 | 1 |
| 533 | 524 | L | CB | C | 13 | 42.117 | 1 |
| 534 | 524 | L | CD1 | C | 13 | 24.261 | 2 |
| 535 | 524 | L | CD2 | C | 13 | 24.458 | 2 |
| 536 | 524 | L | H | H | 1 | 9.357 | 1 |
| 537 | 524 | L | HD1 | H | 1 | 0.826 | 2 |
| 538 | 524 | L | HD2 | H | 1 | 0.873 | 2 |
| 539 | 524 | L | N | N | 15 | 121.905 | 1 |
| 540 | 525 | L | CA | C | 13 | 53.109 | 1 |
| 541 | 525 | L | CB | C | 13 | 43.667 | 1 |
| 542 | 525 | L | CD1 | C | 13 | 27.473 | 1 |
| 543 | 525 | L | CD2 | C | 13 | 23.613 | 1 |
| 544 | 525 | L | H | H | 1 | 8.708 | 1 |
| 545 | 525 | L | HD1 | H | 1 | 0.737 | 1 |
| 546 | 525 | L | HD2 | H | 1 | 0.713 | 1 |
| 547 | 525 | L | N | N | 15 | 120.45 | 1 |
| 548 | 526 | V | CA | C | 13 | 59.564 | 1 |
| 549 | 526 | V | CB | C | 13 | 32.337 | 1 |
| 550 | 526 | V | CG1 | C | 13 | 20.681 | 1 |
| 551 | 526 | V | CG2 | C | 13 | 19.401 | 1 |
| 552 | 526 | V | H | H | 1 | 8.925 | 1 |
| 553 | 526 | V | HG1 | H | 1 | −0.236 | 1 |
| 554 | 526 | V | HG2 | H | 1 | 0.488 | 1 |
| 555 | 526 | V | N | N | 15 | 120.847 | 1 |
| 556 | 528 | I | CA | C | 13 | 60.95 | 1 |
| 557 | 528 | I | CB | C | 13 | 39.801 | 1 |
| 558 | 528 | I | H | H | 1 | 8.737 | 1 |
| 559 | 528 | I | N | N | 15 | 125.023 | 1 |
| 560 | 529 | H | CA | C | 13 | 50.979 | 1 |
| 561 | 529 | H | CB | C | 13 | 29.375 | 1 |
| 562 | 529 | H | CO | C | 13 | 174.067 | 1 |
| 563 | 529 | H | H | H | 1 | 9.036 | 1 |
| 564 | 529 | H | N | N | 15 | 129.849 | 1 |
| 565 | 530 | L | CA | C | 13 | 52.799 | 1 |
| 566 | 530 | L | CB | C | 13 | 41.01 | 1 |
| 567 | 530 | L | CD1 | C | 13 | 25.841 | 1 |
| 568 | 530 | L | CD2 | C | 13 | 23.767 | 1 |
| 569 | 530 | L | CO | C | 13 | 176.318 | 1 |
| 570 | 530 | L | H | H | 1 | 8.525 | 1 |
| 571 | 530 | L | HD1 | H | 1 | 0.874 | 1 |
| 572 | 530 | L | HD2 | H | 1 | 0.77 | 1 |
| 573 | 530 | L | N | N | 15 | 130.501 | 1 |
| 574 | 531 | G | CA | C | 13 | 46.001 | 1 |
| 575 | 531 | G | CO | C | 13 | 174.79 | 1 |
| 576 | 531 | G | H | H | 1 | 8.157 | 1 |
| 577 | 531 | G | N | N | 15 | 115.336 | 1 |
| 578 | 532 | V | CA | C | 13 | 61.094 | 1 |
| 579 | 532 | V | CB | C | 13 | 30.784 | 1 |
| 580 | 532 | V | CG1 | C | 13 | 20.964 | 1 |
| 581 | 532 | V | CG2 | C | 13 | 18.117 | 1 |
| 582 | 532 | V | CO | C | 13 | 175.461 | 1 |
| 583 | 532 | V | H | H | 1 | 8.198 | 1 |
| 584 | 532 | V | HG1 | H | 1 | 0.532 | 1 |
| 585 | 532 | V | HG2 | H | 1 | 0.584 | 1 |
| 586 | 532 | V | N | N | 15 | 119.81 | 1 |
| 587 | 533 | H | CA | C | 13 | 55.28 | 1 |
| 588 | 533 | H | CB | C | 13 | 32.996 | 1 |
| 589 | 533 | H | CO | C | 13 | 174.498 | 1 |
| 590 | 533 | H | H | H | 1 | 7.803 | 1 |
| 591 | 533 | H | N | N | 15 | 121.771 | 1 |
| 592 | 534 | W | CA | C | 13 | 55.915 | 1 |
| 593 | 534 | W | CB | C | 13 | 32.49 | 1 |
| 594 | 534 | W | H | H | 1 | 6.407 | 1 |
| 595 | 534 | W | HE1 | H | 1 | 9.377 | 1 |
| 596 | 534 | W | N | N | 15 | 125.3 | 1 |
| 597 | 534 | W | NE1 | N | 15 | 128.192 | 1 |
| 598 | 535 | C | CA | C | 13 | 56.548 | 1 |
| 599 | 535 | C | CB | C | 13 | 30.615 | 1 |
| 600 | 535 | C | CO | C | 13 | 171.965 | 1 |
| 601 | 535 | C | H | H | 1 | 9.461 | 1 |
| 602 | 535 | C | N | N | 15 | 117.22 | 1 |
| 603 | 536 | L | CA | C | 13 | 54.008 | 1 |
| 604 | 536 | L | CB | C | 13 | 46.487 | 1 |
| 605 | 536 | L | CD1 | C | 13 | 22.301 | 1 |
| 606 | 536 | L | CD2 | C | 13 | 26.282 | 1 |
| 607 | 536 | L | H | H | 1 | 7.905 | 1 |
| 608 | 536 | L | HD1 | H | 1 | 0.679 | 1 |
| 609 | 536 | L | HD2 | H | 1 | 0.597 | 1 |
| 610 | 536 | L | N | N | 15 | 120.825 | 1 |
| 611 | 537 | A | CA | C | 13 | 49.576 | 1 |
| 612 | 537 | A | CB | C | 13 | 20.964 | 1 |
| 613 | 537 | A | H | H | 1 | 8.835 | 1 |
| 614 | 537 | A | N | N | 15 | 126.773 | 1 |
| 615 | 538 | V | CA | C | 13 | 60.449 | 1 |
| 616 | 538 | V | CB | C | 13 | 35.413 | 1 |
| 617 | 538 | V | CG1 | C | 13 | 21.698 | 1 |
| 618 | 538 | V | CG2 | C | 13 | 21.913 | 1 |
| 619 | 538 | V | CO | C | 13 | 174.727 | 1 |
| 620 | 538 | V | H | H | 1 | 9.071 | 1 |
| 621 | 538 | V | HG1 | H | 1 | 0.87 | 1 |
| 622 | 538 | V | HG2 | H | 1 | 0.809 | 1 |
| 623 | 538 | V | N | N | 15 | 119.546 | 1 |
| 624 | 539 | V | CA | C | 13 | 60.873 | 1 |
| 625 | 539 | V | CB | C | 13 | 32.053 | 1 |
| 626 | 539 | V | CG1 | C | 13 | 20.502 | 1 |
| 627 | 539 | V | CG2 | C | 13 | 19.475 | 1 |
| 628 | 539 | V | H | H | 1 | 9.402 | 1 |
| 629 | 539 | V | HG1 | H | 1 | 0.441 | 1 |
| 630 | 539 | V | HG2 | H | 1 | 0.881 | 1 |
| 631 | 539 | V | N | N | 15 | 130.501 | 1 |
| 632 | 540 | D | CA | C | 13 | 51.922 | 1 |
| 633 | 540 | D | CB | C | 13 | 41.816 | 1 |
| 634 | 540 | D | H | H | 1 | 8.954 | 1 |
| 635 | 540 | D | N | N | 15 | 126.546 | 1 |
| 636 | 541 | F | CA | C | 13 | 62.022 | 1 |
| 637 | 541 | F | CB | C | 13 | 39.187 | 1 |
| 638 | 541 | F | H | H | 1 | 9.479 | 1 |
| 639 | 541 | F | N | N | 15 | 123.936 | 1 |
| 640 | 542 | R | CA | C | 13 | 57.3 | 1 |
| 641 | 542 | R | CB | C | 13 | 28.607 | 1 |
| 642 | 542 | R | CO | C | 13 | 179.074 | 1 |
| 643 | 542 | R | H | H | 1 | 8.714 | 1 |
| 644 | 542 | R | N | N | 15 | 117.561 | 1 |
| 645 | 543 | K | CA | C | 13 | 54.808 | 1 |
| 646 | 543 | K | CB | C | 13 | 33.288 | 1 |
| 647 | 543 | K | CO | C | 13 | 175.221 | 1 |
| 648 | 543 | K | H | H | 1 | 6.749 | 1 |
| 649 | 543 | K | N | N | 15 | 114.224 | 1 |
| 650 | 544 | K | CA | C | 13 | 55.562 | 1 |
| 651 | 544 | K | CB | C | 13 | 27.641 | 1 |
| 652 | 544 | K | CO | C | 13 | 175.247 | 1 |
| 653 | 544 | K | H | H | 1 | 7.423 | 1 |
| 654 | 544 | K | N | N | 15 | 115.776 | 1 |
| 655 | 545 | N | CA | C | 13 | 51.023 | 1 |
| 656 | 545 | N | CB | C | 13 | 42.123 | 1 |
| 657 | 545 | N | CO | C | 13 | 173.859 | 1 |
| 658 | 545 | N | H | H | 1 | 7.23 | 1 |
| 659 | 545 | N | N | N | 15 | 113.498 | 1 |
| 660 | 546 | I | CA | C | 13 | 61.517 | 1 |
| 661 | 546 | I | H | H | 1 | 8.432 | 1 |
| 662 | 546 | I | N | N | 15 | 120.288 | 1 |
| 663 | 547 | T | CA | C | 13 | 60.921 | 1 |
| 664 | 547 | T | CB | C | 13 | 70.493 | 1 |
| 665 | 547 | T | H | H | 1 | 8.781 | 1 |
| 666 | 547 | T | N | N | 15 | 121.352 | 1 |
| 667 | 548 | Y | CA | C | 13 | 57.227 | 1 |
| 668 | 548 | Y | CB | C | 13 | 40.796 | 1 |
| 669 | 548 | Y | H | H | 1 | 8.727 | 1 |
| 670 | 548 | Y | N | N | 15 | 128.981 | 1 |
| 671 | 549 | Y | CB | C | 13 | 40.072 | 1 |
| 672 | 549 | Y | H | H | 1 | 9.079 | 1 |
| 673 | 549 | Y | N | N | 15 | 125.239 | 1 |
| 674 | 550 | D | CA | C | 13 | 52.549 | 1 |
| 675 | 550 | D | CB | C | 13 | 43.937 | 1 |
| 676 | 550 | D | CO | C | 13 | 177.444 | 1 |
| 677 | 550 | D | H | H | 1 | 8.116 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 678 | 550 | D | N | N | 15 | 123.169 | 1 |
| 679 | 551 | S | CA | C | 13 | 60.463 | 1 |
| 680 | 551 | S | CB | C | 13 | 62.962 | 1 |
| 681 | 551 | S | CO | C | 13 | 174.422 | 1 |
| 682 | 551 | S | H | H | 1 | 9.519 | 1 |
| 683 | 551 | S | N | N | 15 | 122.969 | 1 |
| 684 | 552 | M | CA | C | 13 | 54.901 | 1 |
| 685 | 552 | M | CB | C | 13 | 34.489 | 1 |
| 686 | 552 | M | CO | C | 13 | 178.972 | 1 |
| 687 | 552 | M | H | H | 1 | 9.32 | 1 |
| 688 | 552 | M | N | N | 15 | 122.574 | 1 |
| 689 | 553 | G | CA | C | 13 | 46.475 | 1 |
| 690 | 553 | G | CO | C | 13 | 175.385 | 1 |
| 691 | 553 | G | H | H | 1 | 7.89 | 1 |
| 692 | 553 | G | N | N | 15 | 109.507 | 1 |
| 693 | 554 | G | CA | C | 13 | 44.928 | 1 |
| 694 | 554 | G | CO | C | 13 | 171.658 | 1 |
| 695 | 554 | G | H | H | 1 | 7.51 | 1 |
| 696 | 554 | G | N | N | 15 | 107.555 | 1 |
| 697 | 555 | I | CA | C | 13 | 59.215 | 1 |
| 698 | 555 | I | CB | C | 13 | 37.955 | 1 |
| 699 | 555 | I | CO | C | 13 | 176.285 | 1 |
| 700 | 555 | I | H | H | 1 | 8.05 | 1 |
| 701 | 555 | I | N | N | 15 | 118.138 | 1 |
| 702 | 556 | N | CA | C | 13 | 50.688 | 1 |
| 703 | 556 | N | CB | C | 13 | 36.209 | 1 |
| 704 | 556 | N | H | H | 1 | 7.762 | 1 |
| 705 | 556 | N | N | N | 15 | 124.106 | 1 |
| 706 | 557 | N | CA | C | 13 | 55.66 | 1 |
| 707 | 557 | N | CB | C | 13 | 37.225 | 1 |
| 708 | 557 | N | H | H | 1 | 8.339 | 1 |
| 709 | 557 | N | N | N | 15 | 121.312 | 1 |
| 710 | 558 | E | CA | C | 13 | 59.21 | 1 |
| 711 | 558 | E | CB | C | 13 | 28.223 | 1 |
| 712 | 558 | E | H | H | 1 | 8.531 | 1 |
| 713 | 558 | E | N | N | 15 | 120.721 | 1 |
| 714 | 559 | A | CA | C | 13 | 55.072 | 1 |
| 715 | 559 | A | CB | C | 13 | 17.209 | 1 |
| 716 | 559 | A | CO | C | 13 | 179.228 | 1 |
| 717 | 559 | A | H | H | 1 | 7.491 | 1 |
| 718 | 559 | A | N | N | 15 | 120.499 | 1 |
| 719 | 560 | C | CA | C | 13 | 61.861 | 1 |
| 720 | 560 | C | CB | C | 13 | 26.362 | 1 |
| 721 | 560 | C | CO | C | 13 | 176.152 | 1 |
| 722 | 560 | C | H | H | 1 | 6.803 | 1 |
| 723 | 560 | C | N | N | 15 | 111.946 | 1 |
| 724 | 561 | R | CA | C | 13 | 59.736 | 1 |
| 725 | 561 | R | CB | C | 13 | 29.122 | 1 |
| 726 | 561 | R | CO | C | 13 | 179.458 | 1 |
| 727 | 561 | R | H | H | 1 | 8.077 | 1 |
| 728 | 561 | R | N | N | 15 | 120.238 | 1 |
| 729 | 562 | I | CA | C | 13 | 64.773 | 1 |
| 730 | 562 | I | CB | C | 13 | 36.965 | 1 |
| 731 | 562 | I | CO | C | 13 | 179.283 | 1 |
| 732 | 562 | I | H | H | 1 | 8.583 | 1 |
| 733 | 562 | I | N | N | 15 | 120.588 | 1 |
| 734 | 563 | L | CA | C | 13 | 56.989 | 1 |
| 735 | 563 | L | CB | C | 13 | 41.139 | 1 |
| 736 | 563 | L | CD1 | C | 13 | 26.07 | 1 |
| 737 | 563 | L | CD2 | C | 13 | 22.794 | 1 |
| 738 | 563 | L | CO | C | 13 | 177.668 | 1 |
| 739 | 563 | L | H | H | 1 | 7.58 | 1 |
| 740 | 563 | L | HD1 | H | 1 | 0.714 | 1 |
| 741 | 563 | L | HD2 | H | 1 | 0.791 | 1 |
| 742 | 563 | L | N | N | 15 | 120.645 | 1 |
| 743 | 564 | L | CA | C | 13 | 57.863 | 1 |
| 744 | 564 | L | CB | C | 13 | 40.586 | 1 |
| 745 | 564 | L | CD1 | C | 13 | 23.029 | 1 |
| 746 | 564 | L | CD2 | C | 13 | 25.722 | 1 |
| 747 | 564 | L | H | H | 1 | 7.989 | 1 |
| 748 | 564 | L | HD1 | H | 1 | 0.503 | 1 |
| 749 | 564 | L | HD2 | H | 1 | 0.873 | 1 |
| 750 | 564 | L | N | N | 15 | 122.277 | 1 |
| 751 | 565 | Q | CB | C | 13 | 27.023 | 1 |
| 752 | 565 | Q | CO | C | 13 | 178.554 | 1 |
| 753 | 565 | Q | H | H | 1 | 7.945 | 1 |
| 754 | 565 | Q | N | N | 15 | 116.169 | 1 |
| 755 | 566 | Y | CA | C | 13 | 61.262 | 1 |
| 756 | 566 | Y | CB | C | 13 | 36.89 | 1 |
| 757 | 566 | Y | H | H | 1 | 8.147 | 1 |
| 758 | 566 | Y | N | N | 15 | 121.414 | 1 |
| 759 | 567 | L | CA | C | 13 | 57.69 | 1 |
| 760 | 567 | L | CB | C | 13 | 39.693 | 1 |
| 761 | 567 | L | CD1 | C | 13 | 26.027 | 1 |
| 762 | 567 | L | CD2 | C | 13 | 21.698 | 1 |
| 763 | 567 | L | H | H | 1 | 7.756 | 1 |
| 764 | 567 | L | HD1 | H | 1 | 0.298 | 1 |
| 765 | 567 | L | HD2 | H | 1 | 0.574 | 1 |
| 766 | 567 | L | N | N | 15 | 118.927 | 1 |
| 767 | 568 | K | CA | C | 13 | 59.666 | 1 |
| 768 | 568 | K | CB | C | 13 | 31.072 | 1 |
| 769 | 568 | K | CO | C | 13 | 180.159 | 1 |
| 770 | 568 | K | H | H | 1 | 7.436 | 1 |
| 771 | 568 | K | N | N | 15 | 116.321 | 1 |
| 772 | 569 | Q | CA | C | 13 | 58.376 | 1 |
| 773 | 569 | Q | CB | C | 13 | 26.837 | 1 |
| 774 | 569 | Q | CO | C | 13 | 178.121 | 1 |
| 775 | 569 | Q | H | H | 1 | 7.71 | 1 |
| 776 | 569 | Q | N | N | 15 | 119.281 | 1 |
| 777 | 570 | E | CA | C | 13 | 57.248 | 1 |
| 778 | 570 | E | CB | C | 13 | 27.85 | 1 |
| 779 | 570 | E | CO | C | 13 | 178.511 | 1 |
| 780 | 570 | E | H | H | 1 | 8.874 | 1 |
| 781 | 570 | E | N | N | 15 | 123.757 | 1 |
| 782 | 571 | S | CA | C | 13 | 61.824 | 1 |
| 783 | 571 | S | CB | C | 13 | 63.591 | 1 |
| 784 | 571 | S | H | H | 1 | 8.112 | 1 |
| 785 | 571 | S | N | N | 15 | 113.072 | 1 |
| 786 | 572 | I | CA | C | 13 | 64.046 | 1 |
| 787 | 572 | I | CB | C | 13 | 36.762 | 1 |
| 788 | 572 | I | CO | C | 13 | 178.898 | 1 |
| 789 | 572 | I | H | H | 1 | 7.085 | 1 |
| 790 | 572 | I | N | N | 15 | 120.025 | 1 |
| 791 | 573 | D | CA | C | 13 | 58.589 | 1 |
| 792 | 573 | D | CB | C | 13 | 45.295 | 1 |
| 793 | 573 | D | H | H | 1 | 8.267 | 1 |
| 794 | 573 | D | N | N | 15 | 119.596 | 1 |
| 795 | 574 | K | CA | C | 13 | 55.261 | 1 |
| 796 | 574 | K | H | H | 1 | 8.537 | 1 |
| 797 | 574 | K | N | N | 15 | 110.111 | 1 |
| 798 | 575 | K | CA | C | 13 | 53.6 | 1 |
| 799 | 575 | K | H | H | 1 | 7.814 | 1 |
| 800 | 575 | K | N | N | 15 | 114.921 | 1 |
| 801 | 580 | D | CA | C | 13 | 53.108 | 1 |
| 802 | 580 | D | CO | C | 13 | 175.974 | 1 |
| 803 | 580 | D | H | H | 1 | 8.008 | 1 |
| 804 | 580 | D | N | N | 15 | 128.24 | 1 |
| 805 | 581 | T | CA | C | 13 | 61.607 | 1 |
| 806 | 581 | T | CB | C | 13 | 67.992 | 1 |
| 807 | 581 | T | CO | C | 13 | 176.37 | 1 |
| 808 | 581 | T | H | H | 1 | 8.005 | 1 |
| 809 | 581 | T | N | N | 15 | 114.488 | 1 |
| 810 | 582 | N | CA | C | 13 | 55.671 | 1 |
| 811 | 582 | N | CB | C | 13 | 37.704 | 1 |
| 812 | 582 | N | CO | C | 13 | 177.026 | 1 |
| 813 | 582 | N | H | H | 1 | 8.559 | 1 |
| 814 | 582 | N | N | N | 15 | 124.721 | 1 |
| 815 | 583 | G | CA | C | 13 | 45.005 | 1 |
| 816 | 583 | G | CO | C | 13 | 174.64 | 1 |
| 817 | 583 | G | H | H | 1 | 8.964 | 1 |
| 818 | 583 | G | N | N | 15 | 113.066 | 1 |
| 819 | 584 | W | CA | C | 13 | 58.735 | 1 |
| 820 | 584 | W | CB | C | 13 | 27.343 | 1 |
| 821 | 584 | W | CO | C | 13 | 177.331 | 1 |
| 822 | 584 | W | H | H | 1 | 7.891 | 1 |
| 823 | 584 | W | HE1 | H | 1 | 10.207 | 1 |
| 824 | 584 | W | N | N | 15 | 120.551 | 1 |
| 825 | 584 | W | NE1 | N | 15 | 130.072 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 826 | 585 | Q | CA | C | 13 | 54.336 | 1 |
| 827 | 585 | Q | CB | C | 13 | 32.617 | 1 |
| 828 | 585 | Q | CO | C | 13 | 173.396 | 1 |
| 829 | 585 | Q | H | H | 1 | 8.32 | 1 |
| 830 | 585 | Q | N | N | 15 | 120.47 | 1 |
| 831 | 586 | L | CA | C | 13 | 52.787 | 1 |
| 832 | 586 | L | CB | C | 13 | 41.572 | 1 |
| 833 | 586 | L | CD1 | C | 13 | 24.58 | 1 |
| 834 | 586 | L | CD2 | C | 13 | 24.177 | 1 |
| 835 | 586 | L | CO | C | 13 | 176.073 | 1 |
| 836 | 586 | L | H | H | 1 | 8.257 | 1 |
| 837 | 586 | L | HD1 | H | 1 | 0.875 | 1 |
| 838 | 586 | L | HD2 | H | 1 | 1.06 | 1 |
| 839 | 586 | L | N | N | 15 | 122.471 | 1 |
| 840 | 587 | F | CA | C | 13 | 56.274 | 1 |
| 841 | 587 | F | CB | C | 13 | 41.98 | 1 |
| 842 | 587 | F | CO | C | 13 | 174.71 | 1 |
| 843 | 587 | F | H | H | 1 | 9.007 | 1 |
| 844 | 587 | F | N | N | 15 | 119.628 | 1 |
| 845 | 588 | S | CA | C | 13 | 57.584 | 1 |
| 846 | 588 | S | CB | C | 13 | 64.741 | 1 |
| 847 | 588 | S | CO | C | 13 | 174.522 | 1 |
| 848 | 588 | S | H | H | 1 | 8.55 | 1 |
| 849 | 588 | S | N | N | 15 | 115.508 | 1 |
| 850 | 589 | K | CA | C | 13 | 54.504 | 1 |
| 851 | 589 | K | CB | C | 13 | 30.677 | 1 |
| 852 | 589 | K | CO | C | 13 | 176.928 | 1 |
| 853 | 589 | K | H | H | 1 | 8.375 | 1 |
| 854 | 589 | K | N | N | 15 | 123.879 | 1 |
| 855 | 590 | K | CA | C | 13 | 55.59 | 1 |
| 856 | 590 | K | CB | C | 13 | 32.654 | 1 |
| 857 | 590 | K | CO | C | 13 | 178.646 | 1 |
| 858 | 590 | K | H | H | 1 | 9.16 | 1 |
| 859 | 590 | K | N | N | 15 | 124.442 | 1 |
| 860 | 591 | S | CA | C | 13 | 60.73 | 1 |
| 861 | 591 | S | CB | C | 13 | 62.469 | 1 |
| 862 | 591 | S | CO | C | 13 | 175.07 | 1 |
| 863 | 591 | S | H | H | 1 | 8.771 | 1 |
| 864 | 591 | S | N | N | 15 | 116.878 | 1 |
| 865 | 592 | Q | CA | C | 13 | 56.481 | 1 |
| 866 | 592 | Q | CB | C | 13 | 27.319 | 1 |
| 867 | 592 | Q | CO | C | 13 | 177.119 | 1 |
| 868 | 592 | Q | H | H | 1 | 7.787 | 1 |
| 869 | 592 | Q | N | N | 15 | 114.421 | 1 |
| 870 | 593 | E | CA | C | 13 | 56.788 | 1 |
| 871 | 593 | E | CB | C | 13 | 31.514 | 1 |
| 872 | 593 | E | CO | C | 13 | 176.185 | 1 |
| 873 | 593 | E | H | H | 1 | 8.147 | 1 |
| 874 | 593 | E | N | N | 15 | 116.571 | 1 |
| 875 | 594 | I | CA | C | 13 | 57.233 | 1 |
| 876 | 594 | I | CB | C | 13 | 39.464 | 1 |
| 877 | 594 | I | H | H | 1 | 7.099 | 1 |
| 878 | 594 | I | N | N | 15 | 111.638 | 1 |
| 879 | 596 | Q | CA | C | 13 | 52.641 | 1 |
| 880 | 596 | Q | CB | C | 13 | 31.367 | 1 |
| 881 | 596 | Q | CO | C | 13 | 176.998 | 1 |
| 882 | 596 | Q | H | H | 1 | 8.568 | 1 |
| 883 | 596 | Q | N | N | 15 | 119.776 | 1 |
| 884 | 597 | Q | CA | C | 13 | 53.866 | 1 |
| 885 | 597 | Q | CB | C | 13 | 28.195 | 1 |
| 886 | 597 | Q | CO | C | 13 | 175.677 | 1 |
| 887 | 597 | Q | H | H | 1 | 8.67 | 1 |
| 888 | 597 | Q | N | N | 15 | 118.265 | 1 |
| 889 | 598 | M | CA | C | 13 | 55.496 | 1 |
| 890 | 598 | M | CB | C | 13 | 33.978 | 1 |
| 891 | 598 | M | CO | C | 13 | 175.887 | 1 |
| 892 | 598 | M | H | H | 1 | 9.45 | 1 |
| 893 | 598 | M | N | N | 15 | 118.496 | 1 |
| 894 | 599 | N | CA | C | 13 | 51.768 | 1 |
| 895 | 599 | N | CB | C | 13 | 39.114 | 1 |
| 896 | 599 | N | H | H | 1 | 7.565 | 1 |
| 897 | 599 | N | N | N | 15 | 117.184 | 1 |
| 898 | 600 | G | H | H | 1 | 9.054 | 1 |
| 899 | 600 | G | N | N | 15 | 114.081 | 1 |
| 900 | 601 | S | CA | C | 13 | 58.424 | 1 |
| 901 | 601 | S | CB | C | 13 | 60.647 | 1 |
| 902 | 601 | S | H | H | 1 | 7.855 | 1 |
| 903 | 601 | S | N | N | 15 | 114.866 | 1 |
| 904 | 602 | D | CA | C | 13 | 55.181 | 1 |
| 905 | 602 | D | CB | C | 13 | 40.81 | 1 |
| 906 | 602 | D | CO | C | 13 | 178.539 | 1 |
| 907 | 602 | D | H | H | 1 | 7.257 | 1 |
| 908 | 602 | D | N | N | 15 | 118.282 | 1 |
| 909 | 603 | C | CA | C | 13 | 60.678 | 1 |
| 910 | 603 | C | CB | C | 13 | 28.27 | 1 |
| 911 | 603 | C | CO | C | 13 | 175.783 | 1 |
| 912 | 603 | C | H | H | 1 | 7.715 | 1 |
| 913 | 603 | C | N | N | 15 | 121.968 | 1 |
| 914 | 604 | G | CA | C | 13 | 46.862 | 1 |
| 915 | 604 | G | CO | C | 13 | 175.076 | 1 |
| 916 | 604 | G | H | H | 1 | 8.736 | 1 |
| 917 | 604 | G | N | N | 15 | 109.643 | 1 |
| 918 | 605 | M | CA | C | 13 | 54.421 | 1 |
| 919 | 605 | M | CB | C | 13 | 28.885 | 1 |
| 920 | 605 | M | CO | C | 13 | 178.831 | 1 |
| 921 | 605 | M | H | H | 1 | 6.973 | 1 |
| 922 | 605 | M | N | N | 15 | 118.381 | 1 |
| 923 | 606 | F | CA | C | 13 | 63.186 | 1 |
| 924 | 606 | F | CB | C | 13 | 37.346 | 1 |
| 925 | 606 | F | CO | C | 13 | 175.928 | 1 |
| 926 | 606 | F | H | H | 1 | 8.265 | 1 |
| 927 | 606 | F | N | N | 15 | 118.962 | 1 |
| 928 | 607 | A | CA | C | 13 | 55.826 | 1 |
| 929 | 607 | A | CB | C | 13 | 15.841 | 1 |
| 930 | 607 | A | CO | C | 13 | 179.705 | 1 |
| 931 | 607 | A | H | H | 1 | 7.745 | 1 |
| 932 | 607 | A | N | N | 15 | 118.262 | 1 |
| 933 | 608 | C | CA | C | 13 | 64.555 | 1 |
| 934 | 608 | C | CB | C | 13 | 26.489 | 1 |
| 935 | 608 | C | CO | C | 13 | 176.344 | 1 |
| 936 | 608 | C | H | H | 1 | 7.15 | 1 |
| 937 | 608 | C | N | N | 15 | 111.327 | 1 |
| 938 | 609 | K | CA | C | 13 | 55.983 | 1 |
| 939 | 609 | K | CB | C | 13 | 28.003 | 1 |
| 940 | 609 | K | CO | C | 13 | 180.898 | 1 |
| 941 | 609 | K | H | H | 1 | 8.114 | 1 |
| 942 | 609 | K | N | N | 15 | 117.546 | 1 |
| 943 | 610 | Y | CA | C | 13 | 58.081 | 1 |
| 944 | 610 | Y | CB | C | 13 | 36.268 | 1 |
| 945 | 610 | Y | CO | C | 13 | 177.942 | 1 |
| 946 | 610 | Y | H | H | 1 | 9.584 | 1 |
| 947 | 610 | Y | N | N | 15 | 121.342 | 1 |
| 948 | 611 | A | CA | C | 13 | 55.284 | 1 |
| 949 | 611 | A | CB | C | 13 | 17.36 | 1 |
| 950 | 611 | A | CO | C | 13 | 179.296 | 1 |
| 951 | 611 | A | H | H | 1 | 7.3 | 1 |
| 952 | 611 | A | N | N | 15 | 118.235 | 1 |
| 953 | 612 | D | CA | C | 13 | 57.496 | 1 |
| 954 | 612 | D | CB | C | 13 | 40.809 | 1 |
| 955 | 612 | D | CO | C | 13 | 177.083 | 1 |
| 956 | 612 | D | H | H | 1 | 8.285 | 1 |
| 957 | 612 | D | N | N | 15 | 119.051 | 1 |
| 958 | 613 | C | CA | C | 13 | 64.249 | 1 |
| 959 | 613 | C | CB | C | 13 | 26.401 | 1 |
| 960 | 613 | C | CO | C | 13 | 177.033 | 1 |
| 961 | 613 | C | H | H | 1 | 7.283 | 1 |
| 962 | 613 | C | N | N | 15 | 114.15 | 1 |
| 963 | 614 | I | CA | C | 13 | 64.188 | 1 |
| 964 | 614 | I | CB | C | 13 | 38.287 | 1 |
| 965 | 614 | I | CO | C | 13 | 180.531 | 1 |
| 966 | 614 | I | H | H | 1 | 8.523 | 1 |
| 967 | 614 | I | N | N | 15 | 119.103 | 1 |
| 968 | 615 | T | CB | C | 13 | 67.658 | 1 |
| 969 | 615 | T | CO | C | 13 | 174.525 | 1 |
| 970 | 615 | T | H | H | 1 | 8.251 | 1 |
| 971 | 615 | T | N | N | 15 | 108.325 | 1 |
| 972 | 616 | K | CA | C | 13 | 55.419 | 1 |
| 973 | 616 | K | CB | C | 13 | 31.971 | 1 |

TABLE 3-continued

Free SENP1 NMR Chemical Shifts Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 974 | 616 | K | CO | C | 13 | 175.509 | 1 |
| 975 | 616 | K | H | H | 1 | 7.204 | 1 |
| 976 | 616 | K | N | N | 15 | 118.784 | 1 |
| 977 | 617 | D | CA | C | 13 | 55.028 | 1 |
| 978 | 617 | D | CB | C | 13 | 38.871 | 1 |
| 979 | 617 | D | CO | C | 13 | 174.882 | 1 |
| 980 | 617 | D | H | H | 1 | 7.982 | 1 |
| 981 | 617 | D | N | N | 15 | 117.696 | 1 |
| 982 | 618 | R | CA | C | 13 | 51.906 | 1 |
| 983 | 618 | R | CB | C | 13 | 30.614 | 1 |
| 984 | 618 | R | CO | C | 13 | 173.638 | 1 |
| 985 | 618 | R | H | H | 1 | 7.893 | 1 |
| 986 | 618 | R | N | N | 15 | 116.707 | 1 |
| 987 | 620 | I | CA | C | 13 | 62.112 | 1 |
| 988 | 620 | I | CB | C | 13 | 35.731 | 1 |
| 989 | 620 | I | CO | C | 13 | 177.018 | 1 |
| 990 | 620 | I | H | H | 1 | 8.465 | 1 |
| 991 | 620 | I | N | N | 15 | 121.915 | 1 |
| 992 | 621 | N | CA | C | 13 | 52.404 | 1 |
| 993 | 621 | N | CB | C | 13 | 38.108 | 1 |
| 994 | 621 | N | H | H | 1 | 7.952 | 1 |
| 995 | 621 | N | N | N | 15 | 126.058 | 1 |
| 996 | 622 | F | CA | C | 13 | 54.399 | 1 |
| 997 | 622 | F | CB | C | 13 | 41.066 | 1 |
| 998 | 622 | F | CO | C | 13 | 173.442 | 1 |
| 999 | 622 | F | H | H | 1 | 6.573 | 1 |
| 1000 | 622 | F | N | N | 15 | 114.01 | 1 |
| 1001 | 623 | T | CA | C | 13 | 59.922 | 1 |
| 1002 | 623 | T | CB | C | 13 | 73.255 | 1 |
| 1003 | 623 | T | H | H | 1 | 11.019 | 1 |
| 1004 | 623 | T | N | N | 15 | 112.666 | 1 |
| 1005 | 624 | Q | CA | C | 13 | 57.991 | 1 |
| 1006 | 624 | Q | CB | C | 13 | 28.115 | 1 |
| 1007 | 624 | Q | CO | C | 13 | 177.817 | 1 |
| 1008 | 624 | Q | H | H | 1 | 9.841 | 1 |
| 1009 | 624 | Q | N | N | 15 | 118.693 | 1 |
| 1010 | 625 | Q | CA | C | 13 | 57.772 | 1 |
| 1011 | 625 | Q | CB | C | 13 | 27.232 | 1 |
| 1012 | 625 | Q | CO | C | 13 | 177.118 | 1 |
| 1013 | 625 | Q | H | H | 1 | 8.35 | 1 |
| 1014 | 625 | Q | N | N | 15 | 118.528 | 1 |
| 1015 | 626 | H | CA | C | 13 | 59.023 | 1 |
| 1016 | 626 | H | CB | C | 13 | 32.018 | 1 |
| 1017 | 626 | H | CO | C | 13 | 175.195 | 1 |
| 1018 | 626 | H | H | H | 1 | 7.69 | 1 |
| 1019 | 626 | H | N | N | 15 | 116.12 | 1 |
| 1020 | 627 | M | CA | C | 13 | 58.703 | 1 |
| 1021 | 627 | M | CB | C | 13 | 29.282 | 1 |
| 1022 | 627 | M | CO | C | 13 | 175.481 | 1 |
| 1023 | 627 | M | H | H | 1 | 7.581 | 1 |
| 1024 | 627 | M | N | N | 15 | 117.619 | 1 |
| 1025 | 629 | Y | CA | C | 13 | 59.898 | 1 |
| 1026 | 629 | Y | CB | C | 13 | 36.935 | 1 |
| 1027 | 629 | Y | CO | C | 13 | 176.303 | 1 |
| 1028 | 629 | Y | H | H | 1 | 7.455 | 1 |
| 1029 | 629 | Y | N | N | 15 | 119.231 | 1 |
| 1030 | 630 | F | CA | C | 13 | 57.548 | 1 |
| 1031 | 630 | F | CO | C | 13 | 179.707 | 1 |
| 1032 | 630 | F | H | H | 1 | 8.72 | 1 |
| 1033 | 630 | F | N | N | 15 | 118.661 | 1 |
| 1034 | 631 | R | CA | C | 13 | 59.879 | 1 |
| 1035 | 631 | R | CB | C | 13 | 29.774 | 1 |
| 1036 | 631 | R | CO | C | 13 | 177.119 | 1 |
| 1037 | 631 | R | H | H | 1 | 8.743 | 1 |
| 1038 | 631 | R | N | N | 15 | 121.276 | 1 |
| 1039 | 632 | K | CB | C | 13 | 32.019 | 1 |
| 1040 | 632 | K | CO | C | 13 | 178.005 | 1 |
| 1041 | 632 | K | H | H | 1 | 7.027 | 1 |
| 1042 | 632 | K | N | N | 15 | 115.472 | 1 |
| 1043 | 633 | R | CA | C | 13 | 59.11 | 1 |
| 1044 | 633 | R | CB | C | 13 | 30.377 | 1 |
| 1045 | 633 | R | H | H | 1 | 8.483 | 1 |
| 1046 | 633 | R | N | N | 15 | 116.56 | 1 |
| 1047 | 634 | M | CA | C | 13 | 57.95 | 1 |
| 1048 | 634 | M | CB | C | 13 | 31.937 | 1 |
| 1049 | 634 | M | H | H | 1 | 8.212 | 1 |
| 1050 | 634 | M | N | N | 15 | 116.933 | 1 |
| 1051 | 635 | V | CA | C | 13 | 66.729 | 1 |
| 1052 | 635 | V | CB | C | 13 | 30.848 | 1 |
| 1053 | 635 | V | CG1 | C | 13 | 22.182 | 1 |
| 1054 | 635 | V | CG2 | C | 13 | 24.307 | 1 |
| 1055 | 635 | V | CO | C | 13 | 176.781 | 1 |
| 1056 | 635 | V | H | H | 1 | 7.401 | 1 |
| 1057 | 635 | V | HG1 | H | 1 | 0.511 | 1 |
| 1058 | 635 | V | HG2 | H | 1 | 1.078 | 1 |
| 1059 | 635 | V | N | N | 15 | 117.807 | 1 |
| 1060 | 636 | W | CA | C | 13 | 63.021 | 1 |
| 1061 | 636 | W | CB | C | 13 | 28.855 | 1 |
| 1062 | 636 | W | CO | C | 13 | 177.991 | 1 |
| 1063 | 636 | W | H | H | 1 | 6.945 | 1 |
| 1064 | 636 | W | HE1 | H | 1 | 10.208 | 1 |
| 1065 | 636 | W | N | N | 15 | 117.761 | 1 |
| 1066 | 636 | W | NE1 | N | 15 | 131.254 | 1 |
| 1067 | 637 | E | CA | C | 13 | 59.634 | 1 |
| 1068 | 637 | E | CB | C | 13 | 29.54 | 1 |
| 1069 | 637 | E | CO | C | 13 | 179.549 | 1 |
| 1070 | 637 | E | H | H | 1 | 8.942 | 1 |
| 1071 | 637 | E | N | N | 15 | 118.312 | 1 |
| 1072 | 638 | I | CA | C | 13 | 65.061 | 1 |
| 1073 | 638 | I | CB | C | 13 | 36.564 | 1 |
| 1074 | 638 | I | CO | C | 13 | 178.793 | 1 |
| 1075 | 638 | I | H | H | 1 | 8.516 | 1 |
| 1076 | 638 | I | N | N | 15 | 118.151 | 1 |
| 1077 | 639 | L | CA | C | 13 | 57.489 | 1 |
| 1078 | 639 | L | CB | C | 13 | 40.751 | 1 |
| 1079 | 639 | L | CD1 | C | 13 | 25.065 | 1 |
| 1080 | 639 | L | CD2 | C | 13 | 22.821 | 1 |
| 1081 | 639 | L | H | H | 1 | 8.021 | 1 |
| 1082 | 639 | L | HD1 | H | 1 | 0.577 | 1 |
| 1083 | 639 | L | HD2 | H | 1 | 0.498 | 1 |
| 1084 | 639 | L | N | N | 15 | 119.857 | 1 |
| 1085 | 640 | H | CA | C | 13 | 55.633 | 1 |
| 1086 | 640 | H | CB | C | 13 | 26.845 | 1 |
| 1087 | 640 | H | H | H | 1 | 7.758 | 1 |
| 1088 | 640 | H | N | N | 15 | 112.218 | 1 |
| 1089 | 641 | R | CA | C | 13 | 56.955 | 1 |
| 1090 | 641 | R | CB | C | 13 | 25.944 | 1 |
| 1091 | 641 | R | CO | C | 13 | 174.773 | 1 |
| 1092 | 641 | R | H | H | 1 | 7.879 | 1 |
| 1093 | 641 | R | N | N | 15 | 122.564 | 1 |
| 1094 | 642 | K | CA | C | 13 | 54.648 | 1 |
| 1095 | 642 | K | CB | C | 13 | 34.915 | 1 |
| 1096 | 642 | K | CO | C | 13 | 172.886 | 1 |
| 1097 | 642 | K | H | H | 1 | 8.22 | 1 |
| 1098 | 642 | K | N | N | 15 | 121.148 | 1 |
| 1099 | 643 | L | CA | C | 13 | 53.678 | 1 |
| 1100 | 643 | L | CB | C | 13 | 41.237 | 1 |
| 1101 | 643 | L | CD1 | C | 13 | 27.306 | 1 |
| 1102 | 643 | L | CD2 | C | 13 | 24.45 | 1 |
| 1103 | 643 | L | CO | C | 13 | 177.594 | 1 |
| 1104 | 643 | L | H | H | 1 | 8.136 | 1 |
| 1105 | 643 | L | HD1 | H | 1 | 0.395 | 1 |
| 1106 | 643 | L | HD2 | H | 1 | 0.572 | 1 |
| 1107 | 643 | L | N | N | 15 | 122.205 | 1 |
| 1108 | 644 | L | CA | C | 13 | 55.222 | 1 |
| 1109 | 644 | L | CB | C | 13 | 41.615 | 1 |
| 1110 | 644 | L | CO | C | 13 | 182.082 | 1 |
| 1111 | 644 | L | H | H | 1 | 8.863 | 1 |
| 1112 | 644 | L | N | N | 15 | 130.114 | 1 |

*referenced using DSS (4,4-dimethyl-4-silapentane-1-sulfonic acid) as the H-1 standard with IUPAC-IUB recommended chemical shift referencing ratios. See, Wishart, et al., "1H, 13C and 15N Chemical Shift Referencing in Biomolecular NMR," J. Biomol. NMR 6: 135-140 (1995); and Markley et al., "Recommendations for the Presentation of NMR Structures of Proteins and Nucleic Acids,". Pure & Appl. Chem. 70: 117-142 (1998).

TABLE 4

SENP1 C603S-SUMO$_{1-92}$ NMR Chemical Shift Values.
Chemical Shift Ambiguity Index Value Definitions
The values other than 1 are used for those atoms with different chemical shifts that cannot be assigned to stereospecific atoms or to specific residues or chains.

| Index Value | Definition |
|---|---|
| 1 | Unique (including isolated methyl protons germinal atoms, and geminal methyl groups with identical chemical shifts (e.g. ILE HD11, HD12, HD13 protons) |
| 2 | Ambiguity of geminal atoms or geminal methyl proton groups (e.g. ASP HB2 and HB3 protons, LEU CD1 and CD2 carbons, or LEU HD11, HD12, HD13 and HD21, HD22, HD23 methyl protons) |
| 3 | Aromatic atoms on opposite sides of symmetrical rings (e.g. TYR HE1 and HE2 protons) |
| 4 | Intraresidue ambiguities (e.g. LYS HG and HD protons or TRP HZ2 and HZ3 protons) |
| 5 | Interresidue ambiguities (LYS 12 vs. LYS 27) |
| 6 | Intermolecular ambiguities (e.g. ASP 31 CA in monomer 1 and ASP 31 CA in monomer 2 of an asymmetrical homodimer, duplex DNA assignments, or other assignments that may apply to atoms in one or more molecule in the molecular assembly) |
| 9 | Ambiguous, specific ambiguity not defined |

| Atom number | Residue number | Amino acid | Atom context | Atom type | Iso-type | Chemical shift (ppm)* | Unique-ness |
|---|---|---|---|---|---|---|---|
| 1 | 419 | E | H | H | 1 | 7.974 | 1 |
| 2 | 419 | E | N | N | 15 | 121.157 | 1 |
| 3 | 420 | F | H | H | 1 | 7.947 | 1 |
| 4 | 420 | F | N | N | 15 | 119.83 | 1 |
| 5 | 422 | E | H | H | 1 | 8.562 | 1 |
| 6 | 422 | E | N | N | 15 | 125.045 | 1 |
| 7 | 423 | I | H | H | 1 | 8.443 | 1 |
| 8 | 423 | I | N | N | 15 | 123.042 | 1 |
| 9 | 424 | T | H | H | 1 | 7.558 | 1 |
| 10 | 424 | T | N | N | 15 | 122.22 | 1 |
| 11 | 425 | E | H | H | 1 | 8.835 | 1 |
| 12 | 425 | E | N | N | 15 | 122.015 | 1 |
| 13 | 426 | E | H | H | 1 | 8.343 | 1 |
| 14 | 426 | E | N | N | 15 | 119.067 | 1 |
| 15 | 427 | M | H | H | 1 | 7.295 | 1 |
| 16 | 427 | M | N | N | 15 | 120.177 | 1 |
| 17 | 428 | E | H | H | 1 | 8.525 | 1 |
| 18 | 428 | E | N | N | 15 | 119.639 | 1 |
| 19 | 429 | K | H | H | 1 | 7.793 | 1 |
| 20 | 429 | K | N | N | 15 | 119.161 | 1 |
| 21 | 430 | E | H | H | 1 | 7.247 | 1 |
| 22 | 430 | E | N | N | 15 | 120.017 | 1 |
| 23 | 432 | K | H | H | 1 | 8.269 | 1 |
| 24 | 432 | K | N | N | 15 | 117.252 | 1 |
| 25 | 433 | D | H | H | 1 | 7.542 | 1 |
| 26 | 433 | D | N | N | 15 | 116.02 | 1 |
| 27 | 434 | V | CG1 | C | 13 | 22.744 | 1 |
| 28 | 434 | V | H | H | 1 | 7.456 | 1 |
| 29 | 434 | V | N | N | 15 | 115.391 | 1 |
| 32 | 434 | V | HG1 | H | 1 | 0.768 | 1 |
| 33 | 435 | F | H | H | 1 | 7.229 | 1 |
| 34 | 435 | F | N | N | 15 | 118.53 | 1 |
| 35 | 436 | R | H | H | 1 | 7.082 | 1 |
| 36 | 436 | R | N | N | 15 | 119.966 | 1 |
| 37 | 437 | D | H | H | 1 | 8.266 | 1 |
| 38 | 437 | D | N | N | 15 | 120.742 | 1 |
| 39 | 438 | G | H | H | 1 | 7.994 | 1 |
| 40 | 438 | G | N | N | 15 | 110.561 | 1 |
| 41 | 439 | D | H | H | 1 | 8.68 | 1 |
| 42 | 439 | D | N | N | 15 | 121.505 | 1 |
| 43 | 440 | Q | H | H | 1 | 8.954 | 1 |
| 44 | 440 | Q | N | N | 15 | 126.9 | 1 |
| 45 | 441 | D | H | H | 1 | 7.858 | 1 |
| 46 | 441 | D | N | N | 15 | 115.853 | 1 |
| 47 | 442 | E | H | H | 1 | 7.08 | 1 |
| 48 | 442 | E | N | N | 15 | 122.689 | 1 |
| 49 | 443 | V | CG1 | C | 13 | 21.595 | 1 |
| 50 | 443 | V | CG2 | C | 13 | 22.122 | 1 |
| 51 | 443 | V | H | H | 1 | 8.563 | 1 |
| 52 | 443 | V | N | N | 15 | 128.078 | 1 |
| 55 | 443 | V | HG1 | H | 1 | 0.731 | 1 |
| 58 | 443 | V | HG2 | H | 1 | 0.896 | 1 |
| 59 | 444 | L | CD1 | C | 13 | 27.192 | 1 |
| 60 | 444 | L | H | H | 1 | 8.928 | 1 |
| 61 | 444 | L | N | N | 15 | 128.342 | 1 |
| 64 | 444 | L | HD1 | H | 1 | 0.609 | 1 |
| 65 | 445 | S | H | H | 1 | 7.327 | 1 |
| 66 | 445 | S | N | N | 15 | 112.548 | 1 |
| 67 | 446 | E | H | H | 1 | 7.889 | 1 |
| 68 | 446 | E | N | N | 15 | 125.959 | 1 |
| 69 | 447 | A | H | H | 1 | 8.267 | 1 |
| 70 | 447 | A | N | N | 15 | 125.511 | 1 |
| 71 | 448 | F | H | H | 1 | 8.549 | 1 |
| 72 | 448 | F | N | N | 15 | 117.045 | 1 |
| 73 | 449 | R | H | H | 1 | 8.43 | 1 |
| 74 | 449 | R | N | N | 15 | 112.963 | 1 |
| 75 | 450 | L | CD1 | C | 13 | 26.152 | 1 |
| 76 | 450 | L | CD2 | C | 13 | 23.171 | 1 |
| 77 | 450 | L | H | H | 1 | 8.288 | 1 |
| 78 | 450 | L | N | N | 15 | 121.64 | 1 |
| 81 | 450 | L | HD1 | H | 1 | 0.918 | 1 |
| 84 | 450 | L | HD2 | H | 1 | 1.032 | 1 |
| 85 | 451 | T | H | H | 1 | 8.297 | 1 |
| 86 | 451 | T | N | N | 15 | 113.505 | 1 |
| 87 | 452 | I | H | H | 1 | 8.385 | 1 |
| 88 | 452 | I | N | N | 15 | 124.62 | 1 |
| 89 | 453 | T | H | H | 1 | 9.666 | 1 |
| 90 | 453 | T | N | N | 15 | 120.795 | 1 |
| 91 | 454 | R | H | H | 1 | 8.168 | 1 |
| 92 | 454 | R | N | N | 15 | 123.055 | 1 |
| 93 | 455 | K | H | H | 1 | 8.41 | 1 |
| 94 | 455 | K | N | N | 15 | 120.473 | 1 |
| 95 | 456 | D | H | H | 1 | 7.227 | 1 |
| 96 | 456 | D | N | N | 15 | 118.114 | 1 |
| 97 | 457 | I | H | H | 1 | 8.102 | 1 |
| 98 | 457 | I | N | N | 15 | 122.652 | 1 |
| 99 | 458 | Q | H | H | 1 | 7.821 | 1 |
| 100 | 458 | Q | N | N | 15 | 119.174 | 1 |
| 101 | 459 | T | H | H | 1 | 7.826 | 1 |
| 102 | 459 | T | N | N | 15 | 114.259 | 1 |
| 103 | 460 | L | CD1 | C | 13 | 26.138 | 1 |
| 104 | 460 | L | CD2 | C | 13 | 26.003 | 1 |
| 105 | 460 | L | H | H | 1 | 7.18 | 1 |
| 106 | 460 | L | N | N | 15 | 116.293 | 1 |
| 109 | 460 | L | HD1 | H | 1 | 0.845 | 1 |
| 112 | 460 | L | HD2 | H | 1 | 0.954 | 1 |
| 113 | 461 | D | H | H | 1 | 7.356 | 1 |
| 114 | 461 | D | N | N | 15 | 121.211 | 1 |
| 115 | 462 | H | H | H | 1 | 7.659 | 1 |
| 116 | 462 | H | N | N | 15 | 120.742 | 1 |
| 117 | 465 | W | H | H | 1 | 8.258 | 1 |
| 118 | 465 | W | N | N | 15 | 121.504 | 1 |
| 119 | 465 | W | HE1 | H | 1 | 9.997 | 1 |
| 120 | 465 | W | NE1 | H | 1 | 130.62 | 1 |
| 121 | 466 | L | CD1 | C | 13 | 25.625 | 1 |
| 122 | 466 | L | CD2 | C | 13 | 23.625 | 1 |
| 123 | 466 | L | H | H | 1 | 7.529 | 1 |
| 124 | 466 | L | N | N | 15 | 126.826 | 1 |
| 127 | 466 | L | HD1 | H | 1 | 0.684 | 1 |
| 130 | 466 | L | HD2 | H | 1 | 0.704 | 1 |
| 131 | 467 | D | H | H | 1 | 6.937 | 1 |
| 132 | 467 | D | N | N | 15 | 117.87 | 1 |
| 133 | 468 | D | H | H | 1 | 8.19 | 1 |
| 134 | 468 | D | N | N | 15 | 115.279 | 1 |
| 135 | 470 | I | H | H | 1 | 7.581 | 1 |
| 136 | 470 | I | N | N | 15 | 118.739 | 1 |
| 137 | 471 | I | H | H | 1 | 6.823 | 1 |
| 138 | 471 | I | N | N | 15 | 118.333 | 1 |
| 139 | 472 | D | H | H | 1 | 8.781 | 1 |
| 140 | 472 | D | N | N | 15 | 116.126 | 1 |
| 141 | 473 | F | H | H | 1 | 8.248 | 1 |
| 142 | 473 | F | N | N | 15 | 124.484 | 1 |
| 143 | 475 | M | H | H | 1 | 8.642 | 1 |

TABLE 4-continued

SENP1 C603S-SUMO$_{1-92}$ NMR Chemical Shift Values.
Chemical Shift Ambiguity Index Value Definitions
The values other than 1 are used for those atoms with
different chemical shifts that cannot be assigned to
stereospecific atoms or to specific residues or chains.

| | | | | | | |
|---|---|---|---|---|---|---|
| 144 | 475 | M | N | N | 15 | 116.267 | 1 |
| 145 | 476 | D | H | H | 1 | 7.328 | 1 |
| 146 | 476 | D | N | N | 15 | 118.167 | 1 |
| 147 | 477 | M | H | H | 1 | 7.588 | 1 |
| 148 | 477 | M | N | N | 15 | 122.218 | 1 |
| 149 | 478 | L | CD1 | C | 13 | 27.574 | 1 |
| 150 | 478 | L | CD2 | C | 13 | 22.365 | 1 |
| 151 | 478 | L | H | H | 1 | 7.689 | 1 |
| 152 | 478 | L | N | N | 15 | 121.041 | 1 |
| 155 | 478 | L | HD1 | H | 1 | 0.707 | 1 |
| 158 | 478 | L | HD2 | H | 1 | 0.458 | 1 |
| 159 | 479 | M | H | H | 1 | 7.581 | 1 |
| 160 | 479 | M | N | N | 15 | 120.182 | 1 |
| 161 | 480 | E | H | H | 1 | 8.04 | 1 |
| 162 | 480 | E | N | N | 15 | 123.808 | 1 |
| 163 | 481 | R | H | H | 1 | 7.872 | 1 |
| 164 | 481 | R | N | N | 15 | 121.587 | 1 |
| 165 | 482 | S | H | H | 1 | 7.133 | 1 |
| 166 | 482 | S | N | N | 15 | 114.199 | 1 |
| 167 | 483 | K | H | H | 1 | 6.896 | 1 |
| 168 | 483 | K | N | N | 15 | 119.755 | 1 |
| 169 | 484 | E | H | H | 1 | 8.035 | 1 |
| 170 | 484 | E | N | N | 15 | 122.017 | 1 |
| 171 | 485 | K | H | H | 1 | 8.183 | 1 |
| 172 | 485 | K | N | N | 15 | 122.621 | 1 |
| 173 | 486 | G | H | H | 1 | 8.674 | 1 |
| 174 | 486 | G | N | N | 15 | 112.424 | 1 |
| 175 | 487 | L | CD1 | C | 13 | 25.976 | 1 |
| 176 | 487 | L | CD2 | C | 13 | 23.426 | 1 |
| 177 | 487 | L | H | H | 1 | 7.277 | 1 |
| 178 | 487 | L | N | N | 15 | 122.648 | 1 |
| 181 | 487 | L | HD1 | H | 1 | 0.802 | 1 |
| 184 | 487 | L | HD2 | H | 1 | 0.853 | 1 |
| 185 | 489 | S | H | H | 1 | 9.049 | 1 |
| 186 | 489 | S | N | N | 15 | 119.012 | 1 |
| 187 | 490 | V | CG1 | C | 13 | 21.236 | 1 |
| 188 | 490 | V | CG2 | C | 13 | 23.244 | 1 |
| 189 | 490 | V | H | H | 1 | 7.325 | 1 |
| 190 | 490 | V | N | N | 15 | 119.713 | 1 |
| 191 | 490 | V | HG1 | H | 1 | 0.583 | 1 |
| 196 | 490 | V | HG2 | H | 1 | 0.912 | 1 |
| 197 | 491 | H | H | H | 1 | 8.716 | 1 |
| 198 | 491 | H | N | N | 15 | 125.135 | 1 |
| 199 | 492 | A | H | H | 1 | 7.396 | 1 |
| 200 | 492 | A | N | N | 15 | 130.645 | 1 |
| 201 | 494 | D | H | H | 1 | 8.676 | 1 |
| 202 | 494 | D | N | N | 15 | 117.371 | 1 |
| 203 | 495 | T | H | H | 1 | 8.641 | 1 |
| 204 | 495 | T | N | N | 15 | 112.625 | 1 |
| 205 | 497 | F | H | H | 1 | 7.868 | 1 |
| 206 | 497 | F | N | N | 15 | 122.062 | 1 |
| 207 | 498 | F | H | H | 1 | 9.932 | 1 |
| 208 | 498 | F | N | N | 15 | 121.373 | 1 |
| 209 | 499 | T | H | H | 1 | 6.901 | 1 |
| 210 | 499 | T | N | N | 15 | 113.079 | 1 |
| 211 | 500 | K | H | H | 1 | 7.689 | 1 |
| 212 | 500 | K | N | N | 15 | 123.985 | 1 |
| 213 | 501 | L | CD1 | C | 13 | 21.431 | 1 |
| 214 | 501 | L | CD2 | C | 13 | 26.226 | 1 |
| 217 | 501 | L | HD1 | H | 1 | 0.589 | 1 |
| 220 | 501 | L | HD2 | H | 1 | 0.244 | 1 |
| 221 | 502 | K | H | H | 1 | 8.034 | 1 |
| 222 | 502 | K | N | N | 15 | 118.063 | 1 |
| 223 | 503 | T | H | H | 1 | 7.409 | 1 |
| 224 | 503 | T | N | N | 15 | 109.905 | 1 |
| 225 | 504 | A | H | H | 1 | 8.332 | 1 |
| 226 | 504 | A | N | N | 15 | 125.057 | 1 |
| 227 | 505 | G | H | H | 1 | 7.268 | 1 |
| 228 | 505 | G | N | N | 15 | 109.015 | 1 |
| 229 | 506 | Y | H | H | 1 | 8.399 | 1 |
| 230 | 506 | Y | N | N | 15 | 118.799 | 1 |
| 231 | 507 | Q | H | H | 1 | 8.555 | 1 |
| 232 | 507 | Q | N | N | 15 | 114.738 | 1 |
| 233 | 508 | A | H | H | 1 | 7.049 | 1 |
| 234 | 508 | A | N | N | 15 | 118.763 | 1 |
| 235 | 509 | V | CG1 | C | 13 | 19.211 | 1 |
| 236 | 509 | V | CG2 | C | 13 | 20.045 | 1 |
| 237 | 509 | V | H | H | 1 | 6.759 | 1 |
| 238 | 509 | V | N | N | 15 | 105.237 | 1 |
| 241 | 509 | V | HG1 | H | 1 | 0.198 | 1 |
| 244 | 509 | V | HG2 | H | 1 | 0.47 | 1 |
| 245 | 510 | K | H | H | 1 | 7.119 | 1 |
| 246 | 510 | K | N | N | 15 | 128.018 | 1 |
| 247 | 511 | R | H | H | 1 | 8.684 | 1 |
| 248 | 511 | R | N | N | 15 | 117.231 | 1 |
| 249 | 512 | W | H | H | 1 | 8.542 | 1 |
| 250 | 512 | W | N | N | 15 | 120.625 | 1 |
| 251 | 512 | W | HE1 | H | 1 | 9.942 | 1 |
| 252 | 512 | W | NE1 | H | 1 | 130.341 | 1 |
| 253 | 513 | T | H | H | 1 | 7.069 | 1 |
| 254 | 513 | T | N | N | 15 | 106.003 | 1 |
| 255 | 514 | K | H | H | 1 | 7.238 | 1 |
| 256 | 514 | K | N | N | 15 | 121.358 | 1 |
| 257 | 515 | K | H | H | 1 | 8.487 | 1 |
| 258 | 515 | K | N | N | 15 | 116.476 | 1 |
| 259 | 516 | V | CG1 | C | 13 | 22.32 | 1 |
| 260 | 516 | V | CG2 | C | 13 | 19.555 | 1 |
| 261 | 516 | V | H | H | 1 | 7.299 | 1 |
| 262 | 516 | V | N | N | 15 | 119.473 | 1 |
| 265 | 516 | V | HG1 | H | 1 | 1.018 | 1 |
| 268 | 516 | V | HG2 | H | 1 | 0.836 | 1 |
| 269 | 517 | D | H | H | 1 | 8.389 | 1 |
| 270 | 517 | D | N | N | 15 | 124.991 | 1 |
| 271 | 518 | V | CG1 | C | 13 | 21.972 | 1 |
| 272 | 518 | V | CG2 | C | 13 | 17.937 | 1 |
| 273 | 518 | V | H | H | 1 | 8.864 | 1 |
| 274 | 518 | V | N | N | 15 | 122.483 | 1 |
| 277 | 518 | V | HG1 | H | 1 | 0.73 | 1 |
| 280 | 518 | V | HG2 | H | 1 | 0.268 | 1 |
| 281 | 519 | F | H | H | 1 | 7.156 | 1 |
| 282 | 519 | F | N | N | 15 | 111.705 | 1 |
| 283 | 520 | S | H | H | 1 | 7.418 | 1 |
| 284 | 520 | S | N | N | 15 | 114.604 | 1 |
| 285 | 521 | V | CG1 | C | 13 | 21.606 | 1 |
| 286 | 521 | V | CG2 | C | 13 | 19.292 | 1 |
| 287 | 521 | V | H | H | 1 | 6.57 | 1 |
| 288 | 521 | V | N | N | 15 | 114.783 | 1 |
| 291 | 521 | V | HG1 | H | 1 | 0.698 | 1 |
| 294 | 521 | V | HG2 | H | 1 | 0.757 | 1 |
| 295 | 522 | D | H | H | 1 | 8.102 | 1 |
| 296 | 522 | D | N | N | 15 | 121.096 | 1 |
| 297 | 523 | I | H | H | 1 | 8.117 | 1 |
| 298 | 523 | I | N | N | 15 | 118.339 | 1 |
| 299 | 524 | L | CD1 | C | 13 | 24.558 | 2 |
| 300 | 524 | L | CD2 | C | 13 | 24.558 | 2 |
| 301 | 524 | L | H | H | 1 | 9.253 | 1 |
| 302 | 524 | L | N | N | 15 | 122.892 | 1 |
| 305 | 524 | L | HG1 | H | 1 | 0.841 | 2 |
| 308 | 524 | L | HG2 | H | 1 | 0.841 | 2 |
| 309 | 525 | L | CD1 | C | 13 | 27.708 | 2 |
| 310 | 525 | L | CD2 | C | 13 | 23.849 | 1 |
| 311 | 525 | L | H | H | 1 | 8.636 | 1 |
| 312 | 525 | L | N | N | 15 | 121.574 | 1 |
| 315 | 525 | L | HD1 | H | 1 | 0.775 | 1 |
| 318 | 525 | L | HD2 | H | 1 | 0.735 | 1 |
| 319 | 526 | V | CG1 | C | 13 | 20.514 | 1 |
| 320 | 526 | V | CG2 | C | 13 | 19.367 | 1 |
| 323 | 526 | V | HG1 | H | 1 | −0.557 | 1 |
| 326 | 526 | V | HG2 | H | 1 | 0.332 | 1 |
| 327 | 528 | I | H | H | 1 | 8.599 | 1 |
| 328 | 528 | I | N | N | 15 | 125.838 | 1 |
| 329 | 529 | H | H | H | 1 | 9.049 | 1 |
| 330 | 529 | H | N | N | 15 | 130.138 | 1 |
| 331 | 530 | L | CD1 | C | 13 | 25.956 | 1 |
| 332 | 530 | L | CD2 | C | 13 | 23.945 | 1 |
| 333 | 530 | L | H | H | 1 | 8.536 | 1 |
| 334 | 530 | L | N | N | 15 | 131.927 | 1 |
| 337 | 530 | L | HD1 | H | 1 | 0.891 | 1 |

TABLE 4-continued

SENP1 C603S-SUMO$_{1-92}$ NMR Chemical Shift Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 340 | 530 | L | HD2 | H | 1 | 0.759 | 1 |
| 341 | 531 | G | H | H | 1 | 8 | 1 |
| 342 | 531 | G | N | N | 15 | 116.007 | 1 |
| 343 | 532 | V | CG1 | C | 13 | 20.988 | 1 |
| 344 | 532 | V | CG2 | C | 13 | 17.895 | 1 |
| 347 | 532 | V | HG1 | H | 1 | 0.507 | 1 |
| 350 | 532 | V | HG2 | H | 1 | 0.396 | 1 |
| 351 | 533 | H | H | H | 1 | 7.652 | 1 |
| 352 | 533 | H | N | N | 15 | 123.973 | 1 |
| 353 | 534 | W | H | H | 1 | 7.787 | 1 |
| 354 | 534 | W | N | N | 15 | 125.281 | 1 |
| 355 | 534 | W | HE1 | H | 1 | 9.36 | 1 |
| 356 | 534 | W | NE1 | H | 1 | 128.566 | 1 |
| 357 | 535 | C | H | H | 1 | 9.374 | 1 |
| 358 | 535 | C | N | N | 15 | 118.493 | 1 |
| 359 | 536 | L | CD1 | C | 13 | 22.488 | 1 |
| 360 | 536 | L | CD2 | C | 13 | 26.383 | 1 |
| 363 | 536 | L | HD1 | H | 1 | 0.708 | 1 |
| 366 | 536 | L | HD2 | H | 1 | 0.622 | 1 |
| 367 | 537 | A | H | H | 1 | 8.735 | 1 |
| 368 | 537 | A | N | N | 15 | 127.969 | 1 |
| 369 | 538 | V | CG1 | C | 13 | 21.782 | 1 |
| 370 | 538 | V | CG2 | C | 13 | 22.071 | 1 |
| 371 | 538 | V | H | H | 1 | 8.971 | 1 |
| 372 | 538 | V | N | N | 15 | 120.496 | 1 |
| 375 | 538 | V | HG1 | H | 1 | 0.885 | 1 |
| 378 | 538 | V | HG2 | H | 1 | 0.831 | 1 |
| 379 | 539 | V | CG1 | C | 13 | 20.583 | 1 |
| 380 | 539 | V | CG2 | C | 13 | 19.613 | 1 |
| 381 | 539 | V | H | H | 1 | 9.299 | 1 |
| 382 | 539 | V | N | N | 15 | 131.537 | 1 |
| 385 | 539 | V | HG1 | H | 1 | 0.452 | 1 |
| 388 | 539 | V | HG2 | H | 1 | 0.894 | 1 |
| 389 | 540 | D | H | H | 1 | 8.849 | 1 |
| 390 | 540 | D | N | N | 15 | 127.571 | 1 |
| 391 | 541 | F | H | H | 1 | 9.394 | 1 |
| 392 | 541 | F | N | N | 15 | 125.014 | 1 |
| 393 | 542 | R | H | H | 1 | 8.636 | 1 |
| 394 | 542 | R | N | N | 15 | 118.378 | 1 |
| 395 | 543 | K | H | H | 1 | 6.667 | 1 |
| 396 | 543 | K | N | N | 15 | 115.058 | 1 |
| 397 | 544 | K | H | H | 1 | 7.337 | 1 |
| 398 | 544 | K | N | N | 15 | 116.66 | 1 |
| 399 | 545 | D | H | H | 1 | 7.143 | 1 |
| 400 | 545 | D | N | N | 15 | 114.477 | 1 |
| 401 | 546 | I | H | H | 1 | 8.348 | 1 |
| 402 | 546 | I | N | N | 15 | 121.213 | 1 |
| 403 | 547 | T | H | H | 1 | 8.68 | 1 |
| 404 | 547 | T | N | N | 15 | 122.503 | 1 |
| 405 | 548 | Y | H | H | 1 | 8.599 | 1 |
| 406 | 548 | Y | N | N | 15 | 129.81 | 1 |
| 407 | 549 | Y | H | H | 1 | 8.988 | 1 |
| 408 | 549 | Y | N | N | 15 | 126.841 | 1 |
| 409 | 550 | D | H | H | 1 | 7.986 | 1 |
| 410 | 550 | D | N | N | 15 | 124.111 | 1 |
| 411 | 551 | S | H | H | 1 | 9.257 | 1 |
| 412 | 551 | S | N | N | 15 | 123.506 | 1 |
| 413 | 552 | M | H | H | 1 | 9.118 | 1 |
| 414 | 552 | M | N | N | 15 | 122.883 | 1 |
| 415 | 553 | G | H | H | 1 | 7.765 | 1 |
| 416 | 553 | G | N | N | 15 | 110.571 | 1 |
| 417 | 554 | G | H | H | 1 | 7.593 | 1 |
| 418 | 554 | G | N | N | 15 | 108.922 | 1 |
| 419 | 555 | I | H | H | 1 | 7.986 | 1 |
| 420 | 555 | I | N | N | 15 | 119.104 | 1 |
| 421 | 556 | D | H | H | 1 | 7.676 | 1 |
| 422 | 556 | D | N | N | 15 | 125.208 | 1 |
| 423 | 557 | D | H | H | 1 | 8.221 | 1 |
| 424 | 557 | D | N | N | 15 | 122.087 | 1 |
| 425 | 558 | E | H | H | 1 | 8.444 | 1 |
| 426 | 558 | E | N | N | 15 | 121.771 | 1 |
| 427 | 559 | A | H | H | 1 | 7.431 | 1 |
| 428 | 559 | A | N | N | 15 | 121.623 | 1 |
| 429 | 560 | C | H | H | 1 | 6.749 | 1 |
| 430 | 560 | C | N | N | 15 | 112.908 | 1 |
| 431 | 561 | R | H | H | 1 | 7.935 | 1 |
| 432 | 561 | R | N | N | 15 | 121.153 | 1 |
| 433 | 562 | I | H | H | 1 | 8.494 | 1 |
| 434 | 562 | I | N | N | 15 | 121.654 | 1 |
| 435 | 563 | L | CD1 | C | 13 | 26.251 | 1 |
| 436 | 563 | L | H | H | 1 | 7.51 | 1 |
| 437 | 563 | L | N | N | 15 | 121.675 | 1 |
| 440 | 563 | L | HD1 | H | 1 | 0.705 | 1 |
| 441 | 564 | L | CD1 | C | 13 | 23.21 | 1 |
| 442 | 564 | L | CD2 | C | 13 | 25.851 | 1 |
| 443 | 564 | L | H | H | 1 | 7.927 | 1 |
| 444 | 564 | L | N | N | 15 | 123.395 | 1 |
| 447 | 564 | L | HD1 | H | 1 | 0.527 | 1 |
| 450 | 564 | L | HD2 | H | 1 | 0.857 | 1 |
| 451 | 565 | Q | H | H | 1 | 7.814 | 1 |
| 452 | 565 | Q | N | N | 15 | 117.094 | 1 |
| 453 | 566 | Y | H | H | 1 | 8.072 | 1 |
| 454 | 566 | Y | N | N | 15 | 122.424 | 1 |
| 455 | 567 | L | CD1 | C | 13 | 26.248 | 1 |
| 456 | 567 | L | H | H | 1 | 7.659 | 1 |
| 457 | 567 | L | N | N | 15 | 119.901 | 1 |
| 460 | 567 | L | HD1 | H | 1 | 0.295 | 1 |
| 461 | 568 | K | H | H | 1 | 7.303 | 1 |
| 462 | 568 | K | N | N | 15 | 117.193 | 1 |
| 463 | 569 | Q | H | H | 1 | 7.605 | 1 |
| 464 | 569 | Q | N | N | 15 | 120.146 | 1 |
| 465 | 570 | E | H | H | 1 | 8.815 | 1 |
| 466 | 570 | E | N | N | 15 | 125.031 | 1 |
| 467 | 571 | S | H | H | 1 | 7.999 | 1 |
| 468 | 571 | S | N | N | 15 | 113.963 | 1 |
| 469 | 572 | I | H | H | 1 | 6.963 | 1 |
| 470 | 572 | I | N | N | 15 | 120.839 | 1 |
| 471 | 573 | D | H | H | 1 | 8.221 | 1 |
| 472 | 573 | D | N | N | 15 | 120.607 | 1 |
| 473 | 574 | K | H | H | 1 | 8.471 | 1 |
| 474 | 574 | K | N | N | 15 | 110.577 | 1 |
| 475 | 575 | K | H | H | 1 | 7.695 | 1 |
| 476 | 575 | K | N | N | 15 | 115.597 | 1 |
| 477 | 580 | D | H | H | 1 | 7.94 | 1 |
| 478 | 580 | D | N | N | 15 | 129.176 | 1 |
| 479 | 581 | T | H | H | 1 | 7.92 | 1 |
| 480 | 581 | T | N | N | 15 | 115.295 | 1 |
| 481 | 582 | D | H | H | 1 | 8.477 | 1 |
| 482 | 582 | D | N | N | 15 | 125.759 | 1 |
| 483 | 584 | W | HE1 | H | 1 | 10.14 | 1 |
| 484 | 584 | W | NE1 | H | 1 | 131.131 | 1 |
| 485 | 585 | Q | H | H | 1 | 8.228 | 1 |
| 486 | 585 | Q | N | N | 15 | 121.5 | 1 |
| 487 | 586 | L | CD1 | C | 13 | 24.774 | 1 |
| 488 | 586 | L | H | H | 1 | 8.179 | 1 |
| 489 | 586 | L | N | N | 15 | 123.493 | 1 |
| 492 | 586 | L | HD1 | H | 1 | 0.902 | 1 |
| 493 | 587 | F | H | H | 1 | 8.927 | 1 |
| 494 | 587 | F | N | N | 15 | 120.564 | 1 |
| 495 | 588 | S | H | H | 1 | 8.491 | 1 |
| 496 | 588 | S | N | N | 15 | 116.853 | 1 |
| 497 | 589 | K | H | H | 1 | 8.272 | 1 |
| 498 | 589 | K | N | N | 15 | 125.148 | 1 |
| 499 | 590 | K | H | H | 1 | 9.035 | 1 |
| 500 | 590 | K | N | N | 15 | 125.714 | 1 |
| 501 | 591 | S | H | H | 1 | 8.628 | 1 |
| 502 | 591 | S | N | N | 15 | 117.949 | 1 |
| 503 | 592 | Q | H | H | 1 | 7.72 | 1 |
| 504 | 592 | Q | N | N | 15 | 115.49 | 1 |
| 505 | 593 | E | H | H | 1 | 8.054 | 1 |
| 506 | 593 | E | N | N | 15 | 117.488 | 1 |
| 507 | 594 | I | H | H | 1 | 7.053 | 1 |
| 508 | 594 | I | N | N | 15 | 112.806 | 1 |
| 509 | 596 | Q | H | H | 1 | 8.456 | 1 |
| 510 | 596 | Q | N | N | 15 | 120.73 | 1 |
| 511 | 597 | Q | H | H | 1 | 8.576 | 1 |
| 512 | 597 | Q | N | N | 15 | 119.759 | 1 |
| 513 | 598 | M | H | H | 1 | 9.401 | 1 |

TABLE 4-continued

SENP1 C603S-SUMO$_{1-92}$ NMR Chemical Shift Values.
Chemical Shift Ambiguity Index Value Definitions
The values other than 1 are used for those atoms with
different chemical shifts that cannot be assigned to
stereospecific atoms or to specific residues or chains.

| | | | | | | | |
|---|---|---|---|---|---|---|---|
| 514 | 598 | M | N | N | 15 | 120.151 | 1 |
| 515 | 599 | D | H | H | 1 | 7.357 | 1 |
| 516 | 599 | D | N | N | 15 | 116.972 | 1 |
| 517 | 602 | D | H | H | 1 | 7.383 | 1 |
| 518 | 602 | D | N | N | 15 | 119.804 | 1 |
| 519 | 603 | S | H | H | 1 | 8.061 | 1 |
| 520 | 603 | S | N | N | 15 | 121.228 | 1 |
| 521 | 604 | G | H | H | 1 | 8.814 | 1 |
| 522 | 604 | G | N | N | 15 | 109.019 | 1 |
| 523 | 605 | M | H | H | 1 | 6.87 | 1 |
| 524 | 605 | M | N | N | 15 | 119.181 | 1 |
| 525 | 606 | F | H | H | 1 | 8.087 | 1 |
| 526 | 606 | F | N | N | 15 | 120.065 | 1 |
| 527 | 607 | A | H | H | 1 | 7.948 | 1 |
| 528 | 607 | A | N | N | 15 | 119.608 | 1 |
| 529 | 608 | C | H | H | 1 | 7.095 | 1 |
| 530 | 608 | C | N | N | 15 | 112.346 | 1 |
| 531 | 609 | K | H | H | 1 | 7.948 | 1 |
| 532 | 609 | K | N | N | 15 | 118.448 | 1 |
| 533 | 610 | Y | H | H | 1 | 9.542 | 1 |
| 534 | 610 | Y | N | N | 15 | 122.405 | 1 |
| 535 | 611 | A | H | H | 1 | 7.333 | 1 |
| 536 | 611 | A | N | N | 15 | 119.249 | 1 |
| 537 | 612 | D | H | H | 1 | 8.263 | 1 |
| 538 | 612 | D | N | N | 15 | 120.131 | 1 |
| 539 | 613 | C | H | H | 1 | 7.203 | 1 |
| 540 | 613 | C | N | N | 15 | 115.162 | 1 |
| 541 | 614 | I | H | H | 1 | 8.484 | 1 |
| 542 | 614 | I | N | N | 15 | 120.137 | 1 |
| 543 | 615 | T | H | H | 1 | 8.165 | 1 |
| 544 | 615 | T | N | N | 15 | 109.158 | 1 |
| 545 | 616 | K | H | H | 1 | 7.126 | 1 |
| 546 | 616 | K | N | N | 15 | 119.661 | 1 |
| 547 | 617 | D | H | H | 1 | 7.896 | 1 |
| 548 | 617 | D | N | N | 15 | 118.551 | 1 |
| 549 | 618 | R | H | H | 1 | 7.855 | 1 |
| 550 | 618 | R | N | N | 15 | 117.684 | 1 |
| 551 | 620 | I | H | H | 1 | 8.365 | 1 |
| 552 | 620 | I | N | N | 15 | 122.909 | 1 |
| 553 | 621 | D | H | H | 1 | 7.872 | 1 |
| 554 | 621 | D | N | N | 15 | 127.17 | 1 |
| 555 | 622 | F | H | H | 1 | 6.479 | 1 |
| 556 | 622 | F | N | N | 15 | 114.836 | 1 |
| 557 | 623 | T | H | H | 1 | 10.893 | 1 |
| 558 | 623 | T | N | N | 15 | 113.615 | 1 |
| 559 | 624 | Q | H | H | 1 | 9.761 | 1 |
| 560 | 624 | Q | N | N | 15 | 119.808 | 1 |
| 561 | 625 | Q | H | H | 1 | 8.292 | 1 |
| 562 | 625 | Q | N | N | 15 | 119.007 | 1 |
| 563 | 626 | H | H | H | 1 | 7.627 | 1 |
| 564 | 626 | H | N | N | 15 | 117.04 | 1 |
| 565 | 627 | M | H | H | 1 | 7.554 | 1 |
| 566 | 627 | M | N | N | 15 | 118.727 | 1 |
| 567 | 629 | Y | H | H | 1 | 7.389 | 1 |
| 568 | 629 | Y | N | N | 15 | 120.089 | 1 |
| 569 | 630 | F | H | H | 1 | 8.629 | 1 |
| 570 | 630 | F | N | N | 15 | 119.732 | 1 |
| 571 | 631 | R | H | H | 1 | 8.753 | 1 |
| 572 | 631 | R | N | N | 15 | 122.645 | 1 |
| 573 | 632 | K | H | H | 1 | 6.955 | 1 |
| 574 | 632 | K | N | N | 15 | 116.472 | 1 |
| 575 | 633 | R | H | H | 1 | 8.412 | 1 |
| 576 | 633 | R | N | N | 15 | 117.619 | 1 |
| 577 | 634 | M | H | H | 1 | 8.154 | 1 |
| 578 | 634 | M | N | N | 15 | 117.932 | 1 |
| 579 | 635 | V | CG1 | C | 13 | 22.402 | 1 |
| 580 | 635 | V | CG2 | C | 13 | 24.472 | 1 |
| 581 | 635 | V | H | H | 1 | 7.322 | 1 |
| 582 | 635 | V | N | N | 15 | 118.68 | 1 |
| 585 | 635 | V | HG1 | H | 1 | 0.533 | 1 |
| 588 | 635 | V | HG2 | H | 1 | 1.092 | 1 |
| 589 | 636 | W | H | H | 1 | 6.859 | 1 |
| 590 | 636 | W | N | N | 15 | 118.812 | 1 |
| 591 | 636 | W | HE1 | H | 1 | 10.124 | 1 |
| 592 | 636 | W | NE1 | H | 1 | 132.344 | 1 |
| 593 | 637 | E | H | H | 1 | 8.839 | 1 |
| 594 | 637 | E | N | N | 15 | 119.355 | 1 |
| 595 | 638 | I | H | H | 1 | 8.41 | 1 |
| 596 | 638 | I | N | N | 15 | 119.139 | 1 |
| 597 | 639 | L | CD1 | C | 13 | 25.313 | 1 |
| 598 | 639 | L | CD2 | C | 13 | 22.916 | 1 |
| 599 | 639 | L | H | H | 1 | 7.977 | 1 |
| 600 | 639 | L | N | N | 15 | 120.642 | 1 |
| 603 | 639 | L | HD1 | H | 1 | 0.596 | 1 |
| 606 | 639 | L | HD2 | H | 1 | 0.514 | 1 |
| 607 | 640 | H | H | H | 1 | 7.669 | 1 |
| 608 | 640 | H | N | N | 15 | 113.238 | 1 |
| 609 | 641 | R | H | H | 1 | 7.794 | 1 |
| 610 | 641 | R | N | N | 15 | 123.547 | 1 |
| 611 | 642 | K | H | H | 1 | 8.152 | 1 |
| 612 | 642 | K | N | N | 15 | 122.071 | 1 |
| 613 | 643 | L | CD1 | C | 13 | 27.478 | 1 |
| 614 | 643 | L | CD2 | C | 13 | 24.632 | 1 |
| 615 | 643 | L | H | H | 1 | 8.058 | 1 |
| 616 | 643 | L | N | N | 15 | 123.331 | 1 |
| 619 | 643 | L | HD1 | H | 1 | 0.412 | 1 |
| 622 | 643 | L | HD2 | H | 1 | 0.573 | 1 |
| 623 | 644 | L | H | H | 1 | 8.748 | 1 |
| 624 | 644 | L | N | N | 15 | 131.146 | 1 |

*referenced using DSS (4,4-dimethyl-4-silapentane-1-sulfonic acid) as the H-1 standard with IUPAC-IUB recommended chemical shift referencing ratios. See, Wishart, et al., "1H, 13C and 15N Chemical Shift Referencing in Biomolecular NMR," J. Biomol. NMR 6: 135-140 (1995); and Markley et al., "Recommendations for the Presentation of NMR Structures of Proteins and Nucleic Acids,". Pure & Appl. Chem. 70: 117-142 (1998).

```
                    Sequence Listing

SEQ ID NO: 1 Isoform 1 SENP1
MDDIADRMRM  DAGEVTLVNH  NSVFKTHLLP  QTGFPEDQLS
LSDQQILSSR  QGHLDRSFTC  STRSAAYNPS  YYSDNPSSDS  FLGSGDLRTF
GQSANGQWRN  STPSSSSSLQ  KSRNSRSLYL  ETRKTSSGLS  NSFAGKSNHH
CHVSAYEKSF  PIKPVPSPSW  SGSCRRSLLS  PKKTQRRHVS  TAEETVQEEE
REIYRQLLQM  VTGKQFTIAK  PTTHFPLHLS  RCLSSSKNTL  KDSLFKNGNS
CASQIIGSDT  SSSGSASILT  NQEQLSHSVY  SLSSYTPDVA  FGSKDSGTLH
HPHHHSVPH   QPDNLAASNT  QSEGSDSVIL  LKVKDSQTPT  PSSTFFQAEL
WIKELTSVYD  SRARERLRQI  EEQKALALQL  QNQRLQEREH  SVHDSVELHL
RVPLEKEIPV  TVVQETQKKG  HKLTDSEDEF  PEITEEMEKE  IKNVFRNGNQ
DEVLSEAFRL  TITRKDIQTL  NHLNWLNDEI  INFYMNMLME  RSKEKGLPSV
HAFNTFFFTK  LKTAGYQAVK  RWTKKVDVFS  VDILLVPIHL  GVHWCLAVVD
FRKKNITYYD  SMGGINNEAC  RILLQYLKQE  SIDKKRKEFD  TNGWQLFSKK
SQEIPQQMNG  SDCGMFACKY  ADCITKDRPI  NFTQQHMPYF  RKRMVWEILH
RKLL
```

```
                         Sequence Listing

SEQ ID NO: 2 Isoform 2 SENP1
MDDIADRMRM DAGEVTLVNH NSVFKTHLLP QTGFPEDQLS
LSDQQILSSR QGHLDRSFTC STRSAAYNPS YYSDNPSSDS FLGSGDLRTF
GQSANGQWRN STPSSSSSLQ KSRNSRSLYL ETRKTSSGLS NSFAGKSNHH
CHVSAYEKSF PIKPVPSPSW SGSCRRSLLS PKKTQRRHVS TAEETVQEEE
REIYRQLLQM VTGKQFTIAK PTTHFPLHLS RCLSSSKNTL KDSLFKNGNS
CASQIIGSDT SSSGSASILT NQEQLSHSVY SLSSYTPDVA FGSKDSGTLH
HPHHHHSVPH QPDNLAASNT QSEGSDSVIL LKVKDSQTPT PSSTFFQAEL
WIKELTSVYD SRARERLRQI EEQKALALQL QNQRLQEREH SVHDSVELHL
RVPLEKEIPV TVVQETQKKG HKLTDSEDEF PEITEEMEKE IKNVFRNGNQ
DEVLSEAFRL TITRKDIQTL NHLNWLNDEI INFYMNMLME RSKEKGLPSV
HAFNTFFFTK LKTAGYQAVK RWTKKVDVFS VDILLVPIHL GVHWCLAVVD
FRKKNITYYD SMGGINNEAC RILLQYLKQE SIDKKRKEFD TNGWQLFSKK
SQIPQQMNGS DCGMFACKYA DCITKDRPIN FTQQHMPYFR KRMVWEILHR
KLL SEQ ID NO: 3 (Isoform 1) C-Terminal Region SENP1
EFPEITEEMEKEIKNVFRNGNQDEVLSEAFRLTITRKDIQTLNHLNWLNDEI
INFYMNMLMERSKEKGLPSVHAFNTFFFTKLKTAGYQAVKRWTKKVDVFSVDI
LLVPIHLGVHWCLAVVDFRKKNITYYDSMGGINNEACRILLQYLKQESIDKKRKE
FDTNGWQLFSKKSQEIPQQMNGSDCGMFACKYADCITKDRPINFTQQHMPYFRK
RMVWEILHRKLL SEQ ID NO: 4 (Isoform 1) C-Terminal Region SENP1 C603S
EFPEITEEMEKEIKNVFRNGNQDEVLSEAFRLTITRKDIQTLNHLNWLNDEI
INFYMNMLMERSKEKGLPSVHAFNTFFFTKLKTAGYQAVKRWTKKVDVFSVDI
LLVPIHLGVHWCLAVVDFRKKNITYYDSMGGINNEACRILLQYLKQESIDKKRKE
FDTNGWQLFSKKSQEIPQQMNGSDSGMFACKYADCITKDRPINFTQQHMPYFRK
RMVWEILHRKLL SEQ ID NO: 5 (Isoform 2) C-Terminal Region SENP1
EFPEITEEMEKEIKNVFRNGNQDEVLSEAFRLTITRKDIQTLNHLNWLNDEI
INFYMNMLMERSKEKGLPSVHAFNTFFFTKLKTAGYQAVKRWTKKVDVFSVDI
LLVPIHLGVHWCLAVVDFRKKNITYYDSMGGINNEACRILLQYLKQESIDKKRKE
FDTNGWQLFSKKSQIPQQMNGSDCGMFACKYADCITKDRPINFTQQHMPYFRKR
MVWEILHRKLL SEQ ID NO: 6 (Isoform 1) Protease Region 450-613 SENP1
LTITRKDIQTLNHLNWLNDEIINFYMNMLMERSKEKGLPSVHAFNTFFFTK
LKTAGYQAVKRWTKKVDVFSVDILLVPIHLGVHWCLAVVDFRKKNITYYDSMG
GINNEACRILLQYLKQESIDKKRKEFDTNGWQLFSKKSQEIPQQMNGSDCGMFA
CKYADC SEQ ID NO: 7 (Isoform 1) Protease Region 450-613 SENP1 C603S
LTITRKDIQTLNHLNWLNDEIINFYMNMLMERSKEKGLPSVHAFNTFFFTK
LKTAGYQAVKRWTKKVDVFSVDILLVPIHLGVHWCLAVVDFRKKNITYYDSMG
GINNEACRILLQYLKQESIDKKRKEFDTNGWQLFSKKSQEIPQQMNGSDSGMFA
CKYADC SEQ ID NO: 8 SUMO1
MSDQEAKPSTEDLGDKKEGEYIKLKVIGQDSSEIHFKVKMTTHLKKLKES
YCQRQGVPMNSLRFLFEGQRIADNHTPKELGMEEEDVIEVYQEQTGGHSTV SEQ ID NO: 9 SUMO1 (1-92)
MSDQEAKPSTEDLGDKKEGEYIKLKVIGQDSSEIHFKVKMTTHLKKLKESYCQR
QGVPMNSLRFLFEGQRIADNHTPKELGMEEEDVIEVYQ
```

EMBODIMENTS

Embodiment 1

A method of detecting binding of an SENP1 polypeptide to a compound, the method comprising:

(i) contacting an SENP1 polypeptide with a compound;

(ii) allowing the compound to bind to the SENP1 polypeptide, thereby forming a SENP1-compound complex;

(iii) detecting the SENP1-compound complex using nuclear magnetic resonance, thereby detecting binding of the SENP1 polypeptide to the compound.

Embodiment 2

The method of embodiment 1, wherein the detecting comprises determining a chemical shift for an amino acid in an active site of the SENP1 polypeptide.

Embodiment 3

The method of embodiment 2, wherein the chemical shift in the presence of the compound is changed relative to the corresponding chemical shift in the absence of the compound.

Embodiment 4

The method of embodiment 2 or 3, wherein the amino acid is an amino acid of SEQ ID NOs:3, 4, 5, 6 or 7.

Embodiment 5

The method of embodiment 2 or 3, wherein the amino acid is selected from the group consisting of D550, H533, C603, W465, W534, L466, G531, C535, M552, G554, E469 and Q596.

Embodiment 6

The method of embodiment 2 or 3, wherein the amino acid is S603.

Embodiment 7

The method of embodiment 2 or 3, wherein the amino acid is amino acid residue 440-455, 463-473, 493-515, 529-535, 550-554, or 596-603 of SEQ ID NO:1.

Embodiment 8

The method of embodiment 1, wherein the SENP1 polypeptide comprises SEQ ID NOs:1, 2, 3, 4, 5, 6, or 7.

Embodiment 9

The method of embodiment 1, wherein the SENP1 polypeptide comprises amino acid residue 603 of SEQ ID NO:1.

Embodiment 10

The method of embodiment 9, wherein the SENP1 polypeptide comprises a mutation at amino acid residue 603 of SEQ ID NO:1.

Embodiment 11

The method of embodiment 10, wherein the mutation is C603S.

Embodiment 12

The method of embodiment 1, wherein the SENP1 polypeptide comprises amino acid residues 440-455, 463-473, 493-515, 529-535, 550-554, or 596-603 of SEQ ID NO:1.

Embodiment 13

The method of any one of embodiments 1-12, wherein the SENP1 or SENP1-compound complex is bound to a SUMO protein thereby forming a SENP1-SUMO complex or SENP1-SUMO-compound complex.

Embodiment 14

The method of embodiment 13, wherein the SUMO protein is a truncated SUMO protein.

Embodiment 15

The method of embodiment 2, wherein the active site is a catalytically active site.

Embodiment 16

The method of embodiment 2, wherein the active site is a site that binds to the SUMO protein.

Embodiment 17

The method of any one of embodiments 1-16, wherein the compound is a small molecule.

Embodiment 18

The method of any one of embodiments 1 or 8-17, wherein the detecting comprises producing an NMR spectra of the SENP1-compound complex and identifying a change in the NMR spectra relative to the absence of the compound.

Embodiment 19

The method of embodiment 18, wherein the change is a change in the chemical shift of an amino acid of SEQ ID NOs:3, 4, 5, 6 or 7.

Embodiment 20

The method of embodiment 18, wherein the change is a change in the chemical shift of an amino acid selected from the group consisting of D550, H533, C603, W465, W534, L466, G531, C535, M552, G554, E469 and Q596.

Embodiment 21

The method of embodiment 18, wherein the change is a change in the chemical shift of the amino acid S603.

Embodiment 22

The method of embodiment 18, wherein the change is a change in the chemical shift of an amino acid residue 440-455, 463-473, 493-515, 529-535, 550-554, or 596-603 of SEQ ID NO:1.

Embodiment 23

An aqueous composition comprising an SENP1 polypeptide at a pH from about 6.0 to about 7.5.

Embodiment 24

The aqueous composition of embodiment 23, wherein the pH is about 6.8.

Embodiment 25

The aqueous composition of embodiment 23 or 24, further comprising a buffering agent, reducing agent, solvent, a base, or combinations thereof.

Embodiment 26

The aqueous composition of any one of embodiments 23-25, further comprising sodium phosphate, dimethyl sulfoxide, D2O, sodium azide, dithiothreitol or combinations thereof.

Embodiment 27

The aqueous composition of embodiment 26, wherein the sodium phosphate is present at about 20 mM.

Embodiment 28

The aqueous composition of any one of embodiments 23-27, wherein the SENP1 polypeptide comprises SEQ ID NO:1, 2, 3, 4, 5, 6, or 7.

Embodiment 29

The aqueous composition of any one of embodiments 23-27, wherein the SENP1 polypeptide comprises amino acid residues 440-455, 463-473, 493-515, 529-535, 550-554, or 596-603 numbered relative to SEQ ID NO:1.

Embodiment 30

The aqueous composition of any one of embodiments 23-29, wherein the SENP1 polypeptide is bound to a SUMO protein thereby forming a SENP1-SUMO complex.

Embodiment 31

The aqueous composition of any one of embodiments 23-29, wherein the SENP1 polypeptide is bound to a compound thereby forming a SENP1-compound complex.

Embodiment 32

The aqueous composition of embodiment 31, wherein the SENP1 polypeptide is bound to a SUMO protein thereby forming a SENP1-SUMO-compound complex.

Embodiment 33

The aqueous composition of embodiment 30 or 32, wherein the SUMO protein is a truncated SUMO protein.

Embodiment 34

An NMR apparatus comprising an NMR sample container for NMR analysis, the NMR sample container comprising the aqueous composition of any one of embodiments 23-33.

Embodiment 35

A method of screening for an inhibitor of SENP1 comprising contacting a composition comprising an SENP1 polypeptide with a test compound and detecting whether the test compound binds the SENP1 polypeptide or fragment thereof by nuclear magnetic resonance.

Embodiment 36

The method of embodiment 35, wherein the detecting comprises determining a chemical shift for an amino acid in an active site of the SENP1 polypeptide.

Embodiment 37

The method of embodiment 36, wherein the amino acid is an amino acid of SEQ ID NOs:3, 4, 5, 6 OR 7.

Embodiment 38

The method of embodiment 36, wherein the amino acid is selected from the group consisting of D550, H533, C603, W465, W534, L466, G531, C535, M552, G554, E469 and Q596.

Embodiment 39

The method of embodiment 36, wherein the amino acid is S603.

Embodiment 40

The method of embodiment 36, wherein the amino acid is amino acid residue 440-455, 463-473, 493-515, 529-535, 550-554, or 596-603 of SEQ ID NO:1.

Embodiment 41

The method of embodiment 35, wherein the SENP1 polypeptide comprises SEQ ID NOs:1, 2, 3, 4, 5, 6, or 7.

Embodiment 42

The method of embodiment 35, wherein the SENP1 polypeptide comprises amino acid residue 603 of SEQ ID NO:1.

Embodiment 43

The method of embodiment 42, wherein the SENP1 polypeptide comprises a mutation at amino acid residue 603 of SEQ ID NO:1.

Embodiment 44

The method of embodiment 43, wherein the mutation is C603S.

Embodiment 45

The method of embodiment 35, wherein the SENP1 polypeptide comprises amino acid residues 440-455, 463-473, 493-515, 529-535, 550-554, or 596-603 of SEQ ID NO:1.

Embodiment 46

The method of any one of embodiments 35-45, wherein the SENP1 polypeptide is bound to a SUMO protein thereby forming a SENP1-SUMO complex.

Embodiment 47

The method of embodiment 46, wherein the SUMO protein is a truncated SUMO protein.

Embodiment 48

The method of any one of embodiments 35-47, wherein the chemical shift in the presence of the test compound is changed relative to the corresponding chemical shift in the absence of the test compound.

Embodiment 49

The method of any one of embodiments 35-47, wherein the SENP1 binds the compound forming an SENP1-compound complex and the detecting comprises producing an NMR spectra of the SENP1-compound complex and identifying a change in the NMR spectra relative to the absence of the compound.

Embodiment 50

The method of embodiment 49, wherein the change is a change in the chemical shift of an amino acid of SEQ ID NOs:3, 4, 5, 6 or 7.

Embodiment 51

The method of embodiment 49, wherein the change is a change in the chemical shift of an amino acid selected from the group consisting of D550, H533, C603, W465, W534, L466, G531, C535, M552, G554, E469 and Q596.

Embodiment 52

The method of embodiment 49, wherein the change is a change in the chemical shift of the amino acid S603.

Embodiment 53

The method of embodiment 49, wherein the change is a change in the chemical shift of an amino acid residue 440-455, 463-473, 493-515, 529-535, 550-554, or 596-603 of SEQ ID NO:1.

Embodiment 54

The method of embodiment 49, wherein the change is a change in the chemical shift of an amino acid in the active site of SENP1.

Embodiment 55

The method of embodiment 54, wherein the active site is a catalytically active site.

Embodiment 56

The method of embodiment 54, wherein the active site is a site that binds to the SUMO protein.

Embodiment 57

The method of any one of embodiments 35-56, wherein the test compound is a small molecule.

Embodiment 58

The method of any one of embodiments 35-57, wherein the composition is an aqueous solution.

Embodiment 59

The method of any one of embodiments 35-58, wherein the composition is at a pH from about 6.0 to about 7.5.

Embodiment 60

The method of embodiment 59, wherein the pH is about 6.8.

Embodiment 61

The method of any one of embodiments 35-60, wherein the composition further comprises a buffering agent, solvent, reducing agent, a base, or combinations thereof.

Embodiment 62

The method of any one of embodiments 35-60, further comprising sodium phosphate, D2O, sodium azide, dimethyl sulfoxide, dithiothreitol or combinations thereof.

Embodiment 63

The method of embodiment 62, wherein the sodium phosphate is present at about 20 mM.

Embodiment 64

A method of identifying an SENP1 inhibitor, the method comprising:
  combining an SENP1 polypeptide, a SUMO protein, and a test compound in a reaction vessel;
  allowing the SENP1 polypeptide, SUMO protein and test compound to form a SENP1-SUMO-compound complex; and
  detecting the SENP1-SUMO-compound complex thereby identifying the compound as a SENP1 inhibitor.

Embodiment 65

The method of embodiment 64, wherein one or more of the SENP1 polypeptide, SUMO protein or test compound is labeled.

Embodiment 66

The method of embodiment 65, wherein the label is a fluorescent label.

Embodiment 67

The method of any one of embodiments 64-66, wherein the test compound comprises a fluorescent label.

Embodiment 68

The method of any one of embodiments 64-67, wherein binding is detected by fluorescent polarization.

Embodiment 69

The method of embodiment 64, wherein binding is detected by detecting a change in the thermal properties of SENP1.

Embodiment 70

The method of embodiment 69, wherein the thermal property is the melting temperature of SENP1.

Embodiment 71

The method of any one of embodiments 64-70, wherein the SUMO is a truncated SUMO protein.

Embodiment 72

The method of any one of embodiments 64-70, wherein the SUMO comprises amino acid residues 1-92 of the SUMO protein.

Embodiment 73

The method of any one of embodiments 64-70, wherein the SUMO protein comprises SEQ ID NO:8.

Embodiment 74

The method of any one of embodiments 64-70, wherein the SUMO protein comprises SEQ ID NO:9.

Embodiment 75

The method of any one of embodiments 64-74, wherein the SENP1 polypeptide comprises SEQ ID NOs:1, 2, 3, 4, 5, 6, or 7.

Embodiment 76

The method of any one of embodiments 64-74, wherein the SENP1 polypeptide comprises amino acid residue 603 of SEQ ID NO:1.

Embodiment 77

The method of any one of embodiments 64-74, wherein the SENP1 polypeptide comprises a mutation at amino acid residue 603 of SEQ ID NO:1.

Embodiment 78

The method of embodiment 77, wherein the mutation is C603S.

Embodiment 79

The method of any one of embodiments 64-74, wherein the SENP1 polypeptide comprises amino acid residues 440-455, 463-473, 493-515, 529-535, 550-554, or 596-603 of SEQ ID NO:1.

Embodiment 80

The method of any one of embodiments 64 or 71-79, wherein the detecting is performed using nuclear magnetic resonance.

Embodiment 81

The method of embodiment 80, wherein the detecting comprises producing an NMR spectra of the SENP1-SUMO-compound complex and identifying a change in the NMR spectra relative to the absence of the test compound.

Embodiment 82

The method of embodiment 81, wherein the change is a change in the chemical shift of an amino acid in an active site of the SENP1 polypeptide.

Embodiment 83

The method of embodiment 82, wherein the active site is a catalytically active site.

Embodiment 84

The method of embodiment 82, wherein the active site is a site that binds to the SUMO protein.

Embodiment 85

The method of embodiment 82, wherein the amino acid is an amino acid of SEQ ID NOs:3, 4, 5, 6 OR 7.

Embodiment 86

The method of embodiment 82, wherein the amino acid is selected from the group consisting of D550, H533, C603, W465, W534, L466, G531, C535, M552, G554, E469 and Q596.

Embodiment 87

The method of embodiment 82, wherein the amino acid is S603.

Embodiment 88

The method of embodiment 82, wherein the amino acid is amino acid residue 440-455, 463-473, 493-515, 529-535, 550-554, or 596-603 of SEQ ID NO:1.

Embodiment 89

The method of any one of embodiments 64-88, wherein the test compound is a small molecule.

---

What is claimed:

1. A method of screening for a binding compound of sentrin/SUMO-specific protease 1 (SENP1) comprising contacting a composition comprising an SENP1-small-ubiquitin-like modifier (SUMO) complex with a test compound and detecting whether the test compound binds SENP1 or a fragment thereof by nuclear magnetic resonance.

2. The method of claim 1, wherein the detecting comprises determining a chemical shift for an amino acid in an active site of SENP1.

3. The method of claim 2, wherein the chemical shift in the presence of the compound is changed relative to the corresponding chemical shift in the absence of the compound.

4. The method of claim 3, wherein the amino acid is selected from the group consisting of an amino acid residue corresponding to D550, H533, C603, W465, W534, L466, G531, C535, M552, G554, E469, and Q596 of SEQ ID NO:1.

5. The method of claim 1, wherein SENP1 comprises SEQ ID NOs: 1, 2, 3, 4, 5, 6, or 7.

6. The method of claim 1, wherein SENP1 comprises a mutation at an amino acid residue corresponding to amino acid residue 603 of SEQ ID NO:1.

7. The method of claim 1, wherein the detecting comprises producing an NMR spectra of a SENP1-SUMO-compound complex and identifying a change in the NMR spectra relative to the absence of the compound.

8. The method of claim 7, wherein the change is a change in the chemical shift of an amino acid of SEQ ID NOs: 3, 4, 5, 6 or 7.

9. The method of claim 7, wherein the change is a change in the chemical shift of the amino acid corresponding to the amino acid C603 of SEQ ID NO:1.

10. The method of claim 7, wherein the change is a change in the chemical shift of an amino acid residue 440-455, 463-473, 493-515, 529-535, 550-554, or 596-603 of SEQ ID NO:1.

11. The method of claim 1, further comprising a biochemical assay.

12. The method of claim 11, wherein the biochemical assay is an enzyme kinetics assay, gel based assay, bioluminescent assay, or fluorescent assay.

* * * * *

UNITED STATES PATENT AND TRADEMARK OFFICE
CERTIFICATE OF CORRECTION

| | |
|---|---|
| PATENT NO. | : 11,041,859 B2 |
| APPLICATION NO. | : 15/783423 |
| DATED | : June 22, 2021 |
| INVENTOR(S) | : Yuan Chen, Chih-Hong Chen and Andrew Namanja |

Page 1 of 1

It is certified that error appears in the above-identified patent and that said Letters Patent is hereby corrected as shown below:

In the Specification

At Column 1, Lines 18 to 21, delete "This invention was made with government support under NM Grant Nos. R01GM074748, R01GM086171 and R01GM102538. The government has certain rights in the invention." and insert --This invention was made with government support under R01 GM074748, R01 GM102538, and R01 GM086171 awarded by the National Institutes of Health. The government has certain rights in the invention.--

Signed and Sealed this
Seventh Day of October, 2025

John A. Squires
*Director of the United States Patent and Trademark Office*